(12) United States Patent
Siiman et al.

(10) Patent No.: US 6,387,622 B1
(45) Date of Patent: *May 14, 2002

(54) LIGAND-AMINODEXTRAN-MARKER CONJUGATES AND USES THEREOF

(75) Inventors: Olavi Siiman, Davie; Alexander Burshteyn, Hialeah; Ravindra Mylvaganam, Hollywood; Robert Raynor, Cooper City; Patricia Roth, Pembroke Pines; Cecilia Smith, Miami; Julie Wilkinson, Weston, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/403,919

(22) PCT Filed: May 14, 1998

(86) PCT No.: PCT/US98/09774

§ 371 Date: Oct. 27, 1999

§ 102(e) Date: Oct. 27, 1999

(87) PCT Pub. No.: WO98/52040

PCT Pub. Date: Nov. 19, 1998

Related U.S. Application Data

(63) Continuation-in-part of application No. 08/976,031, filed on Nov. 21, 1997, now Pat. No. 5,994,089, which is a continuation-in-part of application No. 08/857,941, filed on May 16, 1997, now Pat. No. 5,891,741.

(51) Int. Cl.$^7$ ............................................. G01N 33/68
(52) U.S. Cl. .................. 435/6; 435/7.22; 435/7.23; 435/7.24; 435/7.25; 435/7.2; 436/172; 436/512; 436/513; 436/529; 436/800; 436/805; 530/391.1; 530/391.3; 530/391.5
(58) Field of Search .............................. 435/7.23, 7.24, 435/7.22, 7.2, 7.25, 6; 530/391.1, 391.3, 391.5; 436/512, 513, 529, 800, 805, 172

(56) References Cited

U.S. PATENT DOCUMENTS

| | | |
|---|---|---|
| 4,499,052 A | 2/1985 | Fulwyler |
| 5,206,143 A | 4/1993 | Horan et al. |
| 5,527,713 A | 6/1996 | Bolton et al. |
| 5,538,855 A | 7/1996 | Orfao de Matos |
| 5,891,741 A | 4/1999 | Siiman et al. |
| 5,994,089 A | 11/1999 | Siiman et al. |

FOREIGN PATENT DOCUMENTS

| | | |
|---|---|---|
| EP | 219309 A1 | 4/1987 |
| WO | 93/03062 | 2/1993 |
| WO | 94/29724 | 12/1994 |
| WO | 95/24631 | 9/1995 |

OTHER PUBLICATIONS

Saunders, A.M., et al., "A New Immune Monitoring System for the Determination of Lymphoid Cell Subsets", *Ann. N.Y. Acad. Sci.*, 468:128 (1986).

Horan, P.K., et al., "Improved Flow Cytometric Analysis of Leukocyte Subsets: Simultaneous Identification of Five Cell Subsets Using Two–color Immunofluorescence", *Proc. Natl. Acad. Sci. USA*, 83:8361–8365 (1986).

Liu, C., et al., "Flow Cytometric Monitoring of Human Immunodeficiency Virus–Infected Patients", *Am. J. Clin. Path.*, 92:721–728 (1989).

Carayon, P., et al, "Simultaneous Identification of Eight Leucocyte Subsets of Human Peripheral Blood Using Three– colour Immunofluorescence Flow Cytometric Analysis", *J. Imunol. Methods*, 138:257–264 (1991).

McHeyzer–Williams, M.G., et al., "Tracking Antigen–Specific Helper T Cell Responses," *Current Opinion in Immunol.*, 278–284 (1996).

Waggoner, A.S., et al., "PE–CY5, A New Fluorescent Antibody Label for Three–color Flow Cytometry with a Single Laser," *Ann. N.Y. Acad. Sci.*, 677:185–193 (1993).

*Primary Examiner*—Christopher L. Chin
(74) *Attorney, Agent, or Firm*—Mary E. Bak; Mitchell E. Alter

(57) ABSTRACT

Ligand-aminodextran-(phycobiliprotein or tandem dye) conjugates useful for detection of a desired target biological material by providing an enhanced fluorescent signal are described. Also described is a method for a single-measurement quantification of multiple populations of cells based upon the labeling of different pairs of cell populations, each pair containing mutually exclusive cell receptors which are expressed at substantially similar receptor densities with labeled ligands for each receptor. One cell population is labeled with a ligand capable of binding to a first cell surface receptor which ligand is directly conjugated to a fluorescent phycobiliprotein or tandem dye; and a second cell population is labeled with a ligand capable of binding to a second cell surface receptor, which ligand is cross-linked to an aminodextran to a fluorescent phycobiliprotein or tandem dye.

27 Claims, 24 Drawing Sheets

SDP DIFFERENTIAL WEIGHT

SDP DIFFERENTIAL WEIGHT

FIG. 10A
| μg/TEST | S/N | | MFI-POS | | MFI RATIO |
|---|---|---|---|---|---|
| | CD4-ECD | CD4-5X-Amdex-ECD | CD4-ECD | CD4-5X-Amdex-ECD | |
| 0.015 | 99 | 239 | 18 | 267 | 5.3 |
| 0.03 | 158 | 213 | 29 | 349 | 7.0 |
| 0.06 | 211 | 169 | 41 | 359 | 7.2 |
| 0.125 | 237 | 102 | 47 | 359 | 7.2 |
| 0.25 | 245 | 90 | 50 | 398 | 8.0 |
| 0.5 | 248 | 52 | 53 | 485 | 9.7 |
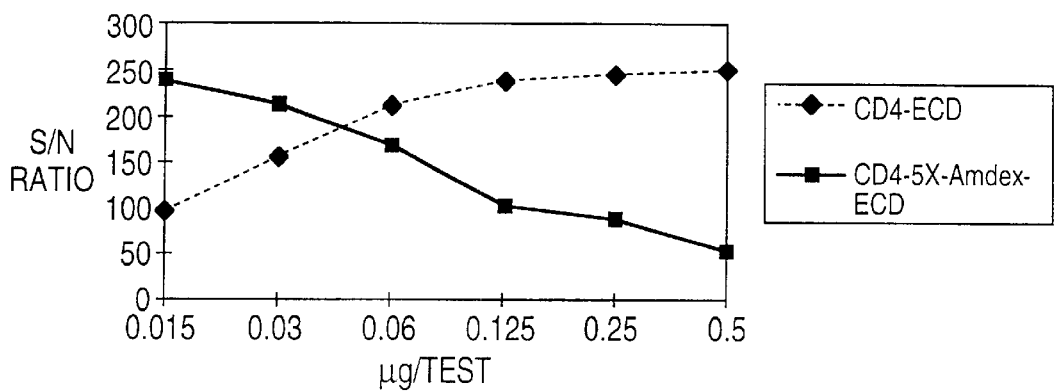
FIG. 10B
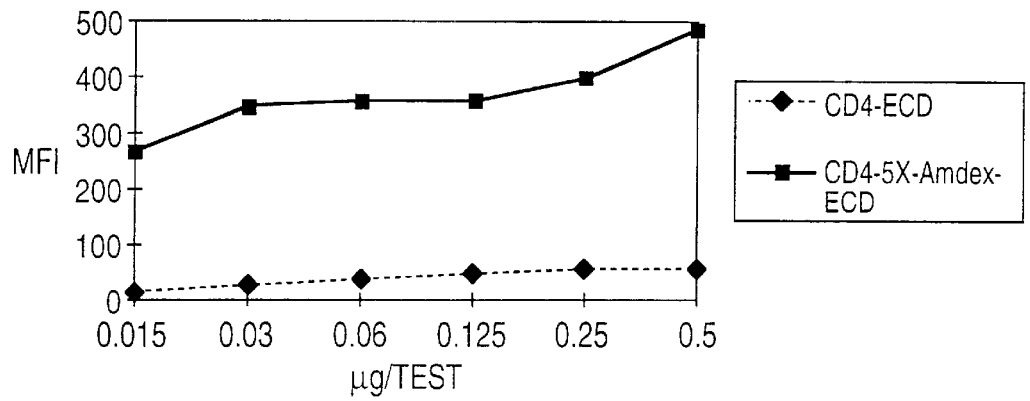
FIG. 10C CD56-PE, CD4-5X-Amdex-PE

CD4-PE, CD56-PE

CD19-PE, CD4-5X-Amdex-PE

CD4-PE, CD19-PE

CD8αβ-PE, CD4-5X-Amdex-PE

CD4-PE, CD8αβ-PE

CD19-PC5, CD8αβ-5X-Amdex-PC5

CD19-PC5, CD8αβ-5X-Amdex-PC5

CD8αβ-PC5, CD19-PC5

LIGAND-AMINODEXTRAN-MARKER CONJUGATES AND USES THEREOF

This application is a continuation-in-part of Ser. No. 08/976,031 filed Nov. 21, 1997, now U.S. Pat. No. 5,994,089 which is a UP of Ser. No. 08/857,941 filed May 16, 1997 now U.S. Pat. No. 5,891,741.

FIELD OF THE INVENTION

The present invention relates to methods for analyses of cell populations using fluorescent labels or markers.

BACKGROUND OF THE INVENTION

Multiplex labeling of cells for analysis of mixed cell populations by flow cytometry has progressed in various ways. Only a finite number of fluorescence emission colors of known organic fluorophores can be squeezed into the visible-near-UV-near-IR spectral regions in which flow cytometry measurements are made. The limitations have been dictated by the bandwidths of emission bands, the spectral overlap between these emission bands, and the excitation wavelength requirements. Up to eight colors requiring three laser lines have been introduced in various stages: two- to four-color [H. M. Shapiro in *Practical Flow Cytometry*, 3rd ed., Wiley-Liss, Inc., New York, N.Y., 1995, Chap. 7, p. 291]; five color [A. J. Beavis and K. J. Pennline, *Cytometry*, 15: 371–376 (1994); M. C. O'Brien et al, *Cytometry*, 21:76–83 (1995); M. Roederer et al, *Cytometry*, 21: 187–196 (1995)]; six color [M. Roederer et al, *Cytometry*, 24: 191–197 (1996)]; seven color for imaging [T. Ried et al, *Proc. Natl. Acad. Sci. USA*, 89: 1388–1392 (1992); A. Gothot et al, *Cytometry*, 24: 214–225 (1996)]; and eight color [M. Roederer et al, *Tissue Antigens*, 48: 485 (1996), abstract TC-6-02]. The six and seven color cases appear to represent the present upper limit for flow cytometry applications in which known organic dyes are used as fluorescent labels, since the eight-color example cannot as yet be considered to be of clinical significance due to severe overlap between emission bands of the fluorochromes.

As the upper limit in the number of usable colors was reached, other methods, based on fluorescence intensity differences, either intrinsic to analyzed cell populations or contrived by various means, have been described. Mutually exclusive pairs of targeted white blood cell populations with widely different, intrinsic numbers of receptors per cell can be labeled by a single color marker and analyzed by flow cytometry [U.S. Pat. No. 5,538,855]. U.S. Pat. No. 4,499,052 describes a method of distinguishing multiple subpopulations of cells by labeling specific antibodies with fluorescent polymers containing different, pre-selected ratios of fluorescein and rhodamine [See also, A. M. Saunders and C.-H. Chang, *Ann, N.Y. Acad. Sci.*, 468:128 (1986)]. H. M. Shapiro in *Practical Flow Cytometry*, 1st ed., Alan R. Liss, Inc., pp. 127–128 (1985) describes a method using three different antibodies labeled with fluorochrome A, B, and a combination of A and B. U.S. Pat. No. 5,206,143 describes saturated and sub-saturated amounts of marker mixed with the sample of cells. Quantitative differences in fluorescence intensity of one or two fluorochromes used for labeling cells were obtained. Each subset to be analyzed was labeled with a different amount of fluorochrome, exhibiting fluorescence intensities within a distinguishable range. Mixtures of fluorescein- and phycoerythrin-labeled and unlabeled antibodies were used to produce fluorescence intensity differences of several orders of magnitude among various cell subsets [P. K. Horan et al, *Proc. Natl. Acad. Sci. USA*, 3: 8361–8365 (1986)]. Use of this method to identify helper and suppressor/cytotoxic T cells, NK and B cells, and monocytes in whole blood was shown [C.-M. Liu et al, *Am. J. Clin. Path*, 92: 721–728 (1989)]. Further, eight leukocyte subsets in whole blood were analyzed with six monoclonal antibodies linked with one of three fluorochromes [P. Carayon et al, *J. Immunol. Methods*, 138: 257–264 (1991)].

A variety of antibody-aminodextran conjugates are described in U.S. Pat. No. 5,527,713 and U.S. Pat. No. 5,658,741 described the preparation of antibody-aminodextran conjugates containing two or more antibody molecules per conjugate. Recently, polymeric carriers containing the divinyl sulfone moiety for covalent attachment of protein and other molecular species were described in European Patent No. 0 594 772 B1.

The human genome project has been a driving force behind the development of new detection and sequencing methods for nucleic acids. Several non-radioactive gene probes, oligos with attached fluorescent dye, that hybridize, or bind to sample DNA, have been described [L. M. Smith et al., *Nature*, 321:674–679(1986) and L. M. Smith et al., *Nucleic Acids Res.*, 13:2399–2412(1985)] and are being used. Automated DNA sequencers use four fluorescent dyes with non-overlapping emission bands, one per nucleotide base. Electrophoretic mobilities of the fluorescent dye-oligo primer conjugates need to be similar for all four conjugates. Also, the molecular weights of the conjugates cannot be too high otherwise they will not move through the polyacrylamide or agarose gel used in the electrophoresis. Molecules do not travel through gel pores but follow a tortuous path through entanglements of gel fibers by a process called forced reptation [G. W. Slater et al., *Macromolecules*, 24:6715–6720 (1991); P.-G. de Gennes, *J. Chem. Phys.*, 55:572 (1971)]. Large molecules can become stuck in the gel in forms such as "hernias", "cul-de-sac", or "impaled spirals" in gel pores. However, electrophoretic methods using pulsed electric fields [U.S. Pat. No. 4,971,671] have been successfully applied to separate DNA fragments containing up to about 5,000,000 base pairs.

An alternative method for sequencing DNA is a carryover from the Southern hybridization technique [E. M. Southern, *J. Mol. Biol.*, 98: 503 (1975)], wherein DNA is digested with one or more restriction enzymes, and the resulting fragments are separated according to size by electrophoresis through an agarose gel. The DNA is denatured in situ and transferred from the gel to a solid support, usually a nitrocellulose filter or nylon membrane. Without the use of a radiolabel as the probe, the DNA attached to the filter is hybridized to fluorescence-labelled DNA or RNA [E. M. Southern, *Trends Genet.*, 12: 110–115 (1996)], which allows detection of the positions of bands complementary to the probe.

The gene chip probe does not depend on the use of gels or electrophoresis. This solid state surface probe has been described in Z. Strezoska et al., *Proc. Natl. Acad. Sci. USA*, 88: 10089–10093 (1991); R. Drmanac et al., *Science*, 260: 1649–1652 (1993); A. B. Chetverin and F. R. Kramer, *Biotechnology*, 12: 1093–1099 (1994); T. Studt, *R&D Magazine* (February 1998), and is being designed to allow up to 400,000 oligos per chip for simultaneous DNA/RNA analysis.

The SER-gene probe [T. Vo-Dinh et al, *Anal. Chem.* 66: 3379–3383 (1994) and U.S. Pat. No. 5,306,403] uses a non-fluorescent dye conjugated to an oligonucleotide to bind nucleic acid on a nitrocellulose membrane. After hybridization the SER-Gene probe-DNA complex is transferred onto a surface-enhanced Raman scattering (SERS) active substrate to detect SERS spectra from the dye.

The need for increased sensitivity of probes used in automated DNA sequence analysis by attaching multiple dye molecules per oligonucleotide primer were recognized as early as in L. M. Smith et al, *Nature*, 321: 674–679 (1986). However, only a limited degree of fluorescence enhancement has been possible for dye-oligo conjugates that are constrained to low molecular weight for separation by gel electrophoresis. The use of two dye molecules per oligo in which the pair of dye molecules is related by donor-acceptor type energy transfer to enhance fluorescent intensities from 2- to 6-fold has recently been described in J. Ju et al., *Proc. Natl. Acad. Sci. USA*, 92: 4347–4351 (1995); J. Ju et al., *Anal. Biochem.*, 231: 131–140 (1995); M. L. Metzker et al., *Science*, 271: 1420–1422 (1996).

The measurement of antigen-specific T cells requires recognition by a polymorphic surface T cell receptor which is unique for each different antigen. The ligand for the TCR is an antigenic peptide folded into the groove of a Major Histocompatability (MHC) molecule. This is a low affinity interaction which can be detected on the cell surface only if avidity is increased by multimerization of the MHC/peptide complex. This may be accomplished by attachment of a biotinylated complex to a multivalent avidin molecule which, in turn is attached to a phycoerythrin molecule [M G McHeyszer-Williams et al., *Current Opinion in Immunol.*, 278–284 (1996). The low frequency of these cells during any given response makes it imperative that signal to noise ratios are large enough to detect rare events.

There remains a need in the art for methods to permit greater numbers of cell populations and other biological materials to be distinguished by fluorescent markers.

SUMMARY OF THE INVENTION

The present invention overcomes multiple problems in fields which require detection of biological materials, particularly those materials which are present in low numbers and/or contain low numbers of receptors or other binding partners on the target material.

In one aspect, the invention provides a method for a single-measurement quantification of multiple populations of cells based upon the labeling of different pairs of cell populations. Each cell population of the pair contains mutually exclusive cell receptors which are expressed at substantially similar receptor densities on each cell population of the pair. One cell population is labeled with a ligand capable of binding to a first binding partner (e.g., a receptor), which ligand is directly conjugated to a marker, e.g., a fluorescent phycobiliprotein. A second cell population is labeled with a ligand capable of binding to a second binding partner (e.g., a receptor), which ligand is cross-linked to an aminodextran which is conjugated to the marker (e.g., fluorescent phycobiliprotein). Upon laser activation, the directly labeled ligands bound to the first binding partner produce a different detectable marker intensity than the labeled cross-linked ligands bound to the second binding partner. Use of such pairs of ligands enable two populations of cells with similar binding partner densities to be distinguished with the use of a single color marker.

In another aspect, the invention provides a method for a single-measurement quantification of multiple populations of cells based upon the labeling of different pairs of cell populations, each pair containing mutually exclusive cell receptors which are expressed at substantially similar receptor densities. For each first population of cells in a pair of cell populations, a different first ligand is labeled directly with a different phycobiliprotein. For each second population of cells in a pair, a second ligand which differs from the first ligand of the pair forms a conjugate by cross-linking to an aminodextran, and being labeled with the phycobiliprotein. Within each pair of first and second ligands, the phycobiliproteins are the same; however, each separate pair of cell populations uses a different color phycobiliprotein (or a phycobiliprotein excited by a different laser excitation line) to label its first and second ligands. Following incubation of a biological sample containing one or more pairs of cell populations with each pair of first and second labeled ligands for a time sufficient to permit receptor-labeled ligand complexes to form therebetween, the sample is subjected to a laser excitation line to cause the labels to fluoresce. The intensities of fluorescent emissions of each first cell population bound to each labeled first ligand and the fluorescent emissions of each second population bound to each labeled second ligand are measured using flow cytometry. By this method, the cell populations may be distinguished by detectably different intensity and color signals. This method can be optionally modified by the use of labels which produce fluorescent emissions that do not overlap with the phycobiliproteins used (i.e., labels which are generally proteinaceous or small molecules which emit below 550 nm, such as FITC). Thus, this method permits up to seven markers to be employed in a single quantitation measurement using a single laser, four color flow cytometer.

In still another aspect, the method is employed to distinguish between four cell populations using two single color phycobiliproteins. In a further aspect, the method is employed to distinguish between six cell populations using three single color phycobiliproteins. A fourth color, such as FITC, may be added to bring the total number of markers used in the method to seven.

In yet a further aspect, the method involves the use of two laser excitation lines, thereby permitting a maximum of twelve different signals having different color and intensity characteristics, enabling the identification of twelve different cell populations in a method which does not rely on substantial differences between the densities of the cell surface receptors, but only on the use of mutually exclusive cell surface receptors for each pair of cell populations to be identified.

In yet a further aspect, the present invention provides a ligand-aminodextran-(phycobiliprotein or tandem dye)-conjugate, which conjugate contains two to twenty phycobiliprotein or tandem dye molecules per amino dextran molecule, wherein said dextran has a degree of substitution with a C2 to C6 diaminoalkane of $1/142–1/5$. Also included as an aspect of this invention are methods of making and using such ligand-aminodextran-(phycobiliprotein-tandem dye) conjugates.

Other aspects and advantages of the present invention are described further in the following detailed description of the preferred embodiments thereof.

BRIEF DESCRIPTION OF THE DRAWINGS

Each histogram in FIGS. 1A, 1B, 2A, 2B, 3A, 3B, 3C, 4A, 4B and 5A–5F shows a plot of cell number (vertical axis) versus mean channel fluorescence intensity (horizontal axis).

FIG. 10A is a tabular report of the S/N, positive mean fluorescence and MFI ratio for the direct CD4-ECD ligand and a single pooled sample of CD4-5X-Amdex-ECD conjugates from trial 2 of Example 20. These were titered with two-fold serial dilutions, starting at 0.5 μg (based on ELISA analysis for CD4-5X-Amdex-ECD and $A_{280}$ value for CD4-ECD) per tube.

FIG. 10B is a graph plotting the S/N ratio vs. microgram/test of the results of FIG. 10A.

FIG. 10C is a graph plotting MFI vs. microgram/test of the results of FIG. 10A.

FIG. 20A is a histogram showing dual color, four markers CD56-PE/CD4-5X-Amdex-PE and CD19-PC5/CD8αβ-5X-Amdex-PC5, for Q-PREPed and washed samples run with 488.0 nm Ar+ laser excitation on the Coulter XL flow cytometer.

FIG. 20B is a histogram of the same experiment showing use of two additional color markers, CD3-ECD and CD45RO-FITC mixed with whole blood already containing the other markers.

FIG. 20C is a histogram of the same experiment showing the detection of fluorescence for CD3-ECD vs. CD56-PE and CD4-5X-Amdex-PE.

FIG. 20D is a histogram of the same experiment showing the detection of fluorescence for CD3-ECD vs. CD19-PC5 and CD8αβ-5X-Amdex-PC5.

DETAILED DESCRIPTION OF THE INVENTION

Figure 1A:
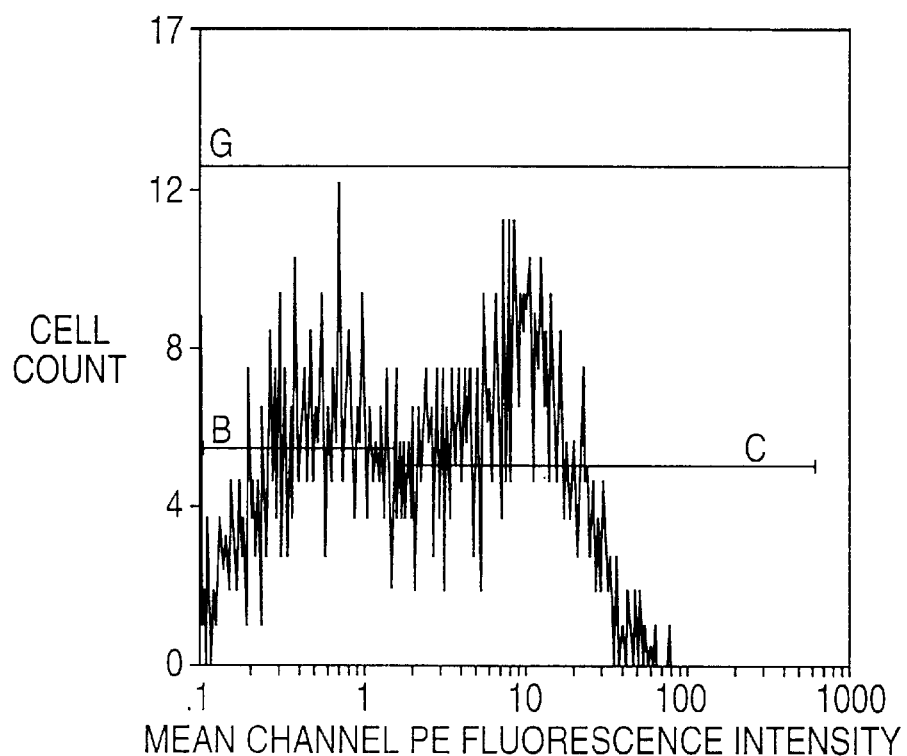
FIGS. 1A and 1B compare the fluorescence intensity of lymphocytes marked by the direct conjugate BB27-PE and by the aminodextran crosslinked conjugate BB27-5X-Amdex-PE, when each conjugate is mixed with whole blood.

The present invention provides methods aminodextran-crosslinked conjugates useful for obtaining enhanced fluorescence intensities and method for using these conjugates.

Briefly, crosslinked conjugates are loaded with substantially more fluorescent marker (e.g., phycoerythrin (PE)) than the direct 1:1 ligand-PE conjugates by simultaneously reacting iminothiolane-activated antibody and fluorescent marker (e.g., PE) with sulfo-SMCC-activated aminodextran in appropriate molar ratios. Thus, use of these loaded conjugates in saturation amounts in analysis of cell subsets in biological samples result in amplification of the fluorescent signals from individually-marked cells by a factor of two- to twenty-fold over the fluorescence intensity from cells marked with direct ligand-PE conjugates. The amplification of fluorescence was initially demonstrated for marked cells which usually showed dim fluorescence intensity when their receptors were saturated with direct antibody-PE conjugates. In one example, the invention involves the use of crosslinked antibody-PE conjugates for which the antigenic receptors on white blood cells are few in number such that fluorescence signals of appropriate magnitude can then be observed above the background fluorescence of cells with the antibody-aminodextran-PE markers. Antibodies for which cell surface receptors exist in larger numbers, 1000 per cell and higher, can also be used in the preparation of aminodextran-crosslinked antibody-PE conjugates, which can be used to further amplify fluorescence intensities of targeted cell populations. Further, other ligands may be substituted for antibodies, and other binding partners substituted for cell surface receptors to enable detection of a variety of biological materials, as discussed below.

The present invention also provides methods which permit a second round of fluorescent marker (e.g., PE) activation in tandem dyes. This permits extension of the number of fluorescence colors that can be obtained with the combination of direct and aminodextran-crosslinked antibody-fluorescent dye conjugates, fluorescent marker (PE)-tandem dye molecules, that can be excited with the same laser line, 488.0 nm Ar+, as PE, to a set of three color, two intensity per color, markers. These tandem dyes are discussed herein as are these methods.

For convenience throughout this specification, reference is made to white blood cells (WBC). However, one will readily understand that the methods of the invention may be readily applied to other cell populations for which analysis is desired. Such cell populations may include; e.g. and without limitation, tissue-derived cells, tumor cells, blood cells, and cells from pathogenic organisms. The methods of the invention may also be utilized to detect various other biological materials, including, e.g., individual nucleotide bases (e.g., for sequencing), amino acids, viruses and the like. See, e.g., Table 1.

In one embodiment, the present invention provides an improved method of quantifying multiple subsets of white blood cell populations by combining several types of "markers" for use in flow cytometry. Specifically, a method for a single-measurement quantification of multiple populations of WBC having substantially similar cell surface receptor densities may occur in a flow cytometric analysis by using the following steps. One cell population which is characterized by a particular cell surface receptor which is not present on a second cell population is incubated with a ligand (preferably an antibody) capable of binding to the cell surface receptor. This ligand is conventionally, directly conjugated to a fluorescent phycobiliprotein. A second cell population which is characterized by the presence of a second cell surface receptor which is different from the receptor on the first cell population and not found on the first cell population is incubated with a ligand capable of binding to this cell surface receptor and not the first cell surface receptor. This second ligand is preferably an antibody cross-linked to the same fluorescent phycobiliprotein through an aminodextran carrier. Upon excitation by a laser, the phycobiliprotein produces a different detectable fluorescence intensity for each cell population, due to the differences between its direct conjugation to the ligand binding the first cell surface receptor and its cross-linked conjugation to the ligand binding the second cell surface receptor. Thus a single color phycobiliprotein may distinguish between two cell populations based on differences in fluorescent intensity.

To facilitate understanding of the methods and compositions of this invention, the following descriptions of the components used in this method are described as follows.

A. Ligands

As defined herein, ligands include various agents which detect and react with one or more specific binding partners which are on the surface or inside a cell (formed body) or in solution. Ligands inside a cell or formed body are made accessible or brought to the surface by some process such as translocation, permeabilization, electroporation, etc. Examples of ligands within the meaning of the present invention and their partners include those listed in Table 1.

TABLE 1

| LIGAND | SPECIFIC BINDING PARTNER |
|---|---|
| Antibody | Antigen |
| Natural ligands: | |
| cytokine or chemokine | CK receptor |
| hormone | Hormone receptor |
| growth factor | Growth factor receptor |
| Secondary reagents: | |
| streptavidin | Biotinylated antibody — antigen |
| antibody | Antibody — antigen |
| Pharmaceuticals: | |
| drugs | Drug receptor |
| Solubilized natural ligands: | |
| counter-receptor | receptor |
| CTLA-4 | B7 (CD80/86) |
| Lectins (agglutinin) | Complementary carbohydrate or oligosaccharide on cell-surface glycoprotein |
| MHC-peptide complex | T cell receptor (TCR) |
| Oligonucleotide | Complementary sequences in nucleic acids, DNA or RNA |

The methods useful for construction of such ligands are known to those of skill in the art. All such ligands are characterized by the desired ability to bind the specified cell surface receptor on a population of cells. In one preferred embodiment, the ligand of the invention is a component which preferentially binds to all or a portion of a cell surface receptor. Thus, a ligand useful in this embodiment of the invention may be an antibody or a functional fragment thereof capable of binding to a cell surface receptor on a WBC population. Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')2, humanized or human antibodies, recombinant or synthetic constructs containing the complementary determining regions of an antibody, and the like.

Monoclonal antibodies used in the examples of this invention were generally obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, *Nature*, 256: 495–497 (1975). Of course, the particular method of making and the type of monoclonal antibody is not limited to such techniques and it is envisioned that any technique for making such antibodies is within the practice of the invention. Any ligand which can target receptor sites on, or in, cells may be used, since the amplification of fluorescent intensities using the antibody-dextran-phycobiliprotein conjugate does not depend on the density of the particular receptor sites on a cell. The selection of the ligand is not a limiting factor in this invention.

B. Markers: Phycobiliproteins or Biliproteins, Tandem Dyes and Others

The term "markers" generally refers to molecules, preferably proteinaceous, but also small chemical molecules, which enable detection by emitting a detectable signal of a particular wavelength upon excitation by a laser. Phycobiliproteins, tandem dyes, certain fluorescent proteins, small chemical molecules, and certain molecules detectable by other means can all be considered markers for flow cytometry analyses. See, e.g., the markers listed in *Handbook of Fluorescent Probes and Research Chemicals*, 6th Ed., R. P. Haugland, Molecular Probes, Inc., Eugene, Oreg. (1996). Throughout this specification, the term "markers" may also be used to refer to the conjugates formed by the ligand which is directly labeled with a particular marker, e.g., CD56-PE, or the conjugates formed by the ligand which is cross-linked to a particular marker through an aminodextran, e.g., CD56-5X Amdex-PE. The term will be clear from the context of this application.

"Phycobiliproteins" are a family of macromolecules found in red algae and blue-green algae. The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons. The biliproteins will normally be comprised of from 2 to 3 different subunits, where the subunits may range from about 10,000 to about 60,000 molecular weight. The biliproteins are normally employed as obtained in their natural form from a wide variety of algae and cyanobacteria.

The presence of the protein in the biliproteins provides a wide range of functional groups for conjugation to proteinaceous and non-proteinaceous molecules. Functional groups which are present include amino, thiol, and carboxyl. In some instances, it may be desirable to introduce functional groups, particularly thiol groups when the biliprotein is to be conjugated to another protein. Each phycobiliprotein molecule contains a large number of chromophores. An exemplary ligand, e.g., an antibody molecule directly labeled with fluorescein will have between 1 and 3 chromophores associated with it. An antibody molecule (for example) directly labeled by conjugation with a phycobiliprotein may have as many as 34 associated chromophores, each with an absorbance and quantum yield roughly comparable to those of fluorescein.

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and found in M. C. Custer and M. T. Lotze, *J. Immunol. Methods*, 128, 109–117 (1990), to be the only tested fluorophore that produced adequate signal.

The tandem dyes are non-naturally occurring molecules which may be formed of a phycobiliprotein and another dye. See, for example, U.S. Pat. No. 4,542,104 and U.S. Pat. No. 5,272,257. Examples of tandem dyes useful in the present invention are phycoerythrocyanin or PC5 (PE-Cy5, phycoerythrin-cyanin 5.1; excitation, 486–580 nm, emission, 660–680 nm) [A. S. Waggoner et al, *Ann, N.Y. Acad. Sci.*, 677 :185–193 (1993) and U.S. Pat. No. 5,171, 846] and ECD (phycoerythrin-texas red; excitation, 486–575 nm, emission, 610–635 nm) [U.S. Pat. No. 4,542, 104 and U.S. Pat. No. 5,272,257. Other known tandem dyes are PE-Cy7, APC-Cy5, and APC-Cy7 [M. Roederer el al, *Cytometry*, 24:191–197 (1996)]. Since tandem dyes, PC5 and ECD, have been successfully directly conjugated to monoclonal antibodies by several methods which involve iminothiolane activation of the dye, the procedures are anticipated to be transferable to preparation of aminodextran-crosslinked antibody-tandem dye conjugates as described herein.

Still other markers which may be directly conjugated to a ligand and used with the phycobiliproteins or tandem dyes in this invention to add additional numbers of markers (labeled ligands) to the method include small molecules which upon excitation emit wavelengths of less than 550 nm. Such molecules do not overlap with the emissions of the phycobiliproteins. One example of such a marker is fluorescein isothiocyanate (FITC). Others are listed in the Handbook cited above.

Still other markers which may be employed in this method to provide additional colors are the proteins known as the green fluorescent proteins and blue fluorescent proteins; also useful may be markers which emit upon excitation by ultraviolet light.

The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained conmmercially from known sources.

C. Ligand-Amimodextran-Phycobiliprotein or Tandem Dye) Conjugates

The conjugates of the present invention are crosslinked dextran, ligand-(phycobiliprotein or tandem dye) conjugates containing up to twenty five phycobiliprotein or tandem dye molecules per dextran molecule, and are preferable soluble in aqueous media (e.g., 1×PBS). These conjugates are advantageous in that they are able to produce an amplification of fluorescence intensity over direct antibody-phycobiliprotein labeled cells of two fold or greater.

Suitable dextrans have relatively high molecular weights and retain their solubility in aqueous media, i.e., between about 2–5 MDa. Preferably, the dextran component of these conjugates is aminodextran. Desirably, the cross-linked aminodextran-(phycobiliprotein or tandem dye) conjugate contains two to twenty phycobiliproteins or tandem dye molecules per aminodextran molecule, wherein said dextran has a low degree of substitution ($1/142$ to $1/5$) in dextran of 2MDa. In one exemplary aminodextran, the degree of substitution ranges from $1/45$ to $1/5$ (the degree of substitution of 1×Amdex), using 1,3-diaminopropane. In another exemplary aminodextran, the degree of substitution ranges from $1/40$ to $1/7$ using 1,3-diaminopropane. One of skill the art may readily determine the appropriate substitution, taking into consideration the desired effect and/or materials which are readily available.

Aminodextran can be prepared by methods described in U.S. Pat. No. 5,466,609 and U.S. Pat. No. 5,527,713, by periodate oxidation of dextran followed by reaction with 1,3-propanediamine. Of course, the particular method of making the aminodextrans is not limited to such techniques and it is envisioned that any technique for making such aminodextrans are well within the knowledge of those of skill in the art. For example, one of skill in the art may readily substitute a diaminoalkane having two to six carbons for 1,3-propanediamine described in the examples. Preferably, the aminodextran is 5X-Amdex or 1X-Amdex, and most preferably 5X-Amdex.

In the conjugate, the number of biliproteins or tandem dye molecules per dextran will depend upon concentrations of activated species during conjugation, degree of activation of species, size and shape of dextran derivative, and size and shape of biliprotein or tandem dye. A number of linking groups may be employed for conjugating the biliprotein or tandem dye to the dextran. There is ample literature for conjugating phycobiliprotein to proteins. The same methods may be employed where the tandem dye is used in place of the phycobiliprotein in this invention. See, for example, the description of which are incorporated by reference herein. Examples of commercially available cross-linking reagents are disclosed in the Pierce Catalog and Handbook, Life Science and Analytical Research Products, Pierce Chemical Company, Rockford, Ill., 1994/1995. Known linking procedures as described in the above publications may be employed. For example, the phycobiliprotein may be activated with 2-iminothiolane to introduce more thiol groups and conjugated to sulfo-SMCC-activated aminodextran.

The protein-aminodextran conjugates useful in this invention were prepared as described in U.S. Pat. No. 5,527,713, except that two different proteins, one a monoclonal antibody and the other a fluorescent protein (PE) were conjugated simultaneously to the aminodextran (also known as "Amdex"). Preferably, conjugation of antibody and phycobiliprotein to aminodextran is accomplished by activation of PE, activation of antibody, and activation of aminodextran as described herein.

More particularly, an exemplary crosslinked conjugate useful in the present invention was prepared as follows.

(1) a solution of Amdex in distilled water, to which buffer solution was added, was activated with sulfosuccinimidyl 4-[N-maleimidomethyl]cyclohexane-1-carboxylate (sulfo-SMCC) solution in 1×PBS. The mixture was roller mixed for about one hour at room temperature. After the mixing was completed, the reaction mixture was immediately applied to the top of a G-50 Sephadex column equilibrated with 1×PBS. The sample was eluted using 1×PBS and collected in about 2 mL fractions. Fractions of the first band, absorbing at 280 nm, contained the high molecular weight activated Amdex as was verified by Tyndall scatter with a focused visible light beam. These fractions were pooled to give sulfo-SMCC-activated Amdex.

(2) the ligand, i.e., monoclonal antibody, as activated by the addition of a solution of 2-iminothiolane in 1×PBS to antibody concentrate. The resulting solution having an antibody concentration of 15 mg/mL and an iminothiolane-to-antibody molar activation ratio of 15 was mixed at ambient temperature for about one hour. The reaction mixture was then chromatographed on a G-50 Sephadex column equilibrated with 1×PBS and the sample was eluted using 1×PBS. Peak fractions of the first band were collected and pooled.

(3) phycobiliprotein was activated by the addition of a solution of 2-iminothiolane in 1×PBS. The resulting solution having a phycobiliprotein concentration of 40 mg/mL and an iminothiolane-to-phycobieprotein molar activation ratio of 22.5 was mixed at room temperature for about one hour. The reaction mixture was then applied to the top of a G-50 Sephadex column equilibrated with 1×PBS and the sample was eluted with 1×PBS.

(4) iminothiolane-monoclonal antibody solution was first mixed with iminothiolane-phycobiliprotein solution to which a sulfo-SMCC-5X-Amdex solution was subsequently added, or iminothiolane was first added to a sulfo-SMCC-5X-Amdex solution and the iminothiolane monoclonal antibody solution was added immediately afterwards. The entire mixture was then roller mixed overnight for about 16–24 hours. After the mixing was completed, the total volume of each mixture was determined and 0.120 times this volume of 5 mg/mL L-cysteine in 1×PBS was added to the conjugation mixture. The L-cysteine containing mixtures were then mixed for an about 15 minutes to effect blocking of any unreacted sulfo-SMCC moieties. Lastly, iodoacetamide in 1×PBS in the amount of 0.120 times the total mixture volume and 1M borate buffer solution, pH 9.8, in the amount of 0.020 times the total mixture volume were added to the conjugation mixture. The resulting mixture was mixed for about 30 minutes to block any unreacted sulfhydryl groups.

After blocking, the mixture was purified into its components by size exclusion chromatography as follows: the total volume of the conjugation mixture was reduced to about 1.0 to 1.5 mL. The sample was then applied to the top of a Bio-Gel A-5m or A-15m agarose column (2.5 cm×48 cm) equilibrated with 1×PBS and chromatographed using 1×PBS as eluant. Eluant fractions of about 2–4 mL volume were collected. The fractions were monitored at 280 nm. The fractions of the first band collected for the antibody-Amdex-PE conjugate were analyzed spectrophotometrically at 565 and 280 nm using a 1 cm path length cell. The concentration of PE in mg/mL in the conjugate was derived from the absorbance at 565 nm. The active antibody concentration in the conjugate was determined by an ELISA assay and $A_{280}$ g values corrected for absorbance by PE.

D. Methods of the Present Invention

The conjugates may be used in a wide variety of ways. For example, for enhancing known methodologies for the detection, diagnosis, measurement and study of biological materials, including, cells, tissue, organelles, e.g., plasmids, nuclei, etc. Other desirable biological materials include, e.g., amino acids, nucleotide bases, which may be individually labelled (e.g., to permit sequencing), or in the form of oligonucleotides, and the like. The conjugates of the invention are also suitable for detecting antigens, which may be present as individual molecules or in the context of more complex organizations, such as those described above. The conjugates may be used in immunoassays or competitive protein binding assays, where the biliproteins or tandem dyes serve as fluorescent labels.

According to the present invention, a desirable use of the subject conjugates is fluorescentstaining of biological materials. These conjugates may be used as single markers which provide an enhanced signal. For example, the conjugates of the invention are useful in labeling of individual nucleotide bases, thereby enabling enhanced detection of these bases during sequencing in an automatic sequencer. As another example, the enhanced signal makes the conjugates of the invention particularly desirable for detecting non-abundant antigenic sites on cells (e.g., cells having in the range from 10 to 1000 antigenic receptor sites, which would normally show fluorescence intensities close to or obscured by background fluorescence). For example, cells stained with these conjugate markers may then be observed under a microscope, the presence of the fluorescer being diagnostic of the presence of a specific determinant site or the cells may be detected in a fluorescence activated cell sorter (FACS). As described below, the antibodies BB27, BY55 and IL-12 are particularly useful for such applications. The conjugates of the invention are similarly useful for detecting other binding partners which are present on a desired target biological material in low levels.

In another embodiment the conjugates may be used in combinations, where the fluorescence emission maximum of the biliproteins and tandem dyes are separated by at least about 15 nm, preferably by at least about 25 nm. Alternatively, the biliprotein or tandem dye conjugates may be used in conjunction with other protein or non-protein fluorescers, where the emission maxima are separated by at least about 55 nm, preferably about 58 nm.

By using combinations of fluorescers, one can provide for the detection of subsets of aggregations, such as particular types of cells, strains of organisms, strains of viruses, the natural complexing or interaction of different proteins or antigens, etc. In some embodiments, combinations include fluorescein with biliproteins capable of being activated with the same laser light source, e.g., where the biliproteins have absorption maxima in the range of about 450–650 nm.

In a preferred embodiment, the conjugates of the present invention are used in such staining methodologies in tandem with another ligand which is directly and conventionally conjugated with a phycobiliprotein, i.e., not through crosslinking with the aminodextran. The use of these crosslinked antibody-Amdex-(phycobiliprotein or tandem dye) conjugates in this manner is not limited to ligands or antibodies for which the antigenic receptors on white blood cells are few in number, such that fluorescence signals of appropriate magnitude can then be observed above the background fluorescence of cells with the antibody-aminodextran-(phycobiliprotein or tandem dye) markers. Antibodies for which cell surface receptors exist in larger numbers, 1000 per cell and higher, can also be used in the preparation of aminodextran-crosslinked antibody-(phycobiliprotein or tandem dye) conjugates, which can be used according to this invention to further amplify fluorescence intensities of targeted cell populations.

Thus, according to this invention, cell populations may be identified by using one or more pairs of: (a) a conventional, direct antibody-(phycobiliprotein or tandem dye) conjugate prepared with an antibody which binds a cell surface antigenic receptor which is expressed on a first cell subpopulation in about the same or fewer numbers per cell as a second cell surface antigen receptor which is expressed on a second cell subpopulation; and (b) a second Amdex-crosslinked antibody-(phycobiliprotein or tandem dye)

conjugate, prepared with an antibody which binds a second cell surface receptor expressed on the mutually exclusive second subset of blood cells. The combination of these two types of labeled ligands produces two fluorescent-labeled cell populations in mixtures with whole blood with two distinct and non-overlapping fluorescent intensities of the same color emission. Preferably, the intensity difference between the first and second labeled ligands is greater than the intensity difference observed when two direct conjugates are used and separate intensities are observed due to the range of naturally-occurring receptor densities for the first and second cell populations in normal donors. Cells so labeled with a phycobiliprotein or tandem dye may then be observed under a microscope, the presence of the fluorescer being diagnostic of the presence of a specific determinant site or the cells may be detected in a fluorescence-activated cell sorter (FACS).

To extend the number of fluorescence colors that can be obtained with the combination of direct and aminodextran-crosslinked antibody-fluorescent dye conjugates, and thus the numbers of white cell subpopulations that may be identified by this method, additional pairs of ligand (a) and ligand (b) may be used simultaneously employing additional phycobiliproteins, preferably where the fluorescence emission maximum of the biliproteins is separated by at least about 15 nm, and preferably by at least about 25 nm.

The use of the tandem dye molecules, such as PC5 or ECD, that can be excited with the same laser line, 488.0 nm Ar$^+$, as PE, when incorporated into the directly conjugated ligand (a) and crosslinked conjugate (b) offer yet other pairs of markers from the use of only the phycobiliproteins as marker, and thereby provide a method employing three color, two intensity per color, markers.

Alternatively, the fluorescers other than biliproteins, for example fluorescein isothiocyanate (FITC), rhodamine, dansyl and Texas Red, where the emission maxima are separated by at least about 55 nm, preferably about 58 nm, may be used in the method of this invention as a single intensity, additional color marker, directly conjugated to a ligand to provide for additional colors of fluorescence in the method of this invention.

Thus, together with a FITC (excitation, 468–505 nm, emission, 504–541 nm)-labeled ligand (e.g., monoclonal antibody) as an additional color, single intensity marker, there will be available a maximum of seven markers that can be excited simultaneously with a single laser line. This combination of seven markers can further be expanded with the use of two or more laser excitation lines, e.g., 488.0 nm Ar$^+$ and 632.8 nm He/Ne, and additional colordintensities of fluorescent emission from direct antibody-APC (allophycocyanin, excitation, 650 nm, emission, 660 nm)/aminodextran-crosslinked antibody-APC conjugates and markers containing tandem dye conjugates of APC such as APC-Cy7 [M. Roederer et al, *Cytometry*, 24:191–197 (1996)]. Also other protein fluorophores, such as the green fluorescent proteins and blue fluorescent proteins as stated above, may also be employed in these methods [see, e.g., *Handbook of Fluorescent Probes and Research Chemicals*, 6th Ed., R. P. Haugland, Molecular Probes, Inc., Eugene, Oreg., 1996].

Thus, the method of the invention when employed to detect multiple subsets of a cell population in a single-measurement quantification may be summarized as follows:

(A) providing between one to multiple pairs of a desired cell population, the first population of each pair having a first cell surface receptor density which is substantially equivalent to, or less than, the density of a second cell surface receptor on the second population of each pair, the first receptor being found only on the first cell population of each pair, and the second receptor being found only on the second cell population of each pair, wherein the first receptor differs among each first population and the second receptor differs among each second population;

(B) providing for each first population a first ligand labeled directly with a phycobiliprotein or tandem dye, the first ligand capable of binding to the first receptor and differing among each first population; and the phycobiliprotein or tandem dye differing among each first ligand;

(C) providing for each second population a second ligand labeled with an aminodextran-(phycobiliprotein or tandem dye) conjugate, the second ligand capable of binding to the second receptor and differing among each second receptor, wherein within a pair of cell populations the phycobiliprotein or tandem dye of the conjugate is the same as the phycobiliprotein or tandem dye of the first ligand, and wherein the phycobiliprotein or tandem dye of each pair of ligands is a different color;

(D) incubating a biological sample comprising the multiple cell population with each pair of the first and the second labeled ligands for a time sufficient to permit receptor-labeled ligand complexes to form therebetween;

(E) exciting each phycobiliprotein or tandem dye in each complex with a laser excitation line to cause it to fluoresce; and (F) measuring the intensities of fluorescent emissions of each first cell population bound to each labeled first ligand and the fluorescent emissions of each second population bound to each labeled second ligand in a single measurement using flow cytometry; wherein within each pair of cell populations, the first labeled ligand provides a fluorescent signal of the same color but quantitatively distinguishable intensity from that of the second labeled ligand, and wherein the cell populations are distinguished by detectable variations in label intensity and color.

Examples of the use of the method of this invention with single color or multiple colors of markers, e.g., phycobiliproteins or tandem dyes, are provided below. The introduction of multiple colorlintensity immunofluorescence to flow cytometry has several notable advantages. It does not require as much sample; especially important when there is very little sample available, i.e., cell number is low. The cost may be less than larger panel with fewer colors/intensities. The method uses less lyse and quench reagent in preparation of whole blood samples. Less time is required for sample processing; there are fewer tubes to aliquot and handle, and isotype controls may not be needed.

In contrast to the prior art methods disclosed in U.S. Pat. No. 5,538,855, for example, the enhanced fluorescence intensity of crosslinked antibody-dye conjugates over direct antibody-dye conjugates as employed in these methods does not restrict analysis of cell subsets to cell subsets whose intrinsic receptor densities for markers of the same color result in n6n-overlapping fluorescent marker intensities. Rather, two different (or multiple pairs of two different) mutually-exclusive populations of cells with similar intrinsic receptor densities can be analyzed simultaneously with the same color but different intensity of fluorescent markers according to this invention. To avoid overlap of fluorescence intensities of multi-intensity markers of the same color, the intensity difference must be greater than that observed due to the range of naturally-occurring receptor densities for the two targeted blood cell subsets in normal blood donors.

The following examples illustrate various aspects of the present invention. These examples do not limit the scope of the invention, which is embodied in the appended claims.

EXAMPLE 1

Preparation of Purified Antibodies

A. BB27Monoclonal Antibody

BB27 monoclonal antibody, clustered as CD101 in the 5th International Workshop on White Cell Differentiation antigens (*Leukocyte Typing V: White Cell Differentiation Antigens*, eds. Schlossman, S. F., Boumsell, L., Gilks, W., Harlan, J. M., Silverstein, R., Tedder, T. F., and Todd, R. F., (1995), Oxford University Press, Oxford, UK) was obtained by immunization of Balb/c mice with the CD4+CD8+ thymic clone B12. Spleen cells from immunized mice were fused to the NS1 cell line 5 days after the last injection. The initial screening by indirect immunofluorescence and flow cytometry retained all the hybridoma culture supernatants reactive with the immunizing cells but weakly, with the resting PBMC. Cultures containing selected antibodies were cloned twice by limiting dilution [See Gouttefangeas, et al., *Int. Immunol.* 6(3) 423 (1994)]. The cloned hybridoma was injected i.p. into Balb/c mice primed with pristane for ascites production. Antibody was purified from ascites by ammonium sulfate (45%) precipitation, centrifugation and affinity chromatography using protein A-Sepharose. BB27 is an IgG1 monoclonal antibody.

The BB27 antigen is expressed on monocytes, resting or activated granulocytes, and some stromal cell lines. It is also expressed on a subpopulation of peripheral blood T cells (29 per cent) and some T-cell clones. The T-lymphocyte subset defined by BB27 was further found to contain about one third of CD4+ cells and one half of CD8+ cells. In addition, BB27 was expressed on both CD45RA 'naive' and CD45RO 'memory' T-cell subsets.

B. IL-12Rβ.44 Monoclonal Antibody

IL-12Rβ.44 monoclonal antibody is specific for IL12Rβ.44 recognizes the human IL12 receptor β chain. It was obtained by immunization of BALB/c mice with the mouse cell line 300-19 transfected with the human IL12 receptor β chain (IL-12Rβ) and subsequent fusion of spleen cells with NS1 myeloma cells. Hybridomas supernatants were screened by indirect immunofluorescence and flow cytometry using the immunizing transfectant as the positive cell line and the untransfectant parent line 300-19 as a negative control [See Gollob et. al., *J. Immunol.* 157: 1886 (1996)]. Ascites was produced in mice injected i.p. with IL-12Rβ.44 hybridoma. Antibody was purified from ascites by ammonium sulfate precipitation(45%), centrifugation and affinity chromatography using Protein A-Sepharose. The antibody is an IgG1.

The IL12Rβ chain is expressed on activated but not resting T cells and NK cells and on T cell clones [See Desai et. al., *J. Immunol.* 148: 3125 (1992)].

C. BY55 Monoclonal Antibody

The BY55 monoclonal antibody was obtained by immunizing BALB/c mice with the human NK cell line YT2C2 and subsequent fusion with NS1 myeloma cells (See Maiza et al., *J. Exp. Med.* 178: 1121 (1993)]. Hybridoma supernatants were positively screened with the immunizing cells and negatively screened with the T cell clone JF1 and an EBV-transformed B cell line. Cultures containing selected antibodies were cloned twice by limiting dilution. The cloned hybridoma was injected i.p. into Balb/c mice primed with pristane for ascites production. Antibody was purified from ascites fluid by ammonium sulfate precipitation (40%, twice) and size exclusion chromatography on a Sephacryl S300 column. The BY55 antibody is an IgM antibody.

The BY55 antigen is expressed on natural killer (NK) cells, γ/δ T cells and a subpopulation of α/β T cells [See Maiza et. al., *J. Exp. Med.* 178: 1121 (1993)]. They are also found in cord blood and bone marrow cells which are functionally defined as NK cells and NK cells or cytotoxic lymphocytes, respectively [Bensussan et. al., *Proc. Natl. Acad. Sci.* USA. 91, 9136, 1994]. The BY55 antibody was evaluated in the 5th International Workshop on White Cell Differentiation Antigens, (*Leukocyte Typing V: White Cell Differentiation Antigens*, eds. Schlossman, S. F., Boumsell, L., Gilks, W., Harlan, J. M., Silverstein, R., Tedder, T. F., and Todd, R. F., (1995), Oxford University Press, Oxford, UK]

EXAMPLE 2

Preparation of Antibody-PE Conjugate

Conjugation of IgG or IgM monoclonal antibody to PE was accomplished by 2-iminothiolane (IT) activation of PE and sulfosuccinimidyl 4-[N-maleimidomethyl] cyclohexane-1-carboxylate (sulfo-SMCC) activation of antibody as follows:

A. Activation of Monoclonal Antibody with Sulfo-SMCC.

For 20 mg of monoclonal antibody at a concentration of 36 mg/mL, 0.555 mL of monoclonal antibody concentrate were required. A 20 mg/mL solution of sulfo-SMCC in distilled water was prepared and used at an activation ratio of sulfo-SMCC: monoclonal antibody=15:1. Thus, to make a total volume of 1.000 mL, 0.100 mL of 1M phosphate buffer, 1M sodium chloride, pH 7.4 was mixed with 0.304 mL 1×PBS buffer, to which were added 0.555 mL of monoclonal antibody solution with stirring at room temperature and then slowly added 0.041 mL of sulfo-SMCC solution. The reaction mixture in a 15 mL tube was roller mixed at room temperature for 60 min and then, immediately applied to the top of a 30 mL G-50 Sephadex column, equilibrated with 1×Bis-Tris buffer (0.1M Bis-Tris, 0.1M sodium chloride, pH 5.55, pH adjusted with glacial acetic acid). The activated monoclonal antibody was eluted from the column with 1×Bis-Tris buffer and fractions of the first peak absorbing at 280 nm were collected. The sulfo-SMCC-monoclonal antibody concentration in mg/mL was determined by the $A_{280}$ value. The activated monoclonal antibody solution was diluted or concentrated to 2 mg/mL with Bis-Tris buffer.

B. Activation of PE with 2-Iminothiolane

PE, R-phycoerythrin (red algae), obtained as a 60% ammonium sulfate suspension in 50 mM sodium phosphate, pH 7.0 buffer from Prozyme, Inc. (San Leandro, Calif.), was applied to a G-50 Sephadex column equilibrated with 50 mM phosphate, 2 mM EDTA, pH 7.0 buffer, eluted with the latter buffer, and then concentrated. For 34 mg of PE at a concentration of 74.38 mg/mL in 50 mM phosphate, 2 mM EDTA, pH 7.0 buffer, 0.457 mL of the PE concentrate were required. A 6 mg/mL solution of 2-iminothiolane hydrochloride (IT) was prepared and used at an activation ratio of IT: PE=15.7:1. Thus, to make a total volume of 0.850 mL, 0.085 mL of 1M phosphate buffer was mixed with 0.257 mL of 1×PE column buffer (0.1M phosphate, 0.1M sodium chloride, 0.1% sodium azide, 0.1 mM EDTA), to which were added 0.457 mL of PE solution with stirring at room temperature and then, slowly added 0.051 mL of IT solution. The reaction mixture in a 15 mL tube was roller mixed for 60 min, and then immediately loaded onto a 25 mL G-50 Sephadex column, equilibrated with Bis-Tris buffer. The activated PE was eluted from the column with 1×Bis-Tris buffer and the first peak off the column was collected. The concentration in mg/mL of activated PE was determined as $A_{565}/8.167$. The activated PE was diluted or concentrated to 3 mg/mL with 1×Bis-Tris buffer.

C. Conjugation of Sulfo-SMCC-monoclonal Antibody with Iminothiolane-PE

For conjugation, equal volumes (9.0 mL) of activated monoclonal antibody at 2 mg/mL and activated PE at 3 mg/mL were mixed by adding activated monoclonal antibody into stirring activated PE, and then adding 0.360 mL of 1M phosphate buffer. The reaction mixture was roller mixed at room temperature for 1 hour. At the end of the mixing period, 0.918 mL of 25 mg/mL L-cysteine in DW were further added to the reaction mixture, which was roller mixed for an additional 15 min.

D. Purification of Monoclonal Antibody-PE Conjugate

A Bio-Gel A 1.5 m column (10mL of column per mg of monoclonal antibody or 200 mL) equilibrated with 1×PE column buffer was prepared. The sample was loaded onto the Bio-Gel A1.5 m column, and eluted with 1×PE column buffer. The $A_{280}/A_{565}$ ratio was calculated for each fraction. All fractions with ratios from 0.43 until two fractions before the free PE eluates were pooled. For example, the pooled BB27-PE fractions were concentrated to a volume of 1.73 mL, less than 1% of the column volume, by using an Amicon YM30 membrane, diafiltering the concentrate with 1×PBS, 0.1% sodium azide, 1 mM EDTA buffer, and centrifuging the BB27-PE conjugate at 1800×g for 15 min at 4° C. A 50-fold dilution of this pooled sample gave $A_{565}$=0.6820 or (/8.167)×50=4.18 mg/mL PE and 7.22 mg total PE in the BB27-PE conjugate, and $A_{280}$=0.1883 or [0.6820/5.60 (PE's $A_{565}/A_{280}$)] 50=3.33 mg/mL BB27 and 5.75 mg total BB27 in the BB27-PE conjugate. The molar ratio of PE/BB27 is therefore (7.22 mg PE/ 240,000)//(5.75 mg BB27/160,000)= 0.837. A corrected F/P ratio based on the formula, [$A_{280}/A_{565}$ (conjugate)−$A_{280}/A_{565}$ (dye)]×8.77, is 0.855.

Similar methods were used to prepare IL-12R-PE and BY55-PE conjugates having F/P ratios of 0.614 and 0.577, and corrected E/P ratios of 0.967 and 0.862, respectively.

EXAMPLE 3

Preparation of Antibody-Aminodextran-PE Conjugates

The procedure was similar to the one used in U.S. Pat. No. 5,527,713 issued Jun. 18, 1996, to prepare conjugates of anti-CD3 antibody with aminodextran, either 1X-Amdex or 5X-Amdex. However, in the present work two different proteins, one, a monoclonal antibody and the other, a fluorescent protein, were conjugated simultaneously to the aminodextran. Trials with total protein, BB27 and PE, to 5X-Amdex weight ratios of 3:1 and about 1:1, and an antibody:5X-Amdex weight ratio of 1:2 were carried out.

A. Activation of Aminodextran with Sulfo-SMCC 0.667 mL of a 10 mg/mL solution of 5X-Amdex in distilled water, to which 0.033 mL of 20×PBS buffer solution were added to make a 1×PBS solution, was activated with 0.120 mL of 10 mg/mL sulfo-SMCC solution in 1×PBS. The mixture was roller mixed for about one hour at room temperature. After the mixing was completed, the reaction mixture was immediately applied to the top of a 25 mL G-50 Sephadex column equilibrated with 1×PBS. The sample was eluted using 1×PBS and collected in about 2 mL fractions. Fractions of the first band absorbing at 280 nm contained the high molecular weight activated 5X-Amdex as was verified by Tyndall scatter with a focused visible light beam(Model 650, Cambridge Instruments, Inc., Buffalo, N.Y.). These fractions were pooled to give about 3.5 mL total sulfo-SMCC-activated 5X-Amdex, 1.75 mL used in each of two trials.

B. Activation of Antibody

BB27 monoclonal antibody as prepared above was activated by the addition of 0.065 mL of a 2 mg/mL solution of iminothiolane in 1×PBS and 0.324 mL 1×PBS to 0.278 mL of BB27 concentrate (36.00 mg/mL). The resulting solution which had an antibody concentration of 15 mg/mL and an iminothiolane molar activation ratio of 15 was mixed at ambient temperature for about one hour. The reaction mixture was then chromatographed on a 20 mL G-50 Sephadex column equilibrated with 1×PBS and the sample was eluted using 1×PBS. The first band peak fraction yielded about 2.5 mL of 3.519 mg/mL antibody solution which contained a total of 8.797 mg IT-BB27 antibody derivative.

C. Activation of PE

PE, R-phycoerythrin (red algae) from Prozyme, Inc., the 60% ammonium sulfate removed by buffer exchange by elution on a G-50 Sephadex column equilibrated with 50 mM phosphate, 2mM EDTA, pH 7.0, and concentrated, was then activated by the addition of 0.097 mL of a 2 mg/mL solution of iminothiolane in 1×PBS and 0.089 mL 1×PBS to 0.189 mL of PE concentrate (79.27 mg/mL). The resulting solution which had a PE concentration of 40 mg/mL and an iminothiolane molar activation ratio of 22.5 was mixed at room temperature for about one hour. The reaction mixture was then applied to the top of a 20 mL G-50 Sephadex column equilibrated with 1×PBS and the sample was eluted with 1×PBS. The first band peak fraction gave about 3.8 mL of 2.523 mg/mL PE at an $A_{565}/A_{280}$ ratio of 5.0338, which contained a total of 9.587 mg IT-PE.

D. Conjugation of IT-BB27 and IT-PE to Sulfo-SMCC-5X-Amdex (1) Trial 1–10 mg total protein: 3.333 mg 5X-Amdex 0.406 mL of 3.519 mg/mL IT-BB27 solution (about 1.429 mg antibody) were first mixed with 3.397 mL of 2.523 mg/mL IT-PE solution (about 8.571 mg PE), to Which were added 1.750 mL of sulfo-SMCC-5X-Amdex solution (about 3.333 mg 5X-Amdex) and the entire mixture was roller mixed overnight for 16–24 hours.

(2) Trial 2–3 mg total protein: 3.333 mg 5X-Amdex In a similar way, 0.430 mL of 3.519 mg/mL IT-BB27 solution (about 1.5138 mg antibody) were first mixed with 0.600 mL IT-PE solution (about 1.5138 mg PE), to which were added 1.750 mL of sulfo-SMCC-5X-Amdex solution(about 3.333 mg 5X-Amdex) and the entire mixture was roller mixed overnight for 16–24 hours.

After the mixing was completed, the total volume of each mixture was determined and 0.120 times this volume of 5 mg/mL L-cysteine in 1×PBS was added to each conjugation mixture. The L-cysteine containing mixtures were then mixed for an additional 15 minutes to effect blocking of any unreacted sulfo-SMCC moieties. Lastly, 20 mg/mL iodoacetaraide in 1×PBS in the amount of 0.120 times the total mixture volume and 1M borate buffer solution, pH 9.8, in the amount of 0.020 times the total mixture volume were added to each mixture. The resulting mixtures were mixed for about 30 minutes to block any unreacted sulfhydryl groups.

E. Purification of BB27-5X-Amdex-PE Conjugates.

The total volume of trial 1 conjugation mixture was reduced to about 1.5 mL by centrifuging an Amicon Centri-Prep 30 tube containing the sample for about 20 minutes at 2000 rpm using a refrigerated Beckman J-6B centrifuge. Trial 2 conjugation mixture was used without concentration at about 2.9 mL. The samples were placed on the top of a Bio-Gel A-5 m agarose column (2.5 cm×48 cm) equilibrated with 1×PBS and chromatographed using 1×PBS as eluant. Eluant fractions of about 4 mL volume were collected using a Pharmacia LKB FRAC-100 collector operating in the drop collection mode. The fractions were monitored using a LKB 2138 Uvicord S monitor operating at 280 nm. In trial 1, the first narrow, intense band eluted from the column contained the BB27-aminodextran-PE conjugate. A lower intensity shoulder of less than one-third the intensity of the first peak in trial 1 contained excess PE. A medium-to-low intensity well-separated third band was attributed to low molecular weight excess blocking reagents. Trial 2 did not show the narrow and intense first band but only an initial broad shoulder on the second band containing excess PE.

The fractions collected for the BB27-5X-Amdex-PE conjugate were analyzed spectrophotometrically at 565 and 280 nm using a 1 cm path length cell. The concentration of PE in mg/mL in the conjugate was derived from the absorbance at 565 nm by using the formula, $A_{565}/8.167$. The active BB27 antibody concentration in the conjugate was determined by an ELISA assay for IgG1 antibody. Data for fractions 21 to 25 under the first narrow peak in trial 1 are listed in Table 2. In trial 2, seven fractions containing the most PE were pooled and concentrated to give the data shown in Table 2.

TABLE 2

| Fraction | $A_{565}$ | $A_{280}$ | $A_{565}/A_{280}$ | PE, mg/mL | BB27, µg/mL |
|---|---|---|---|---|---|
| 21 | 1.096 | 0.276 | 3.96 | 0.134 | 1.32 |
| 22 | 2.437 | 0.581 | 4.19 | 0.298 | 3.75 |
| 23 | 2.081 | 0.472 | 4.41 | 0.255 | 3.64 |
| 24 | 1.315 | 0.282 | 4.66 | 0.161 | 1.90 |
| 25 | 0.907 | 0.188 | 4.82 | 0.111 | 1.70 |
| trial 2 | 1.745 | 0.492 | 3.55 | 0.214 | 43.8 |

EXAMPLE 4

Preparation of BB27-1X-Amdex-PE Conjugate.

The activation, conjugation, blocking, and chromatography procedures were the same as those described above for trial 1, BB27-5X-Amdex-PE conjugate. The concentrations of IT-PE (8.571 mg), IT-BB27 (1.429 mg), and sulfo-SMCC-1X-Amdex (3.333 mg) during conjugation were 0.973, 0.162, and 0.386 mg/mL, respectively. This time six fractions of the first narrow peak were analyzed at 565 and 280 nm using a 1 cm path length cell. The IT-PE ($A_{565}/A_{280}$) ratio was 5.356. Absorbance and concentration data for the six fractions are shown in Table 3.

TABLE 3

| Fraction | $A_{565}$ | $A_{280}$ | $A_{565}/A_{280}$ | PE, mg/mL |
|---|---|---|---|---|
| 19 | 0.329 | 0.080 | 4.14 | 0.040 |
| 20 | 1.072 | 0.241 | 4.45 | 0.131 |
| 21 | 1.423 | 0.313 | 4.55 | 0.174 |
| 22 | 1.258 | 0.267 | 4.70 | 0.154 |
| 23 | 1.023 | 0.209 | 4.89 | 0.125 |
| 24 | 0.863 | 0.172 | 5.01 | 0.106 |

EXAMPLE 5

Preparation of BB27-5X-Amdex-PE Conjugates Using Column Buffer instead of 1×PBS for PE Conjugate Purification and Storage The procedures were the same as those described above for trial 1, BB27-5X-Amdex-PE conjugate, except purification of the final conjugate was carried out on a Bio-Gel A-5 m agarose column equilibrated with column buffer, consisting of 1×PBS, 0.1 mM EDTA, 1 mM iodoacetamide, pH 7.2, and chromatographed with the same column buffer as eluant. In trial 3, the same amounts of IT-PE (8.571 mg), IT-BB27 (1.429 mg) were mixed with sulfo-SMCC-5X-Amdex (3.333 mg), as in trial 1, at concentrations of 2.23, 0.373, and 0.869 mg/mL, respectively, during conjugation. In trial 4, the same amounts of IT-PE, IT-BB27 as in trial 1, but 2× the amount of sulfo-SMCC-5X-Amdex (6.666 mg) were used at concentrations of 1.65, 0.275, and 1.28 mg/mL, respectively, during conjugation. The IT-PE($A_{565}/A_{280}$) ratio was 5.790. Data for fractions collected under the first narrow peak in trials 3 and 4 are listed in Table 4.

TABLE 4

| Fraction | $A_{565}$ | $A_{280}$ | $A_{565}/A_{280}$ | PE, mg/mL | BB27, µg/mL |
|---|---|---|---|---|---|
| trial 3 | | | | | |
| 19 | 0.728 | 0.377 | 1.93 | 0.089 | 1.47 |
| 20 | 1.382 | 0.511 | 2.70 | 0.169 | 3.83 |
| 21 | 1.006 | 0.421 | 2.39 | 0.123 | 3.15 |
| 22 | 0.684 | 0.350 | 1.95 | 0.084 | 1.86 |
| trial 4 | | | | | |
| 20 | 1.043 | 0.441 | 2.37 | 0.128 | 2.11 |
| 21 | 0.986 | 0.425 | 2.32 | 0.121 | 2.76 |
| 22 | 0.765 | 0.374 | 2.04 | 0.094 | 1.50 |

EXAMPLE 6

Analyses for IgG1 and IgM Antibodies by ELISA

Following the method described in Enzyme-Immunoassay, E. T. Maggio, CRC Press, Boca Raton, Fla., 1985, pp 181–196, microtiter plates (Corning modified flat bottom ELISA plates) were coated with 100 µL of affinity-purified goat anti-mouse IgG1 or IgM (Southern Biotechnology Associates, Inc.), diluted to 0.6 µg/mL in 0.2M carbonate buffer, pH 9.6, overnight at 4° C. After washing with 1×PBS, pH 7.2, containing 0.05% Tween 20, the plates were saturated with PBS containing 1% BSA and incubated for 90 min at room temperature. Dilutions of antibody-5X-Amdex-PE conjugate samples were made in 1% BSA/PBS and 100 µL of each were added to the plate, which was then incubated for one hour at room temperature. Dilutions of the IgG1 and IgM antibody standards between 7.8 and 250 ng/mL, and 15.6 and 500 ng/mL, respectively, were used for calibration curves. After washing the plates, 100 µL of horseradish peroxidase(HRP)-conjugated goat anti-mouse Ig (Cappel), diluted in PBS were added and incubated for one hour at room temperature. The plates were washed and reactions were revealed by the addition of 200 µL of ABTS, 2,2'-azino-bis(3-ethylbenzthiazoline-6-sulfonic acid (Sigma), at 0.2 mg/mL in 0.2M sodium citrate buffer, pH 4.0, and 0.02% hydrogen peroxide. After a one hour incubation at room temperature, the plates were read on a V MAX microplate reader (Molecular Devices) at 405 nm using 490 nm as a reference wavelength Semi-log plots of absorbance versus concentration were used to prepare IgG1 and IgM antibody standard linear regression curves. The antibody concentration in the samples was calculated by using absorbance values in the linear range of the standard curve.

EXAMPLE 7

Estimation of Molecular Weights of Antibody-Aminodextran-PE Conjugates

A mixture of gel filtration standards (Bio-Rad) or molecular weight markers (Sigma) and blue dextran (T-2M) was applied to the same A-5 m column that was used to purify the antibody-aminodextran-PE conjugates, eluted from the column with 1×PBS, monitored by $A_{280}$, and collected at the same drop count of 120 drops/fraction or about 4 mL/fraction. The curve obtained, when the logarithm of the molecular weights of the standards was plotted against the respective ratios of elution volume ($V_c$) to column void volume ($V_o$), was used by interpolation to estimate the molecular weights of antibody-aminodextran-PE conjugates. The void volume was determined from the position of antibody aggregates in the elution profile. The results are shown in Table 5 for standards and conjugates collected in fractions 20 to 25, together with an upper limit on the PE/aminodextran molar ratio assuming PE (MW 240,000 daltons) were the only protein in the conjugate and 5X-Amdex with a MW of 350,000 daltons. In addition, fractions between 35 and 40, collected as a shoulder to the main band and showing some PE absorbance at 565 nm, are estimated from the semilog plot of molecular weight versus $V_c/V_o$ to contain species of molecular weight, 480,000 to 195,000 daltons, which are assigned to to either excess PE or to a 1:1 PE:aminodextran conjugate.

TABLE 5

|  | $V_c/V_o$ | MW, daltons |
|---|---|---|
| blue dextran | 1.04 | ~2,000,000 |
| thyroglobulin | 1.69 | 670,000 |
| IgG | 2.15 | 158,000 |
| ovalbumin | 2.41 | 44,000 |
| myoglobin | 2.61 | 17,000 |
| vitamin B-12 | 3.00 | 1,350 |

| Fraction | | | PE/aminodextran |
|---|---|---|---|
| 20 | 1.026 | 2,000,000 | 6.9 |
| 21 | 1.077 | 1,850,000 | 6.3 |
| 22 | 1.128 | 1,750,000 | 5.8 |
| 23 | 1.179 | 1,650,000 | 5.4 |
| 24 | 1.231 | 1,500,000 | 4.8 |
| 25 | 1.282 | 1,400,000 | 4.4 |
| 30 | 1.54 | 920,000 | |
| 35 | 1.79 | 480,000 | |
| 40 | 2.05 | 195,000 | |

EXAMPLE 8

Preparation of Anti-IL-12Rβ.44-5X-Aminodextran-PE Conjugates

The procedures were the same as those outlined for the preparation of the BB27-5X-Amdex-PE conjugate in trial 3 of Example 3, except anti-IL 12R antibody, also of the IgG1 class, was activated with IT and used in the conjugation instead of BB27 antibody. In trial 4, IT-PE (8.571 mg), IT-IL-12Rβ.44 (1.429 mg) were mixed with sulfo-SMCC-5X-Amdex (3.333 mg) at concentrations of 1.67, 0.279, and 0.651 mg/mL, respectively, during conjugation. In trial 5, the same amounts of reactants as in trial 4 were used, but 2× activation of 5X-Amdex with sulfo-SMCC was carried out, i.e., 0.120 mL of 10 mg/mL sulfo-SMCC solution in 1×PBS for 3.333 mg of 5X-Amdex. Concentrations of reactants during conjugation in trial 6 were 1.07, 0.178, and 0.415 mg/mL, respectively. The IT-PE ($A_{565}/A_{280}$) ratio was 5.866. Data for fractions collected under the first narrow peak in trials 5 and 6 are listed in Table 6.

TABLE 6

| Fraction | $A_{565}$ | $A_{280}$ | $A_{565}/A_{280}$ | PE, mg/mL | IL-12Rβ.44, μg/mL |
|---|---|---|---|---|---|
| trial 5 | | | | | |
| 20 | 1.015 | 0.428 | 2.37 | 0.124 | 1.55 |
| 21 | 2.178 | 0.677 | 3.22 | 0.267 | 4.55 |
| 22 | 1.630 | 0.549 | 2.97 | 0.200 | 4.15 |
| 23 | 0.992 | 0.410 | 2.42 | 0.121 | 1.98 |
| 24 | 0.721 | 0.351 | 2.06 | 0.088 | 1.79 |
| trial 6 | | | | | |
| 21 | 0.803 | 0.355 | 2.26 | 0.098 | 1.90 |
| 22 | 0.813 | 0.356 | 2.29 | 0.100 | 2.25 |
| 23 | 0.687 | 0.323 | 2.13 | 0.084 | 1.54 |

EXAMPLE 9

Preparation of Anti-BY55 Antibody-5X-Aminodextran-PE Conjugates

The procedures were the same as those outlined for the BB27-5X-Amdex-PE conjugate in trial 3 of Example 3, except BY55 antibody of the IgM class was activated with IT and used in the conjugation instead of BB27 antibody. In trial 7, the same amounts of reactants, IT-PE (8.571 mg), IT-BY55 (1.429 mg) were mixed with sulfo-SMCC-5X-Armdex (3.333 mg) at concentrations of 2.14, 0.357, and 0.833 mg/mL, respectively, during conjugation. In trial 8, 2× the usual amount of antibody was used so that reactants, IT-PE (8.571 mg), IT-BY55 (2.858 mg) were mixed with sulfo-SMCC-5X-Amdex (3.333 mg) at concentrations of 1.91, 0.637, and 0.743 mg/mL, respectively, during conjugation. The IT-PE ($A_{565}/A_{280}$) ratio was 5.800. Data for fractions collected under the first narrow peak in trials 7 and 8 are listed in Table 7.

TABLE 7

| Fraction | $A_{565}$ | $A_{280}$ | $A_{565}/A_{280}$ | PE, mg/mL | BY55, μg/mL |
|---|---|---|---|---|---|
| trial 7 | | | | | |
| 20 | 1.338 | 0.549 | 2.44 | 0.164 | 3.43 |
| 21 | 2.506 | 0.817 | 3.07 | 0.307 | 7.50 |
| 22 | 1.596 | 0.541 | 2.95 | 0.195 | 4.78 |
| 23 | 0.874 | 0.363 | 2.41 | 0.107 | 3.10 |
| trial 8 | | | | | |
| 19 | 1.352 | 0.753 | 1.79 | 0.165 | 11.6 |
| 20 | 3.096 | 1.246 | 2.49 | 0.379 | 31.7 |
| 21 | 2.111 | 0.880 | 2.40 | 0.258 | 17.8 |
| 22 | 1.024 | 0.556 | 1.84 | 0.125 | 6.40 |

EXAMPLE 10

Flow Cytometric Analyses of Whole Blood with BB27-PE and BB27-aminodextran-PE Conjugates BB27-PE and fractions of BB27-aminodextran-PE conjugates were titered, starting at either 2 μg or 1 μg per tube (in a 10 μl volume). Dilutions were added to 100 μl of whole blood and incubated for 1 hour at room temperature. Blood was lysed on a COULTER® Q-Prep (Coulter Corporation, Miami, Fla.), washed once with PBS and run on a flow cytometer (COULTER XL). When gated on the lymphocyte population, typical histograms show low PE mean channel fluorescence an intensities close to the discriminator line for the labeled T cells because of the low BB27 receptor density (<1000 per cell) on the surface of the cells.

Figure 1B:
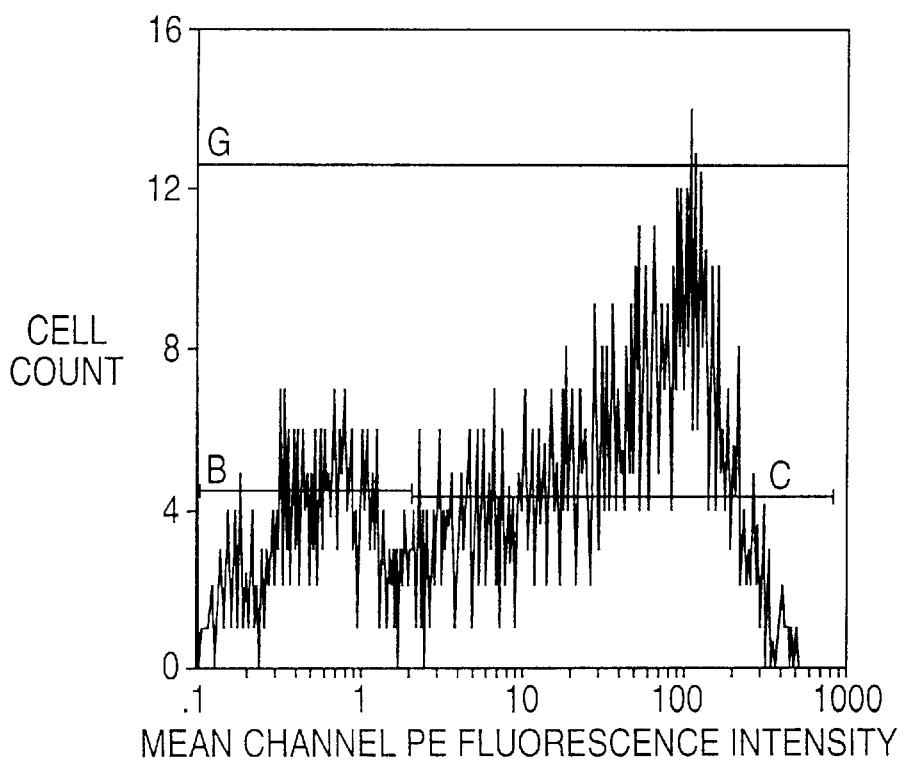
Figure 2A:
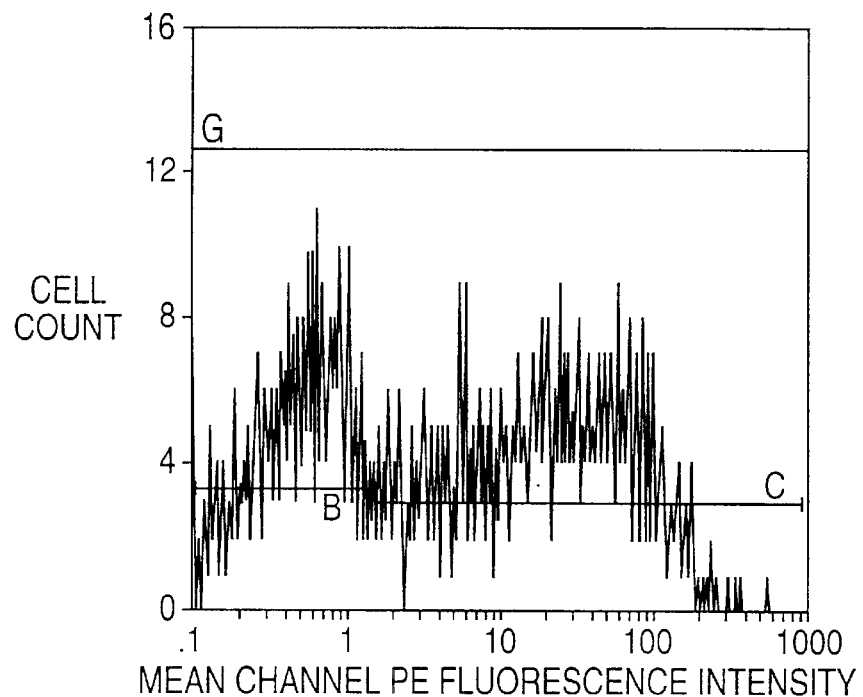
FIGS. 2A and 2B show histograms for lymphocytes in whole blood, either unblocked or blocked with free anti BB27 antibody, prior to mixing crosslinked conjugate BB27-5X-Amdex-PE with whole blood.
Figure 2B:
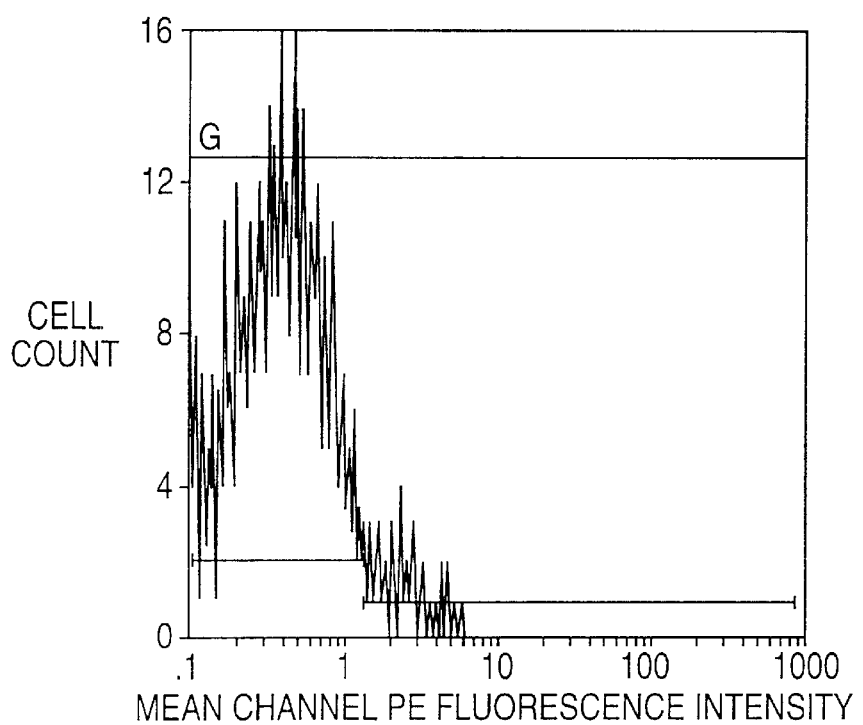

The utility of the BB27-5X-Amdex-PE conjugate as a marker containing more than two PE molecules per dextran molecule, compared to the direct BB27-PE conjugate which contains 0.85 PE molecule per antibody molecule, is shown in the histograms displayed in FIGS. 1A and 1B. FIGS. 1A and 1B show staining of scatter gated lymphocytes with BB27 antibody. 100 μl of whole blood from a normal donor was stained 10 μl containing 0.25 μg of BB27 antibody as (A) BB27-PE or (B) BB27-5X-Amdex-PE. FIGS. 1A and 1B shows that the crosslinked conjugate has 10-fold higher fluorescence intensity on BB27+ lymphocytes. Herein, the mean channel fluorescence intensity of labeled T cells could be enhanced up to 8-fold by using various fractions of trial 1, BB27-5X-Amdex-PE conjugate as the fluorescent marker. The effect of blocking BB27 receptor sites on targeted lymphocytes in whole blood with purified, unlabeled BB27 antibody (750 μg/ml) before using the BB27-5X-Amdex-PE marker is shown in the cell count versus PE fluorescent intensity histograms of FIGS. 2A and 2B. FIGS. 2A and 2B show staining of scatter gated lymphocytes with BB27 antibody. 100 μL of whole blood from a normal donor was stained with (FIG. 2A) 10 μL containing 0.25 μg of BB 27 antibody in the form of BB27-5X-Amdex-PE or (FIG. 2B) BB27-5X-Amdex-PE, after blocking with an excess (750 μg/mL) of unlabeled BB27. FIGS. 2A and 2B shows that the conjugate is specific for the BB27 antigen. Titers of the control, BB27-PE, and the sample, BB27-5X-Amdex-PE, with whole blood were run with two blood donors. Mean channel PE fluorescence intensities and sample intensities relative to the control, obtained with the same instrument settings, are listed in Tables 8 and 9.

TABLE 8

| BB27, μg | Control | Fraction 22 | Fraction 23 | Fraction 24 | Fraction 25 |
|---|---|---|---|---|---|
| Donor 1 | | | | | |
| Mean Channel PE Fluorescence Intensities | | | | | |
| 2 | 14.2 | 73.6 | 53.0 | 54.5 | 39.3 |
| 1 | 12.8 | 71.6 | 53.1 | 48.5 | 39.6 |
| 0.5 | 11.7 | 77.2 | 60.8 | 42.2 | 41.1 |
| 0.25 | 10.4 | 78.6 | 56.8 | 48.1 | 43.4 |
| 0.125 | 10.2 | 74.7 | 65.4 | 45.5 | 50.2 |
| 0.0625 | 8.46 | 57.1 | — | 50.2 | 57.3 |
| 0.031 | 9.06 | 43.6 | 50.4 | 50.4 | 57.0 |
| MFI Ratios, Fraction/Control | | | | | |
| 2 | 1.0 | 5.2 | 3.7 | 3.8 | 2.8 |
| 1 | 1.0 | 5.6 | 4.1 | 3.8 | 3.1 |
| 0.5 | 1.0 | 6.6 | 5.2 | 3.6 | 3.5 |
| 0.25 | 1.0 | 7.6 | 5.5 | 4.6 | 4.2 |
| 0.125 | 1.0 | 7.3 | 6.4 | 4.5 | 4.9 |
| 0.0625 | 1.0 | 6.7 | — | 5.9 | 6.8 |
| 0.031 | 1.0 | 4.8 | 5.6 | 5.6 | 6.3 |

TABLE 9

| BB27, μg | Control | Fraction 22 | Fraction 23 | Fraction 24 | Fraction 25 |
|---|---|---|---|---|---|
| Donor 2 | | | | | |
| Mean Channel PE Fluorescence Intensities | | | | | |
| 2 | 12.6 | 68.3 | 57.2 | 51.4 | 42.1 |
| 1 | 12.1 | 53.5 | 46.4 | 51.4 | 36.1 |
| 0.5 | 10.9 | 44.0 | 42.1 | 44.6 | 29.1 |
| 0.25 | 8.25 | 40.1 | 38.2 | 36.4 | 27.2 |
| 0.125 | 7.47 | 43.5 | 31.6 | 30.0 | 25.5 |

TABLE 9-continued

| BB27, μg | Control | Fraction 22 | Fraction 23 | Fraction 24 | Fraction 25 |
|---|---|---|---|---|---|
| Donor 2 | | | | | |
| 0.0625 | 7.96 | 37.8 | 28.4 | 27.7 | 19.5 |
| 0.031 | 6.90 | 28.5 | 31.4 | 23.6 | 20.6 |
| MFI Ratios, Fraction/Control | | | | | |
| 2 | 1.0 | 5.4 | 4.5 | 4.1 | 3.3 |
| 1 | 1.0 | 4.4 | 3.8 | 4.2 | 3.0 |
| 0.5 | 1.0 | 4.0 | 3.9 | 4.1 | 2.7 |
| 0.25 | 1.0 | 4.9 | 4.6 | 4.4 | 3.3 |
| 0.125 | 1.0 | 5.8 | 4.2 | 4.0 | 3.4 |
| 0.0625 | 1.0 | 4.7 | 3.6 | 3.5 | 2.4 |
| 0.031 | 1.0 | 4.1 | 4.6 | 3.4 | 3.0 |

As shown in tables 8 and 9, the antibody-aminodextran-phycoerythrin conjugates enhanced the fluorescence intensity of labeled T cells from 2 to 8-fold.

Data from the first donor were also used to evaluate fluorescence equivalent units (FEUs) by using COULTER Flow-Cal 575 beads, i.e., PE standard beads, to place the PE intensities on an absolute intensity scale. The 0.25 μg BB27 titers in the fluorescence intensity plateau region representing saturation of receptor sites for the four sample fractions and the 2 μg BB27 titer representing maximum fluorescence intensity for the control were used. Data are compiled in Table 10 and used to calculate normalized FEUs and the number of PE molecules per molecule of dextran, knowing the PE per antibody in the direct BB27-PE conjugate and assuming PE fluorescence is not quenched by any interaction between PE molecules in the conjugate in which BB27 antibody and PE are crosslinked by dextran.

TABLE 10

| Sample | FEU units | FEU, normalized | PE/dextran or antibody |
|---|---|---|---|
| Fraction 22 | 117,093 | 5.641 | 4.8 |
| Fraction 23 | 90,500 | 4.360 | 3.7 |
| Fraction 24 | 71,526 | 3.446 | 2.9 |
| Fraction 25 | 64,355 | 3.100 | 2.7 |
| Control | 20,756 | 1.000 | 0.855 |

Note that the enhancement factors in the normalized FEU column represent a lower bound, assuming that the dextran crosslinked BB27-PE conjugate occupies a single receptor site like the direct BB27-PE conjugate. The difference between PE/dextran ratios for fractions 22 to 25 in Table 10 and the upper bound ratios for the same fractions in Table 5 gives an estimated one or two BB27 antibody/dextran ratio. Based on one or two BB27/dextran, the PE/dextran ratios at saturation, and the PE concentrations from Table 2, the calculated BB27 antibody concentrations are up to ten-fold higher than the BB27 concentrations determined by ELISA and shown in Table 2.

Similar flow cytometric data were obtained for the control, BB27-PE, and six fractions of BB27-1X-Amdex-PE, and are summarized in Tables 11 and 12.

TABLE 11

Donor 1

| BB27, μg | Control | Fraction 19 | Fraction 20 | Fraction 21 | Fraction 22 | Fraction 23 | Fraction 24 |
|---|---|---|---|---|---|---|---|
| Mean Channel PE Fluorescence Intensities | | | | | | | |
| 1 | 12.7 | 25.1 | 28.5 | 29.4 | 27.2 | 22.7 | 21.8 |
| 0.5 | 11.2 | 29.7 | 24.8 | 24.8 | 20.5 | 26.2 | 20.6 |
| 0.25 | 10.2 | 23.7 | 11.0 | 13.9 | 19.1 | 21.2 | 16.4 |
| 0.125 | 7.7 | 21.4 | 6.3 | — | 17.3 | — | 13.7 |
| 0.0625 | 6.6 | 15.9 | 4.9 | 11.6 | 12.9 | 20.2 | 11.6 |
| 0.031 | 6.2 | 11.4 | 5.3 | 8.9 | 10.3 | 13.4 | 11.4 |
| MFI Ratios, Fraction/Control | | | | | | | |
| 1 | 1.0 | 2.0 | 2.2 | 2.3 | 2.1 | 1.8 | 1.7 |
| 0.5 | 1.0 | 2.6 | 2.2 | 2.2 | 1.8 | 2.3 | 1.8 |
| 0.25 | 1.0 | 2.3 | 1.1 | 1.4 | 1.9 | 2.1 | 1.6 |
| 0.125 | 1.0 | 2.8 | 0.8 | — | 2.2 | — | 1.8 |
| 0.0625 | 1.0 | 2.4 | 0.7 | 1.8 | 2.0 | 3.1 | 1.8 |
| 0.031 | 1.0 | 1.8 | 0.9 | 1.4 | 1.7 | 2.2 | 1.8 |

TABLE 12

Donor 2

| BB27, μg | Control | Fraction 19 | Fraction 20 | Fraction 21 | Fraction 22 | Fraction 23 | Fraction 24 |
|---|---|---|---|---|---|---|---|
| Mean Channel PE Fluorescence Intensities | | | | | | | |
| 1 | 10.6 | 24.5 | 27.8 | 25.9 | 21.3 | 18.7 | 19.8 |
| 0.5 | 8.1 | 21.6 | 21.2 | 18.9 | 17.6 | 20.3 | 18.8 |
| 0.25 | 9.1 | 19.4 | 19.7 | 17.2 | 18.1 | 19.4 | 14.9 |
| 0.125 | 7.9 | 19.8 | 16.6 | 14.5 | 13.4 | 15.8 | 14.8 |
| 0.0625 | 6.8 | 12.3 | 11.8 | 13.7 | 12.1 | 12.4 | 12.6 |
| 0.031 | 5.7 | 9.6 | 9.4 | 11.0 | 10.8 | 13.5 | 9.8 |
| MFI Ratios, Fraction/Control | | | | | | | |
| 1 | 1.0 | 2.3 | 2.6 | 2.4 | 2.0 | 1.8 | 1.9 |
| 0.5 | 1.0 | 2.7 | 2.6 | 2.3 | 2.2 | 2.5 | 2.3 |
| 0.25 | 1.0 | 2.1 | 2.2 | 1.9 | 2.0 | 2.1 | 1.6 |
| 0.125 | 1.0 | 2.5 | 2.1 | 1.8 | 1.7 | 2.0 | 1.9 |
| 0.0625 | 1.0 | 1.8 | 1.7 | 2.0 | 1.8 | 1.8 | 1.9 |
| 0.031 | 1.0 | 1.7 | 1.6 | 1.9 | 1.9 | 2.4 | 1.7 |

The 0.5 μg BB27 titers in the six samples and the 1 μg titer for the control were used to evaluate FEUs using COULTER Flow-Cal 575 beads. Data are shown in Table 13.

TABLE 13

| Sample | FEU units Donor 1 | FEU units Donor 2 | FEU, normalized Donor 1 | FEU, normalized Donor 2 | PE/dextran or antibody Donor 1 | PE/dextran or antibody Donor 2 |
|---|---|---|---|---|---|---|
| Control | 19,726 | 17,342 | 1.0 | 1.0 | 0.85 | 0.85 |
| Fraction 19 | 43,930 | 31,856 | 2.2 | 1.8 | 1.9 | 1.5 |
| Fraction 20 | 36,626 | 31,259 | 1.9 | 1.8 | 1.6 | 1.5 |
| Fraction 21 | 31,558 | 25,297 | 1.6 | 1.5 | 1.4 | 1.3 |
| Fraction 22 | 30,216 | 25,893 | 1.5 | 1.5 | 1.3 | 1.3 |
| Fraction 23 | 38,713 | 29,918 | 2.0 | 1.7 | 1.7 | 1.5 |
| Fraction 24 | 30,663 | 27,682 | 1.5 | 1.6 | 1.3 | 1.4 |

Note the lower PE fluorescence enhancements and lower apparent PE-to-dextran molar ratios obtained on targeted T-cells in whole blood with BB27-1X-Amdex-PE (up to 2.2-fold over the control) compared to enhancements with BB27-5X-Amdex-PE (up to 5.6-fold). Although 1X-Amdex (1,000,000 dalton) has a higher average molecular weight than 5X-Amdex (350,000 dalton), 1X-Amdex also has a longer extended sugar polymer chain which can in its conjugate with PE and BB27 antibody bridge two or more receptor sites for BB27 antibody on the T cell surface. 5X-Amdex in its PE and BB27 antibody conjugate may not have the required chain length to bridge two or more receptor sites.

BB27-5X-Amdex-PE conjugates of trials 3 and 4 showed higher MFI ratios, fraction/control, for mean channel PE fluorescent intensities. For 0.15 to 0.009 μg of conjugate mixed with whole blood, lysed and quenched, the MFI ratios ranged from 2.9 to 10.9 with trial 3 conjugate and from 3.2 to 15.7 with trial 4 conjugate for two blood donors. For the 2× amount of sulfo-SMCC-5X-Amdex used in trial 4, MFI ratios obtained with this conjugate were about 1.5× higher and did indicate more PE per dextran conjugate. The larger amount of aminodextran used in the 2× preparation would also give a larger amount of higher molecular weight aminodextran capable of taking on more PE.

EXAMPLE 11

Flow Cytometric Analyses of Transfectant Cells with IL-12Rβ.44-PE and IL-12Rβ.44-aminodextran-PE Conjugates Because of very low fluorescent intensities, overlapping with the autofluorescent background of cells, from cells targeted in whole blood by the direct IL-12Rβ.44-PE conjugate, a transfectant cell line was used to compare fluorescent intensities of cells labeled with the direct versus aminodextran crosslinked IL-12Rβ.44-PE conjugate by flow cytometry. Titers of the control, IL-12Rβ.44-PE, and the samples, 1×IL-12Rβ.44-5X-Amdex-PE and 2×IL-12Rβ.44-5X-Amdex-PE, starting at 0.3 μg per tube, were run on IL-12R receptor transfectant cells (PB112) mixed 1:1 with untransfected parent cells (PB110) for a total number of 10⁶ cells/tube in a reaction volume of 200 μl. Cells were incubated for 1 hour at room 4 temperature, washed once with PBS and analyzed by flow cytometry (COULTER XL). Mean channel PE fluorescence intensities and sample intensities relative to the control, obtained with the same instrument settings, are listed in Tables 14 and 15.

TABLE 14

| | 1x conjugate | | | | |
|---|---|---|---|---|---|
| IL-12Rβ.44, μg | Control | Fraction 20 | Fraction 21 | Fraction 22 | Fraction 23 |
| Mean Channel PE Fluorescence Intensities | | | | | |
| 0.3 | 162.5 | 455. | 411.3 | 528. | 854.3 |
| 0.15 | 161.7 | 365.8 | 318.2 | 293.7 | 820.4 |
| 0.075 | 121.4 | 225.4 | 194.8 | 212.5 | 457.4 |
| 0.0375 | 97.3 | 185.7 | 94.1 | 143.9 | 398.9 |
| 0.019 | 67.7 | 102.9 | 79.2 | 99.3 | 195.2 |
| 0.009 | 41.5 | 82.5 | 53.6 | 46.3 | 101.2 |
| MFI Ratios, Fraction/Control | | | | | |
| 0.3 | 1.0 | 2.8 | 2.5 | 3.2 | 5.3 |
| 0.15 | 1.0 | 2.3 | 2.0 | 1.8 | 5.1 |
| 0.075 | 1.0 | 1.9 | 1.6 | 1.8 | 3.8 |
| 0.0375 | 1.0 | 1.9 | 1.0 | 1.5 | 4.1 |
| 0.019 | 1.0 | 1.5 | 1.2 | 1.5 | 2.9 |
| 0.009 | 1.0 | 2.0 | 1.3 | 1.1 | 2.4 |

TABLE 15

| 2x conjugate | Mean Channel PE Fluorescence Intensities | | | |
|---|---|---|---|---|
| IL-12Rβ.44, μg | Control | Fraction 21 | Fraction 22 | Fraction 23 |
| 0.3 | 162.5 | 144. | 131.8 | 146.9 |
| 0.15 | 161.7 | 121.6 | 111.2 | 122.1 |
| 0.075 | 121.4 | 65.5 | 58.6 | 61.9 |
| 0.0375 | 97.3 | 39.1 | 37.9 | 51.2 |
| 0.019 | 67.7 | 21.9 | 19. | 25.3 |
| 0.009 | 41.5 | 11.4 | 8.85 | 12.1 |

Fractions of the 1×IL-12Rβ.44-5X-Amdex-PE conjugate showed up to 5.3-fold amplification of PE fluorescent intensity over the direct IL-12Rβ.44-PE conjugate, when tested with transfected cells by flow cytometry. However, use of 2×-activated sulfo-SMCC-5X-Amdex in preparing the IL12Rβ.44-5X-Amdex-PE conjugate showed no advantage in marker fluorescence intensity over the direct IL-12Rβ.44-PE conjugate (F/P ratio=0.967), which was used as the control. The greater degree of activation of 5X-Amdex in the 2× conjugate obviously resulted in considerably less PE in the same conjugate.

EXAMPLE 12

Flow Cytometric Analyses of Whole Blood with BY55-PE and BY55-aminodextran-PE Conjugates BY55 antibody conjugates were prepared to show the applicability of the method of fluorescence amplification with an IgM class antibody of much higher molecular weight, ~900,000 Daltons, compared to ~160,000 Daltons for IgG antibodies. Titers of the control, BY55-PE, and the samples, 1×BY55-5X-Amdex-PE and 2×BY55-5X-Amdex-PE, starting with 0.9 μg per tube (in 10 μl), with 100 μl whole blood, were run with one blood donor. Cells were incubated for 1 hour at room temperature, lysed on a COULTER Q-Prep, washed once with PBS and run on a flow cytometer (COULTER XL). Mean channel PE fluorescence intensities relative to the control, obtained with the same instrument settings, are listed in Tables 16 and 17.

TABLE 16

| | 1x conjugate | | | |
|---|---|---|---|---|
| BY55, μg | Control | Fraction 20 | Fraction 21 | Fraction 22 | Fraction 23 |
| Mean Channel PE Fluorescence Intensities | | | | |
| 0.9 | 2.42 | 44.9 | 29.1 | 22.9 | 10.8 |
| 0.45 | 2.58 | 37.1 | 29.5 | 18.6 | 9.45 |
| 0.225 | 2.55 | 29.1 | 23.7 | 12. | 9.32 |
| 0.1125 | 1.95 | 28.8 | 24.1 | 10.5 | 7.33 |
| 0.0563 | 2.08 | 23. | 21.5 | 11.8 | 9.03 |
| MFI Ratios, Fraction/Control | | | | |
| 0.9 | 1.0 | 18.6 | 12.0 | 9.5 | 4.5 |
| 0.45 | 1.0 | 14.4 | 11.4 | 7.2 | 3.7 |
| 0.225 | 1.0 | 11.4 | 9.3 | 4.7 | 3.7 |
| 0.1125 | 1.0 | 14.8 | 12.4 | 5.4 | 3.8 |
| 0.0563 | 1.0 | 11.1 | 10.3 | 5.7 | 4.3 |

TABLE 17

| | 2x conjugate | | | |
|---|---|---|---|---|
| BY55, μg | Control | Fraction 19 | Fraction 20 | Fraction 21 | Fraction 22 |
| Mean Channel PE Fluorescence Intensities | | | | |
| 0.9 | 2.42 | 21.9 | 29.4 | 15.0 | 9.95 |
| 0.45 | 2.58 | 25.2 | 20.7 | 13.9 | 7.33 |
| 0.225 | 2.55 | 27.2 | 14.4 | 12.7 | 7.51 |
| 0.1125 | 1.95 | 15.0 | 13.6 | 9.3 | 6.33 |
| 0.0563 | 2.08 | 13.6 | 10.5 | 9.5 | 2.42 |
| MFI Ratios, Fraction/Control | | | | |
| 0.9 | 1.0 | 9.0 | 12.1 | 6.2 | 4.1 |
| 0.45 | 1.0 | 9.8 | 8.0 | 5.4 | 2.8 |
| 0.225 | 1.0 | 10.7 | 5.6 | 5.0 | 2.9 |
| 0.1125 | 1.0 | 7.7 | 7.0 | 4.8 | 3.2 |
| 0.0563 | 1.0 | 6.5 | 5.0 | 4.6 | 1.2 |

Data from the 1×BY55 conjugate, fractions 20 and 21, and the 2×BY55 conjugate, fractions 19 and 20, were also used to evaluate FEUs by using COULTER Flow-Cal 575 beads to place the PE intensities on an absolute scale. The results are shown in Table 18.

TABLE 18

| BY55, μg | Control | 1x, Frac 20 | 1x, Frac 21 | 2x, Frac 19 | 2x, Frac 20 |
|---|---|---|---|---|---|
| FEU units | | | | | |
| 0.9 | 22,601 | 405,546 | 263,114 | 198,208 | 265,818 |
| 0.45 | 24,044 | 335,231 | 266,720 | 287,956 | 187,390 |
| 0.225 | 23,773 | 263,113 | 214,434 | 245,986 | 130,597 |
| 0.1125 | 18,364 | 260,409 | 218,040 | 136,006 | 123,386 |
| 0.0563 | 19,536 | 208,124 | 194,602 | 123,386 | 95,440 |
| FEU, normalized | | | | | |
| 0.9 | 1.00 | 17.9 | 11.6 | 8.8 | 11.8 |
| 0.45 | 1.00 | 13.9 | 11.1 | 9.5 | 7.8 |
| 0.255 | 1.00 | 11.1 | 9.0 | 10.3 | 5.5 |
| 0.1125 | 1.00 | 14.2 | 11.9 | 7.4 | 6.7 |
| 0.0563 | 1.00 | 10.7 | 10.0 | 6.3 | 4.9 |
| PE/dextran or antibody | | | | | |
| 0.9 | 0.862 | 15.4 | 10.0 | 7.6 | 10.2 |
| 0.45 | 0.862 | 12.0 | 9.6 | 8.2 | 6.7 |
| 0.255 | 0.862 | 9.6 | 7.8 | 8.9 | 4.7 |
| 0.1125 | 0.862 | 12.2 | 10.2 | 6.4 | 5.8 |
| 0.0563 | 0.862 | 9.2 | 8.6 | 5.4 | 4.2 |

The corrected F/P or PE/antibody ratio of 0.862 for the direct BY55-PE conjugate was used to obtain PE/dextran ratios from normalized FEU values by multiplying each value by 0.862. The MFI ratios obtained for BY55-5X-Amdex-PE conjugates are similar to values obtained for BB27-5X-Amdex-PE conjugates in trials 3 and 4, and thus indicate that both IgM and IgG class antibody-5X-Amdex-PE conjugates can contain similar numbers of PE molecules per conjugate. Similarly, based on one or two BY55/dextran, the PE/dextran ratios at saturation from Table 18, and the PE concentrations from Table 7, calculated BY55 concentrations are up to tenfold higher than BY55 concentrations determined by ELISA and shown in Table 7. The lower ELISA figures for both BB27 and BY55 antibodies in the aminodextran-crosslinked conjugates of antibody and PE probably reflect the relative inaccessibility of various antibody epitopes in the conjugates to the goat anti-mouse antibody used in the assay. Since the standard curve in this assay is generated using free antibody, the conjugate antibody concentrations are likely to be underestimated.

Figure 3A:
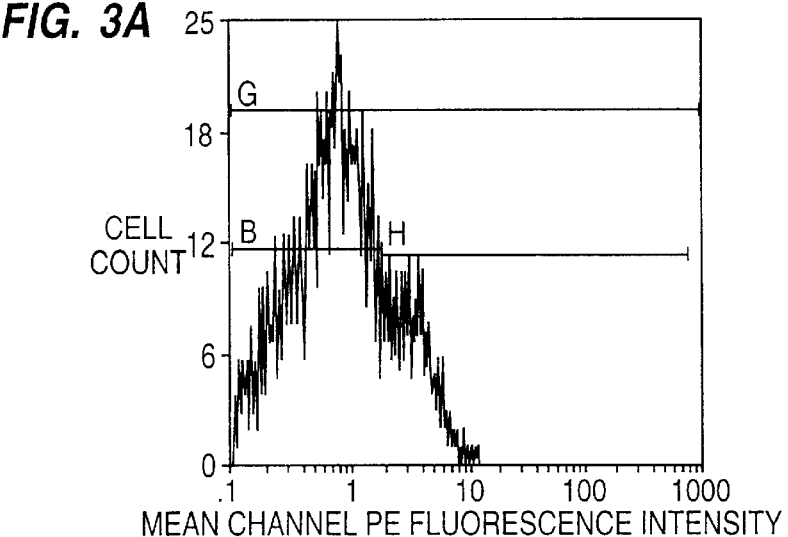
FIGS. 3A, 3B and 3C compare the fluorescence intensity of lymphocytes marked by the direct conjugate BY55-PE and by different fractions of the aminodextran crosslinked conjugate, BY55-5X-Amdex-PE, when each conjugate is mixed with whole blood.
Figure 3B:
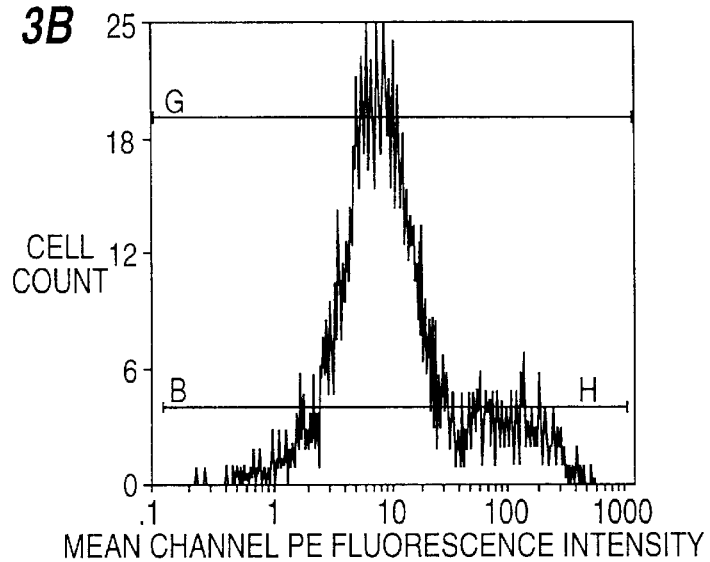
Figure 3C:
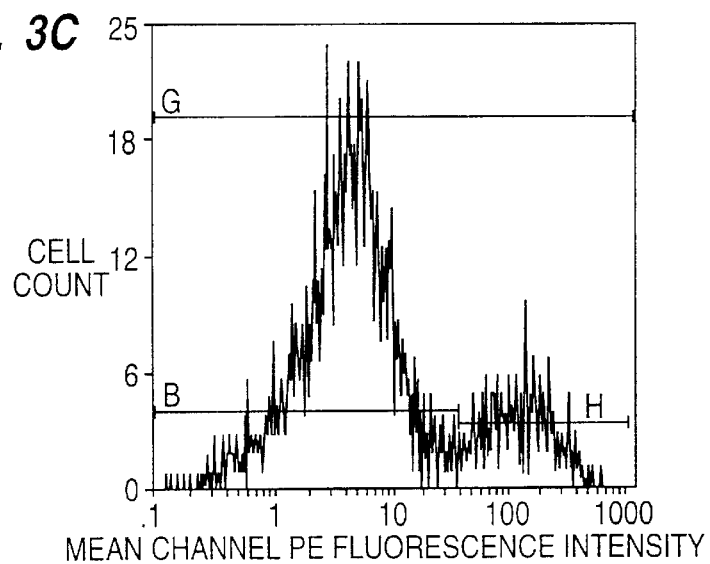
Figure 4A:
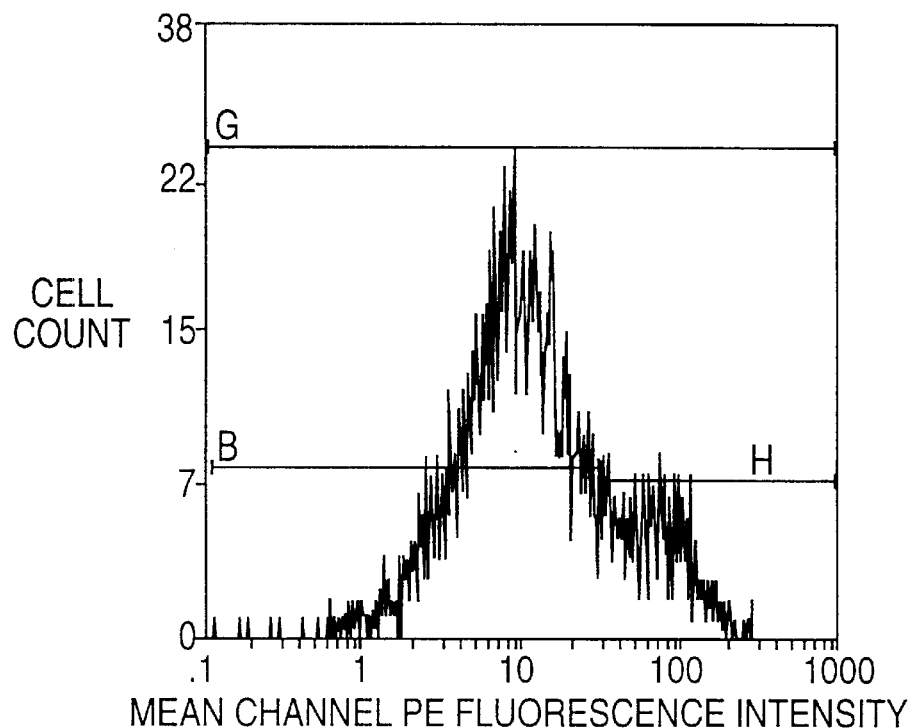
FIGS. 4A and 4B show histograms for lymphocytes in whole blood, either unblocked or blocked with free anti-BY55, prior to mixing crosslinked conjugate BY55-5X-Amdex-PE with whole blood.
Figure 4B:
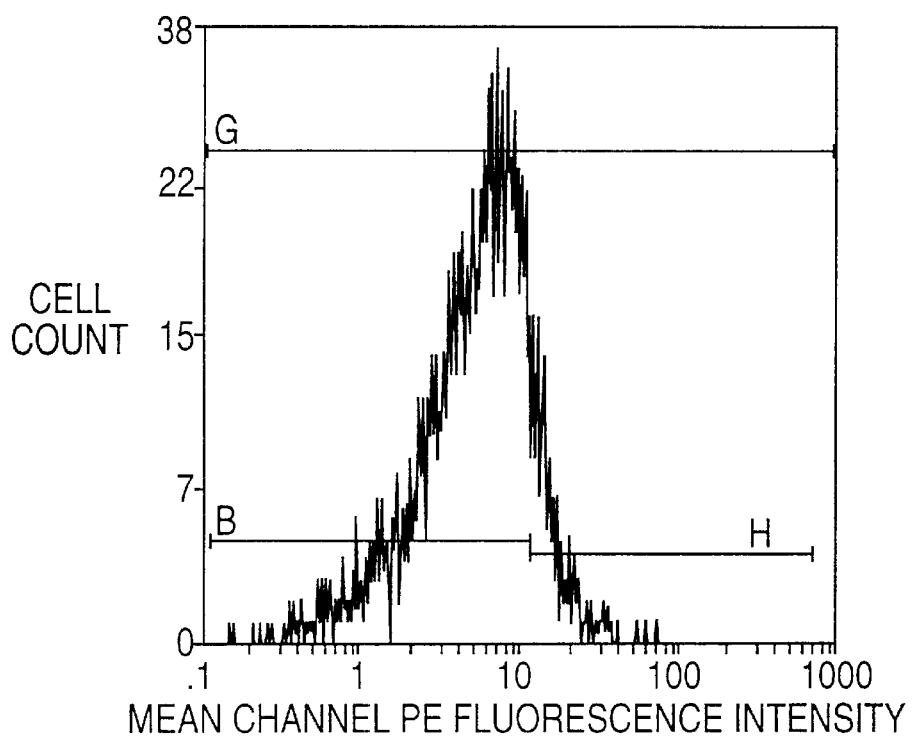
Figure 5A:
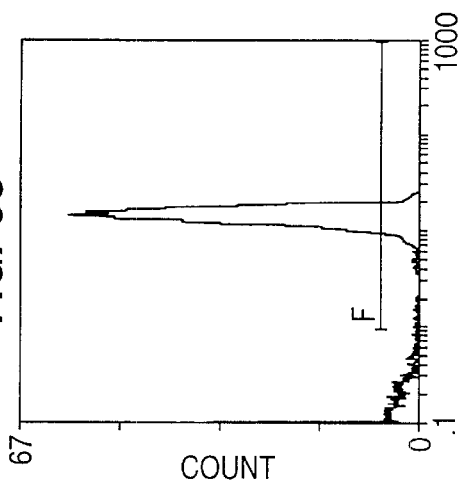
FIGS. 5A–5F are histograms which show the fluorescence intensity of lymphocytes stained simultaneously with CD4-FITC, BB27-PE, and CD8-ECD compared to lymphocytes stained simultaneously with CD4-FITC, BB27-5X-Amdex-PE and CD8-ECD, when each set of markers is mixed with whole blood.
Figure 5D:
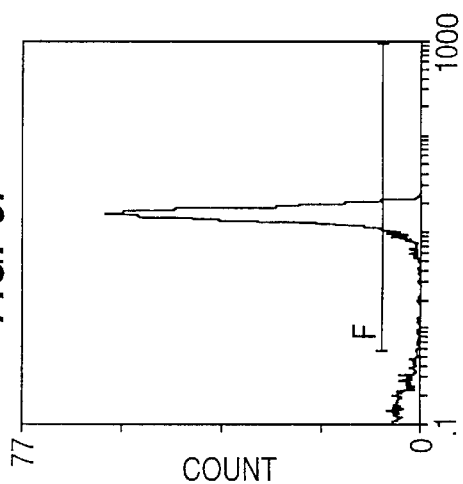
Figure 5B:
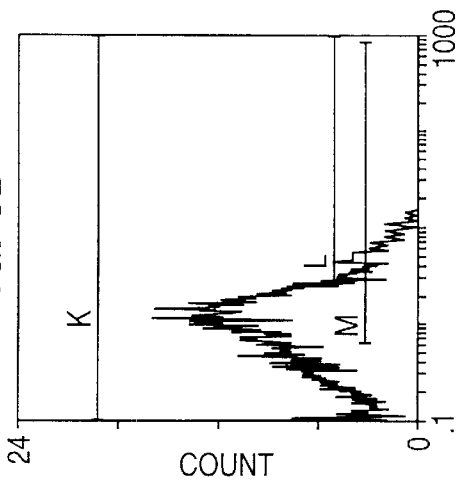
Figure 5E:
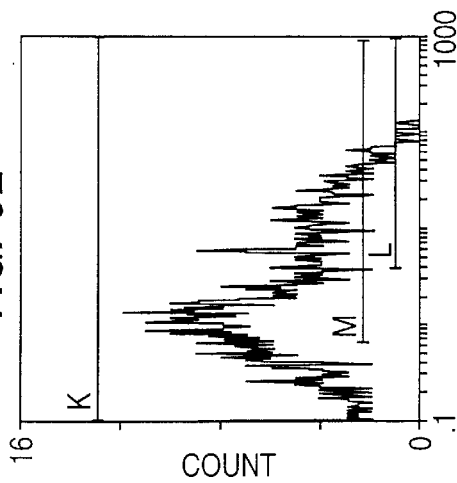
Figure 5C:
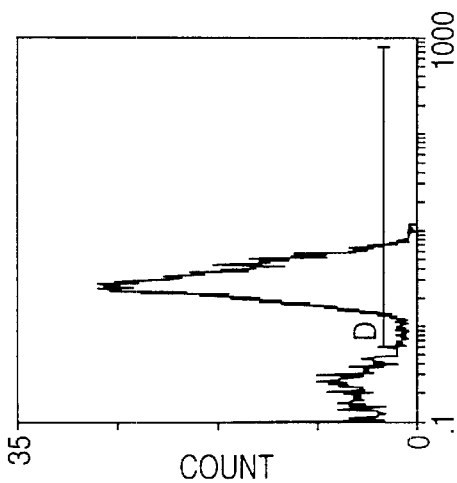
Figure 5F:
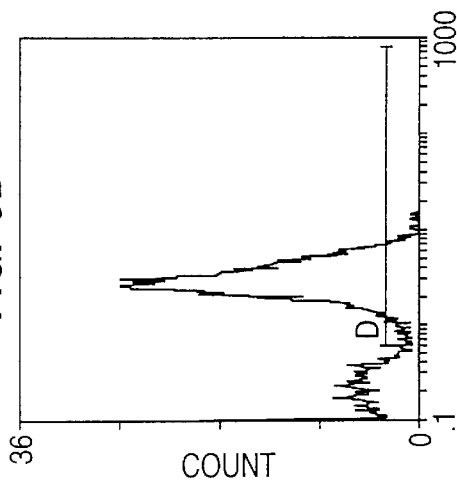

The much greater resolution of targeted BY55+ cells in whole blood with the 5X-Amdex-crosslinked BY55-PE conjugates, 1× Fraction 20 and 2× Fraction 19, compared to the direct BY55-PE conjugate is clearly evident for another blood donor in FIGS. 3A and 3B, in which the cell count versus PE fluorescent intensity histogram, gated on lymphocytes in the FS versus SS histogram, is shown for each marker. FIGS. 3A and 3B represent staining of scatter gated lymphocytes with BY55 antibody. 100 μL of whole blood from a normal donor was stained with 10 μL containing 0.25 μg of BY55 as (FIG. 3A) BY55-PE, (FIG. 3B) BY55-5X-Aimdex-PE, 1×/fraction 20 or (C) BY55-5X-Amdex-PE, 2×/fraction 19. FIGS. 3A, 3B and 3C shows that the crosslinked conjugate has 30-fold higher fluorescence intensity on BY55+ lymphocytes. The large autofluorescence signals, centered at mean channel PE fluorescent intensities of 0.625, 6.60, and 3.36, and the BY55+ cell signals at 3.67, 75.4, and 90.0 for BY55-PE direct conjugate, 1×Fraction 20, and 2× Fraction 19, respectively, are best resolved for the 2× Fraction 19 sample, in which, according to the PE/dextran ratios, the conjugate contains one additional IgM and about four fewer PE per conjugate compared to the 1× Fraction 20 sample. Proportionally more IgM antibody in the conjugate may give less background fluorescence due to better presentation of the antibody and, thus, greater specificity of conjugate for targeted cells, and, at the same time, less non-specific binding of the conjugate to other cells. The specificity of the binding is shown in FIGS. 4A and 4B, in which lymphocytes from a third donor are stained with and without previous blocking by 750 μg/ml unlabeled BY55 antibody. FIGS. 4A and 4B show staining of scatter gated lymphocytes with BY55 antibody. 100 μL of whole blood from a normal donor was stained with (FIG. 4A) 10 μL containing 0.25 μg of BY55 antibody in the form of BY55-5X-Amdex-PE, 2×/fraction 19 or (FIG. 4B) BY55-5X-Amdex-PE, 2×/fraction 19, after blocking with an excess (750 μg/mL) of unlabeled BY55. FIGS. 4A and 4B show that the conjugate is specific for the BY55 antigen.

EXAMPLE 13

Use of Antibody-Dextran-Phycoerythrin Conjugates in Multi-Color Staining

To determine whether the increased mass of the antibody-dextran-phycoerythrin conjugates would sterically hinder binding of specific antibodies to other cell surface antigens, BB27-5X-Amdex-PE (fraction 23) was incubated simultaneously with CD4-FITC and CD28-ECD. The CD4, CD28 and BB27 antigens are expressed on CD4+ T cells which are functionally distinct from CD4+CD28+BB27-cells [Gouttefangeas et. al., *Int. Immunol.* 6(3)423, (1994)]. Antibodies were incubated with 100 μl whole blood for 1 hour at a concentration of 0.25 μg each per test in a total volume of 110 μl. Blood was lysed on a COULTER Q-Prep, washed once with PBS and run on a flow cytometer (COULTER XL). When gated on the lymphocyte population, single parameter histograms (FIGS. 5A–5F) show the enhanced signal produced by staining with BB27-5X-Amdex-PE compared to staining with BB27-PE. FIGS. 5A–5F shows multicolor analysis using three markers. FIGS. 5A–5F show that enhanced signal are obtained even when multiple markers are used. There was no difference in the binding of irrelevant antibodies CD4 and CD28, as demonstrated by the similarity in mean fluorescence intensity peak positions for these antibodies in the presence of BB27-5X-Amdex-PE or BB27-PE. This indicated that the increased mass of BB27-5X-Amdex-PE, compared to BB27-PE, does not affect the binding of other antibodies to cell surface antigens, thus expanding the potential use of this invention to multicolor flow cytometric analysis.

EXAMPLE 14

Preparation of Anti-CD8αβ Antibody-PC5 Conjugate

Direct monoclonal antibody-fluorochrome (PE, PC5, ECD) conjugates are commercially available for most antibodies from Coulter Corporation or Immunotech, as prepared by established procedures of conjugation reactions of iminothiolane activated PE (or PC5; ECD) with sulfo-SMCC activated antibody or iminothiolane activated PE (or PC5; ECD) with DTT (dithiothreitol) reduced antibody. The molar ratio of monoclonal antibody:fluorochrome in these conjugates is about 1:1. Conjugation of IgG monoclonal antibody to PC5 was accomplished by sulfosuccinimidyl 4-[N-maleimidomethyl]cyclohexane-1-carboxylate (sulfo-SMCC) activation of PC5 and activation of antibody by reduction of disulfide bonds in the hinge region with dithiothreitol (DTT).

A. Activation of Monoclonal Antibody (MCA).

For 50 mg of MCA at a concentration of 14.04 mg/mL, 3.549 mL of MCA concentrate were required. A 15.4 mg/mL solution of DTT in 1×PBS was prepared and used at an activation ratio of DTT: MCA=300:1. Thus, to make a total volume of 10 mL with 5 mg/mL of MCA, 5.451 mL of 1×BBS buffer (20 mM borate, 150 mM sodium chloride, pH 8.8) were placed in a reaction vial, to which were added 3.549 mL of MCA solution with stirring at 25° C. and then slowly added 1.000 mL of DTT solution. The reaction mixture in a vial was incubated at 25° C. for 20 minutes, after which 2.5 mL of MES (2-[N-morpholino] ethanesulfonic acid) quenching buffer (50 mM MES, 5.0M sodium perchlorate, 4 mM EDTA (ethylenediaminetetraacetic acid), pH 5, were added and the reaction mixture was incubated 2 minutes further. Then, immediately the activated MCA sample was applied to the top of a 200 mL G-50 Sephadex column, equilibrated with MES column buffer (50 MM MES, 100 mM sodium perchlorate, 4 mM EDTA, pH 6.0). The activated MCA was eluted from the column with MES buffer and fractions of the first peak absorbing at 280 nm were collected. The activated MCA concentration in mg/mL was determined by the $A_{280}$ value. 34 mL of activated MCA solution at 1.394 mg/mL (47.4 mg) were obtained.

B. Activaion of PC5 with Sulfo-SMCC.

PC5, the PE (R-phycoerythrin (red algae))-5'-cyanine tandem conjugate was prepared as described in U.S. Pat. No. 4,542,104 and U.S. Pat. No. 5,272,257. For 55 mg of PC5 at a concentration of 14.69 mg/mL in 1×BBS buffer, 3.744 mL of the PC5 concentrate were required. A 4.5 mg/mL solution of sulfo-SMCC in 1×BBS buffer was prepared and used at an activation ratio of sulfo-SMCC: PC5=40:1. Thus, to make 5 mg/mL of PC5 at a total volume of 11 mL, 5.936 mL of 1×BBS buffer were placed in a reaction vial, to which were added 3.744 mL of PC5 solution with stirring at 25° C. and then, slowly added 0.44 mL of NEM (N-ethyl maleimide, 31.25 mg/mL in 1×BBS buffer) solution. The reaction mixture in the vial was incubated for 30 minutes. Then, 0.88 mL of sulfo-SMCC solution (4.5 mg/mL) was added to the mixture which was incubated for a further 60 minutes. At the end of the last incubation period, 1.1 mL of 1M ammonium chloride in 1×BBS buffer were added to the mixture, and further incubated for 2 minutes. Then immediately the activated PC5 was loaded onto a 200 mL G-50

Sephadex column, equilibrated with MOPS (3-[N-morpholino]propanesulfonic acid) column buffer (50 mM MOPS, 100 mM sodium perchlorate, 4 mM EDTA, pH 7.0). The activated PC5 was eluted from the column with MOPS buffer and the first colored peak off the column was collected. The concentration of 1.962 mg/mL of activated PC5 was determined as $A_{565.5}/8.167$. The activated PC5 was diluted to 1.5 mg/mL with MOPS buffer to give 32.7 mL total volume.

C Conjugation of MCA with PC5.

For conjugation, equal volumes (32.7 mL) of activated MCA at 1.4 mg/mL and activated PC5 at 1.5 mg/mL were mixed by adding activated MCA into stirring activated PC5. The reaction mixture was incubated at 25° C. for 2 hours. At the end of the mixing period, 2.642 mL of 31.25 mg/mL NEM in 1×BBS buffer were further added to the reaction mixture, which was roller mixed for an additional 5 minutes.

D. Purification of MCA-PC5 Conjugate.

A Superdex 200 prep grade column (3.4 mL of column per mg of MCA or 318 mL) equilibrated with 1×PBS, 2 mM EDTA, pH 7.2 buffer was prepared. The MCA-PC5 reaction mixture was concentrated to less than 2% of the Superdex pg column volume, 4.33 mL. The sample was loaded onto the Superdex 200 pg column, and eluted with 1×PBS, 2 mM EDTA, pH 7.2 buffer at 119 mL/hr. The $A_{280}/A_{565.5}$ ratio was calculated for each fraction. All fractions with ratios from 0.43 until two fractions before the free PC5 eluates were pooled. For example, the pooled CD8αβ-PC5 fractions, 25 mL, were concentrated to a volume of 3.45 mL, less than 1% of the column volume, by using an Amicon YM30 membrane, diafiltering the concentrate with 1×PBS, 0.1% sodium azide, 0.1 mM EDTA buffer, and centrifuging the CD8αβ-PC5 conjugate at 1800×g for 15 minutes at 4° C. A 100-fold dilution of this pooled sample gave $A_{565.5}$= 0.4809 or (/8.167)×100=5.888 mg/mL PC5 and 20.31 mg total PC5 in the CD8αβ-PC5 conjugate, and $A_{280}$=0.1513 or [0.4809/5.476 (PC5's $A_{565.5}/A_{280}$)]×100=6.349 mg/mL CD8αβ and 21.90 mg total CD8αβ in the CD8αβ-PC5 conjugate. The molar ratio of PC5CD8αβ is therefore (20.31 mg PC5/240,000)//(21.90 mg CD8αβ/160,000)=0.618. A corrected F/P ratio based on the formula, MCA:PC5=[$A_{280}/A_{565.5}$ (conjugate)-$A_{280}/A_{565.5}$ (dye)]×8.77, is 0.864. Similar methods were used to prepare a CD4-ECD conjugate having an F/P ratio of 0.96. Alternatively, the direct MCA-dye conjugate could be prepared by sulfo-SMCC activation of antibody, 2-iminothiolane activation of dye (e.g., PE or PC5), followed by conjugation and purification, as described in above.

EXAMPLE 15

Figure 6A:
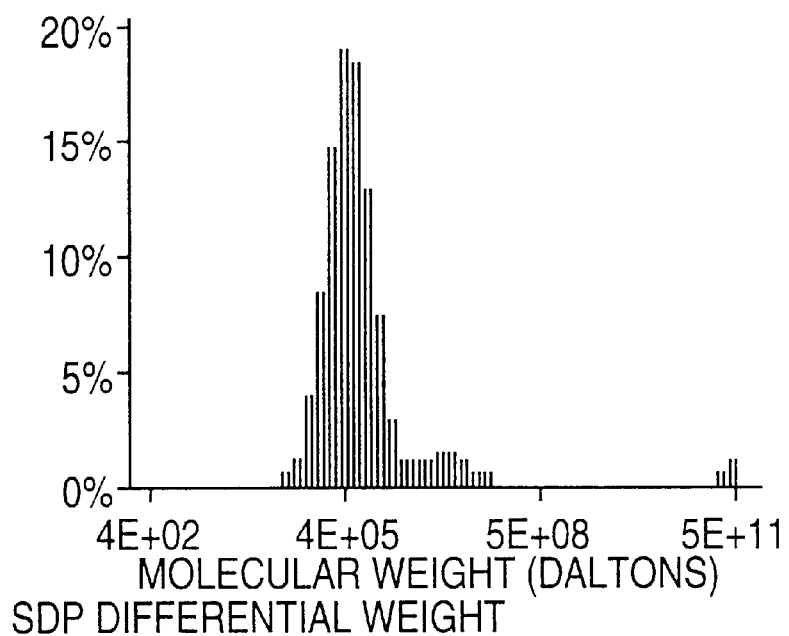
FIG. 6A is a histogram showing a plot of relative weight percent (mass %) of aminodextran molecules (vertical axis) versus their molecular weights (daltons) or size distribution processor (SDP) differential weight distribution of a 5X-aminodextran (5X-Amdex) sample suitable for use in preparation of antibody-5X-Amdex-phycobiliprotein (i.e., PE, PC5, or ECD) conjugates which yield enhanced fluorescence emission intensities, before sulfosuccinimidyl 4-[N-maleimidomethyl]cyclohexane-1-carboxylate (sulfo-SMCC) activation and purification as measured on a Coulter N4MD Sub-Micron Particle Analyzer.
Figure 6B:
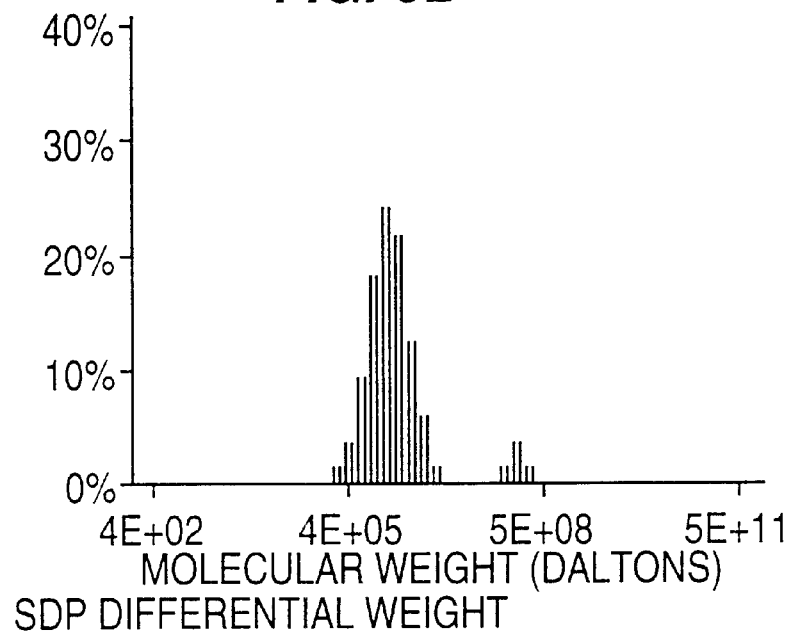
FIG. 6B is a histogram showing relative weight percent (mass %) of Amdex molecules vs their molecular weight or SDP differential weight distribution of a 5X-Amdex sample suitable for use in preparation of antibody-5X-Amdex-PE, PC5, or ECD conjugates which yield enhanced fluorescence emission intensities, after sulfo-SMCC activation and purification as measured on the Coulter analyzer, as described for FIG. 6A.

Properties of Preferred Aminodextran in Preparation of Antibody-Aminodextran-Phycobiliprotein Conjugates The procedure for preparation of conjugates was similar to that described in U.S. Pat. No. 5,527,713 to prepare conjugates of anti-CD3 antibody with aminodextran, either 1X-Amdex or 5X-Amdex. However, in this example, two different proteins, one, a monoclonal antibody and the other, a fluorescent protein, were conjugated simultaneously to the aminodextran as described above for the fluorescent dye, PE. The requirements for the aminodextran used in the preparation of the conjugates can be defined more precisely herein. Syntheses of 5X-Amdex have been described in U.S. Pat. Nos. 5,466,609; 5,527,713; 5,552,086; 5,639,620; and 5,658,741. The preferred 5X-Amdex has an average molecular weight (MW) as high as possible and as nearly equal to the dextran (preferably *Leuconostoc mesenteroides* strain B-512) of 2M average MW, which was used as a starting material in all experiments. Average MW lower than 2M were obtained for the product 5X-Amdex in all preparations due to the competing reaction of aminolysis of the dextran during amination of oxidized dextran, dextran aldehyde, with 1,3-diaminopropane. No reduction in average MW was observed after the periodate oxidation of dextran, as measured for appropriately diluted samples on the Coulter N4MD Sub-Micron Particle Analyzer. Best results for antibody-5X-Amdex-dye conjugates were obtained when the average MW of 5X-Amdex was equal to or greater than 350,000 Daltons. Material which analyzed as about ⅐ to ⅑ degree of substitution of dextran by two diaminopropane molecules per oxidized glucose residue, but showed an average MW less than about 350,000 Daltons did not produce conjugates capable of fluorescence amplification. With the preferred 5X-Amdex, activation of the aminodextran with sulfo-SMCC, separation by chromatography on a G-50 Sephadex column, and selection of material under the first narrow peak detected by an $A_{280}$ monitor served to yield sulfo-SMCC-activated 5X-Amdex with an even higher average MW in the range 1 to 2M Daltons. The relative weight (mass)-average MW distribution of a 5X-aminodextran sample suitable for use in preparation of antibody-5X-Amdex-PE, PC5, or ECD conjugates which yield enhanced fluorescence emission intensities, before and after sulfo-SMCC activation and purification as measured on a Coulter N4MD Sub-Micron Particle Analyzer, is shown in FIGS. 6A and 6B.

EXAMPLE 16

Trial 1 Conjugation with Total Protein, CD8αβ and PC5, to 5X-Amdex Weight Ratios of 3:1 and an Antibody: 5X-Amdex Weight Ratio of 1:2.3

A. Activation Aminodextran with Sulfo-SMCC 0.437 mL of a 22.867 mg/mL solution of 5X-Amdex in DW, to which 0.023 mL of 20×PBS buffer solution were added to make a 1×PBS solution, were activated with 0.180 mL of 10 mg/mL sulfo-SMCC solution in 1×PBS. The mixture was roller mixed for about one hour at room temperature. After the mixing was completed, the reaction mixture was immediately applied to the top of a 60 mL G-50 Sephadex column equilibrated with 1×PBS. The sample was eluted using 1×PBS and collected in about 2 mL fractions. Fractions of the first band absorbing at 280 nm contained the high molecular weight activated 5X-Amdex as was verified by Tyndall scatter with a focused visible light beam (Model 650, Cambridge Instruments, Inc., Buffalo, N.Y.). These fractions were pooled to give about 3.7 mL total sulfo-SMCC-activated 5X-Amdex.

B. Activation of Antibody.

CD8αβ monoclonal antibody was activated by the addition of 0.065 mL of a 2 mg/mL solution of iminothiolane in 1×PBS and 0.440 mL 1×PBS to 0.162 mL of CD8β concentrate (61.67 mg/mL). The resulting solution which had an antibody concentration of 15 mg/mL and an iminothiolane molar concentration fifteen-fold larger was mixed at ambient temperature for about one hour. The reaction mixture was then chromatographed on a 60 mL G-50 Sephadex column equilibrated with 1×PBS and the sample was eluted using 1×PBS. The peak fraction of the first band yielded about 3.3 mL of 3.407 mg/mL antibody solution which contained a total of 11.24 mg IT-CD8αβ antibody derivative.

C. Activation of PC5.

PC5 concentrate, prepared as described in U.S. Pat. No. 4,542,104 and U.S. Pat. No. 5,272,257, was activated by the addition of 0.232 mL of a 2 mg/mL solution of iminothiolane in 1×PBS and 0.126 mL 1×PBS to 0.542 mL of PC5 concentrate (66.48 mg/mL). The resulting solution which had a PC5 concentration of 40 mg/mL and an iminothiolane molar concentration 22.5-fold larger was mixed at room temperature for about one hour. The reaction mixture was then applied to the top of a 60 mL G-50 Sephadex column equilibrated with 1×PBS and the sample was eluted with 1×PBS. The first band peak fraction gave about 4.3 mL of 6.683 mg/mL PC5 at an $A_{565}/A_{280}$ ratio of 6.0821, which contained a total of 28.738 mg IT-PC5.

D. Conjugation of IT-CD8αβ and IT-PC5 to Sulfo-SMCC-5X-Amdex.

3:1 total protein: 5X-Amdex weight ratios: 1.257 mL of 3.407 mg/mL IT-CD8αβ solution (about 4.287 mg antibody) were first mixed with 3.849 mL of 6.683 mg/mL IT-PC5 solution (about 25.713 mg PC5), to which were added 3.7 mL of sulfo-SMCC-5X-Amdex solution (about 10 mg 5X-Amdex)and the entire mixture was roller mixed overnight for 16–24 hours. After the mixing was completed, the total volume of the mixture was determined and 0.120 times this volume of 5 mg/mL L-cysteine in 1×PBS was added to each conjugation mixture. The L-cysteine containing mixture was then mixed for an additional 15 minutes to effect blocking of any unreacted sulfo-SMCC moieties. Lastly, 20 mg/mL iodoacetamide in 1×PBS in the amount of 0.120 times the total mixture volume and 1M borate buffer solution, pH 9.8, in the amount of 0.020 times the total mixture volume were added to the mixture. The resulting mixture was mixed for about 30 minutes to block any unreacted sulfhydryl groups.

E. Purification of CD8αβ-5X-Amdex-PC5 Conjugates.

Figure 7:
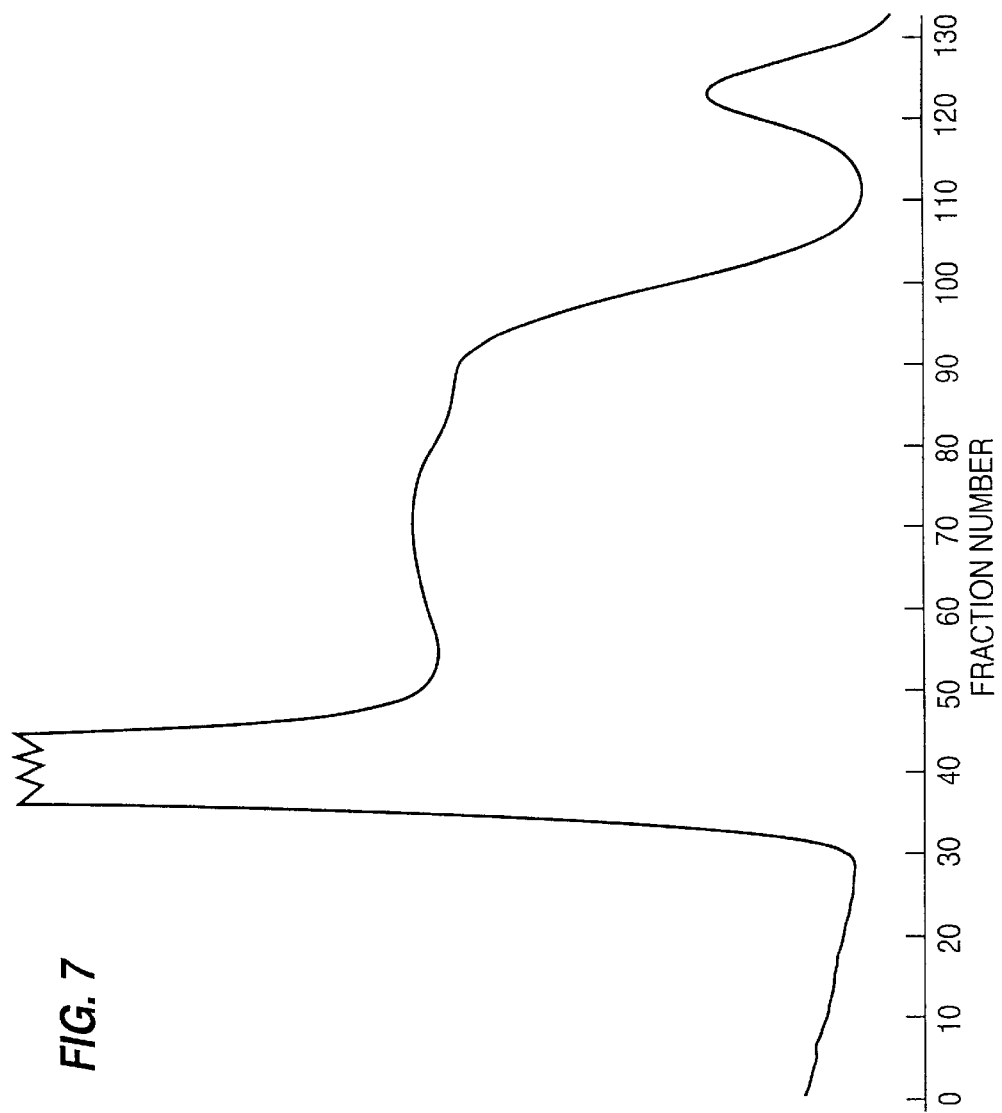
FIG. 7 is a chromatogram showing the $A_{280}$ vs fraction number monitored using a LKB 2138 Uvicord S monitor operating at 280 nm for purification of CD8αβ-5X-Amdex-PC5 conjugation mixtures.

The total volume of conjugation mixture was reduced to about 1.5 mL by centrifuging an Amicon Centri-Prep 30 tube containing the sample for about 30 minutes at 2200 rpm using a refrigerated Beckman J-6B centrifuge. The sample was placed on the top of a Bio-Gel A-15m agarose column (2.5 cm×48 cm) equilibrated with 1×PBS and chromatographed using 1×PBS as eluant. Eluant fractions of about 1.8 mL volume were collected using a Pharmacia LKB FRAC-100 collector operating in the drop collection mode. The fractions were monitored using a LKB 2138 Uvicord S monitor operating at 280 nm. A chromatogram showing the $A_{280}$ versus fraction number recording is displayed in FIG. 7. The first narrow, intense band eluted from the column contained the CD8αβ-aminodextran-PC5 conjugate. A second lower intensity broad band and third band, both of less than one-third the intensity of the first peak, contained ~1:1 PC5: aminodextran conjugate and excess PC5. A medium-to-low intensity, well-separated fourth band was attributed to low molecular weight excess blocking reagents.

The fractions collected for the CD8αβ-5X-Amdex-PC5 conjugate were analyzed spectrophotometrically at 565.5 and 280 nm using a 1 mm path length cell. The concentration of PC5 in mg/mL in the conjugate was derived from the absorbance at 565.5 nm by using the formula, $A_{565.5}/8.167$. Antibody concentrations were determined from the corrected $A_{280}$ value. The active CD8αβ antibody concentration in the conjugate was determined by an ELISA assay for IgG1 antibody; however, assay results appear to show interference from non-antibody parts of the conjugate. Thus, $A_{280}$ values corrected for the PC5 contribution were used to obtain antibody concentrations. Data for fractions 36 to 46 under the first narrow peak in trial 1 are listed in Table 19.

TABLE 19

| Fraction | $A_{565.5}$ | $A_{280}$ | $A_{565.5}/A_{280}$ | PC5, mg/mL | CD8αβ, mg/mL | CD8αβ, µg/mL, ELISA |
|---|---|---|---|---|---|---|
| 36 | 0.0891 | 0.0344 | 2.59 | 0.109 | 0.193 | <0.016 |
| 37 | 0.2661 | 0.0959 | 2.77 | 0.326 | 0.507 | <0.016 |
| 38 | 0.7280 | 0.2450 | 2.97 | 0.891 | 1.212 | 0.029 |
| 39 | 1.1681 | 0.3744 | 3.12 | 1.430 | 1.758 | 0.042 |
| 40 | 1.1810 | 0.3646 | 3.24 | 1.446 | 1.639 | 0.043 |
| 41 | 0.8906 | 0.2648 | 3.36 | 1.090 | 1.134 | 0.040 |
| 42 | 0.5169 | 0.1452 | 3.56 | 0.633 | 0.573 | 0.025 |
| 43 | 0.2720 | 0.0715 | 3.81 | 0.333 | 0.252 | 0.019 |
| 44 | 0.1637 | 0.0397 | 4.13 | 0.200 | 0.118 | <0.016 |
| 45 | 0.1160 | 0.0260 | 4.46 | 0.142 | 0.063 | <0.016 |
| 46 | 0.0915 | 0.0191 | 4.79 | 0.112 | 0.035 | <0.016 |

F. Estimation of Molecular Weights of Antibody-Aminodextran-PE Conjugates

Blue dextran (Sigma, T-2M) was applied to a Bio-Gel A-15 m column that was used to purify the antibody-aminodextran-PE conjugates, eluted from the column with 1×PBS, monitored by $A_{280}$, and collected at the same drop count of 60 drops/fraction. The first narrow peak (about fraction 40) in the elution profile of antibody-aminodextran-dye conjugates occurred in the same fraction as the first narrow peak in the elution profile of blue dextran. Therefore, we estimate the conjugates to have a molecular weight of 2,000,000 Daltons or more. The void volume with an A-15 m agarose column is estimated to contain dextran or dextran derivatives of molecular weight, 15 million/4=3.75 million, or higher. Chromatograms obtained for the antibody-aminodextran-PE, PC5, or ECD conjugates applied to an A-15 m agarose column instead of an A-5 m agarose column that was used in previous work, gave a much better separation of the shoulder to the first main band from the first band, allowing better purification of the conjugates.

EXAMPLE 17

Preparation of Anti-CD4 Antibody-5X-Aminodextran-ECD Conjugates

The procedures were the same as those outlined for the preparation of the CD8αβ-5X-Amdex-PC5 conjugate in Example 16, except anti-CD4 antibody, also of the IgG1 class, was activated with IT and used in the conjugation instead of CD8αβ antibody, and the tandem PE-Texas red or ECD fluorescent dye was used instead of PC5. In trial 2, IT-ECD (7.657 mg), IT-CD4 (1.272 mg) were mixed with sulfo-SMCC-5X-Amdex (5 mg) at concentrations of 1.1 1, 0.184, and 0.725 mg/mL, respectively, during conjugation. The IT-ECD ($A_{565.5}/A_{280}$) ratio was 5.296. The conjugation mixture was concentrated to about 1.5 mL and applied to the top of an A-15 m column. Data for fractions collected at about 3.6 mL per fraction under the first narrow peak in trial 2 are listed in Table 20.

TABLE 20

| Fraction | $A_{565.5}$ | $A_{280}$ | $A_{565.5}/A_{280}$ | ECD, mg/mL | CD4, µg/mL, ELISA |
|---|---|---|---|---|---|
| 18 | 0.0218 | 0.0071 | 3.06 | 0.027 | |
| 19 | 0.0714 | 0.0201 | 3.56 | 0.087 | |
| 20 | 0.0472 | 0.0122 | 3.87 | 0.058 | |
| pool | | | | 0.567 | 1.46 |

EXAMPLE 18

Preparation of Anti-CD56 (or CD4) Antibody-5X-Aminodextran-PE Conjugates

Again, the procedures were the same as those outlined for the CD8αβ-5X-Amdex-PC5 conjugate in Example 16, except anti-CD56 (NKH-1) or -CD4 antibody of the IgG class and PE were activated with IT and used in the conjugation instead of CD8αβ antibody and PC5. In trial 3, the reactants, 2.822 mL of 8.50 mg/mL IT-PE (23.987 mg) were first mixed with 5.4 mL of sulfo-SMCC-5X-Amdex (3.333 mg) solution, to which were then added 2.10 mL of 1.922 mg/mL IT-CD56 (4.036 mg). The IT-PE ($A_{565}/A_{280}$) ratio was 5.800. The conjugation mixture was concentrated to about 1.5 mL and applied to the top of an A-15 m column. Data for fractions collected at 1.8 mL per fraction under the first narrow peak in trial 3 are listed in Table 21.

TABLE 21

| Fraction | $A_{565.5}$ | $A_{280}$ | $A_{565.5}/A_{280}$ | PE, mg/mL | CD56, mg/mL | CD56, µg/mL, ELISA |
|---|---|---|---|---|---|---|
| 36 | 0.1302 | 0.0421 | 3.10 | 0.159 | 0.190 | 1.37 |
| 37 | 0.3752 | 0.1115 | 3.37 | 0.459 | 0.450 | 4.38 |
| 38 | 0.6978 | 0.1964 | 3.55 | 0.854 | 0.729 | 11.4 |
| 39 | 0.7182 | 0.1928 | 3.72 | 0.879 | 0.657 | 12.4 |
| 40 | 0.4911 | 0.1256 | 3.90 | 0.601 | 0.387 | 8.33 |
| 41 | 0.3003 | 0.0732 | 4.10 | 0.368 | 0.200 | 4.58 |
| 42 | 0.1998 | 0.0462 | 4.33 | 0.245 | 0.108 | 3.59 |
| 43 | 0.1508 | 0.0336 | 4.49 | 0.185 | 0.069 | 2.77 |
| 44 | 0.1251 | 0.0271 | 4.62 | 0.153 | 0.049 | 2.35 |
| 45 | 0.1117 | 0.0236 | 4.72 | 0.137 | 0.039 | 4.16 |

In trial 4, 3.117 mL of 8.25 mg/mL IT-PE (25.715 mg) were first mixed with 3.3 mL of sulfo-SMCC-5X-Amdex (10 mg) solution, to which were then added 1.434 mL of 2.991 mg/mL IT-CD4 (4.287 mg). The conjugation mixture was concentrated to about 1.5 mL and applied to the top of an A-15 m column. Data for fractions collected at 1.8 mL per fraction under the first narrow peak in trial 4 are listed in Table 22.

TABLE 22

| Fraction | $A_{565.5}$ | $A_{280}$ | $A_{565.5}/A_{280}$ | PE, mg/mL | CD4, mg/mL | CD4, µg/mL, ELISA |
|---|---|---|---|---|---|---|
| 36 | 0.0797 | 0.0234 | 3.41 | 0.098 | 0.093 | 1.11 |
| 37 | 0.2044 | 0.0596 | 3.43 | 0.250 | 0.234 | 2.85 |
| 38 | 0.3205 | 0.0900 | 3.56 | 0.392 | 0.332 | 5.85 |
| 39 | 0.3387 | 0.0920 | 3.68 | 0.415 | 0.321 | 8.74 |
| 40 | 0.2714 | 0.0702 | 3.86 | 0.332 | 0.222 | 4.83 |
| 41 | 0.1948 | 0.0475 | 4.10 | 0.239 | 0.130 | 3.67 |
| 42 | 0.1436 | 0.0337 | 4.26 | 0.176 | 0.083 | 2.48 |
| 43 | 0.1115 | 0.0254 | 4.39 | 0.137 | 0.057 | 2.01 |

The following Examples 19–22 below demonstrate a comparison of direct and aminodextran-crosslinked fluorophore-antibody conjugates as cell markers in flow cytometry.

EXAMPLE 19

Flow Cytometric Analyses of Whole Blood with CD8αβ-PC5 and CD8αβ-5X-Amdex-PC5 Conjugates CD8αβ-PC5 at an antibody concentration of 5.71 mg/mL and fractions of CD8αβ-5X-Amdex-PC5 conjugates from trial 1 were titered, starting at 3 µg of antibody in the conjugate per tube. Amounts of antibody for the titers were determined from corrected $A_{280}$ values for the conjugates. Dilutions were added to 100 µL of whole blood and incubated for 60 min at room temperature. The mixtures with blood were lysed and quenched on the Coulter Q-PREP, washed once with 1×PBS (by addition of 1 mL of 1×PBS, centrifugation at 500 g for 5 min, discarding supernatant, and resuspension of cells in 1 mL of 1×PBS) and run on a flow cytometer (Coulter Epics XL-MCL).

Figure 8B:
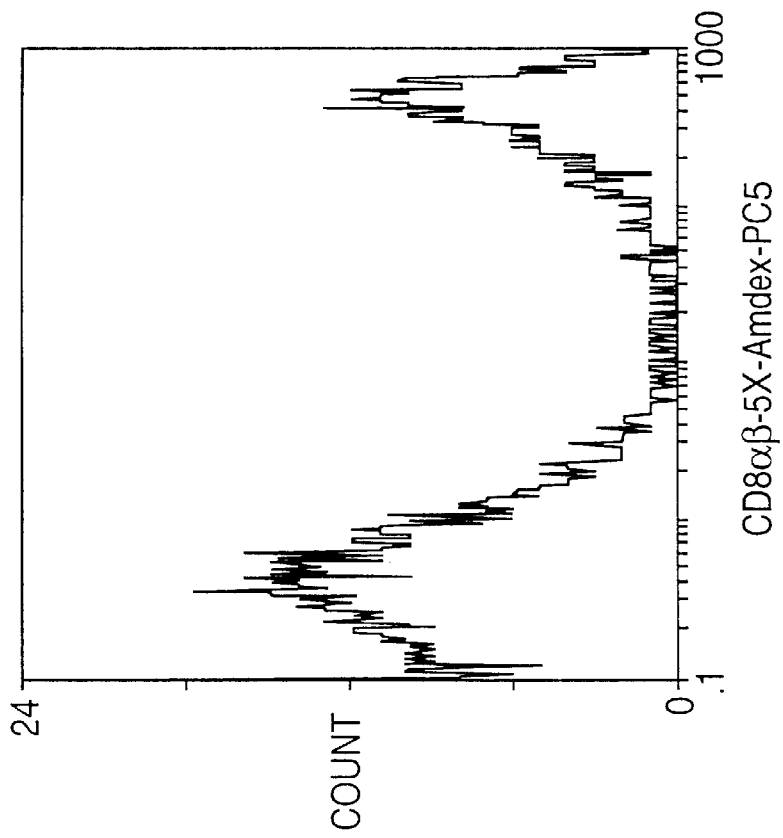
FIG. 8B is a histogram plotting cell count vs. MFI and showing the ability of the CD8αβ-5X-Amdex-PC5 conjugate as a fluorescent marker containing more than two PC5 molecules per dextran molecule to enhance the mean channel PC5 fluorescence intensity of the direct CD8αβ-PC5 conjugate. Staining of scatter gated CD8αβ+ lymphocytes is shown from analysis of 100 μL of whole blood from a normal donor, which was stained with 10 μL containing 2.5 μg of CD8αβ-5X-Amdex-PC5 as ligand. The histograms show that the crosslinked conjugate has 3.5-fold higher fluorescence intensity on CD8αβ+ lymphocytes.
Figure 8A:
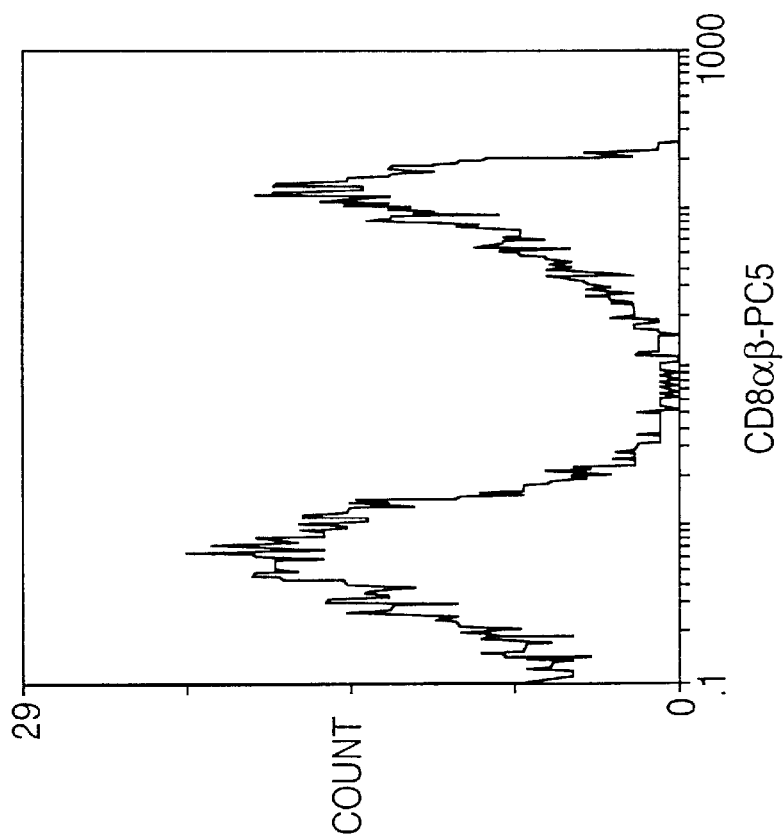
FIG. 8A is a histogram plotting cell count (number of cells) vs. mean channel fluorescence intensity (MFI) and showing the MFI of the direct CD8αβ-PC5 conjugate which contains 0.86 PC5 per antibody molecule. Staining of scatter gated CD8αβ+ lymphocytes is shown from analysis of 100 μL of whole blood from a normal donor, which was stained with 10 μL containing 2.5 μg of CD8αβ-PC5 as ligand.

The ability of CD8αβ-5X-Amdex-PC5 conjugate as a fluorescent marker containing more than two PC5 molecules per dextran molecule to enhance the mean channel PC5 fluorescence intensity obtained with the direct CD8αβ-PC5 conjugate which contains 0.86 PC5 per antibody molecule, is shown in the histograms of FIGS. 8A–8B, RHS versus LHS. The two histograms of FIGS. 8A and 8B show staining of scatter gated lymphocytes. 100 µL of whole blood from a normal donor was stained with 10 µL containing 2.5 µg of CD8αβ antibody as LHS, CD8αβ-PC5 or RHS, CD8αβ-5X-Amdex-PC5. The histograms show that the crosslinked conjugate has 3.5-fold higher fluorescence intensity on CD8αβ+ lymphocytes.

In another run, it was found that the mean channel fluorescence intensity of labeled T cells could be enhanced up to 8-fold by examining various fractions of trial 1, CD8αβ-5X-Amdex-PC5 conjugate as the fluorescent marker. Titers of the control, CD8αβ-PC5, and the sample, CD8αβ-5X-Amdex-PC5, with the same instrument settings were run and the results, mean channel PC5 fluorescence intensities and MFI ratios, sample fraction-to-control at same titers, are presented in Table 23 for another normal donor.

TABLE 23

| CD8αβ, µg | Control | Fraction | | | | | | |
|---|---|---|---|---|---|---|---|---|
| | | 36 | 37 | 38 | 39 | 40 | 41 | 42 | 43 |
| Mean Channel PC5 Fluorescence Intensities ||||||||||
| 3 | 53 | 265 | 325 | 379 | 419 | 376 | 377 | 381 | |
| 2.5 | 53 | 282 | 303 | 352 | 334 | 335 | 357 | 368 | |
| 2 | 55 | 236 | 266 | 302 | 293 | 311 | 319 | 320 | |
| 1.5 | 51 | 194 | 226 | 252 | 240 | 213 | 265 | 292 | 336 |
| 1 | 50 | 174 | 196 | 178 | 183 | 166 | 197 | 216 | 262 |
| 0.5 | 51 | 93 | 130 | 134 | 132 | 155 | 112 | 117 | 177 |
| MFI Ratios, Fraction/Control ||||||||||
| 3 | 1.0 | 5.0 | 6.1 | 7.1 | 7.9 | 7.1 | 7.1 | 7.1 | |
| 2.5 | 1.0 | 5.3 | 5.7 | 6.6 | 6.3 | 6.3 | 6.7 | 6.9 | |
| 2 | 1.0 | 4.3 | 4.8 | 5.5 | 5.3 | 5.7 | 5.8 | 5.8 | |
| 1.5 | 1.0 | 3.8 | 4.4 | 4.9 | 4.7 | 4.2 | 5.2 | 5.7 | 6.6 |
| 1 | 1.0 | 3.5 | 3.9 | 3.6 | 3.7 | 3.3 | 4.0 | 4.3 | 5.3 |
| 0.5 | 1.0 | 1.8 | 2.5 | 2.6 | 2.6 | 3.0 | 2.2 | 2.3 | 3.5 |

Figure 9A:
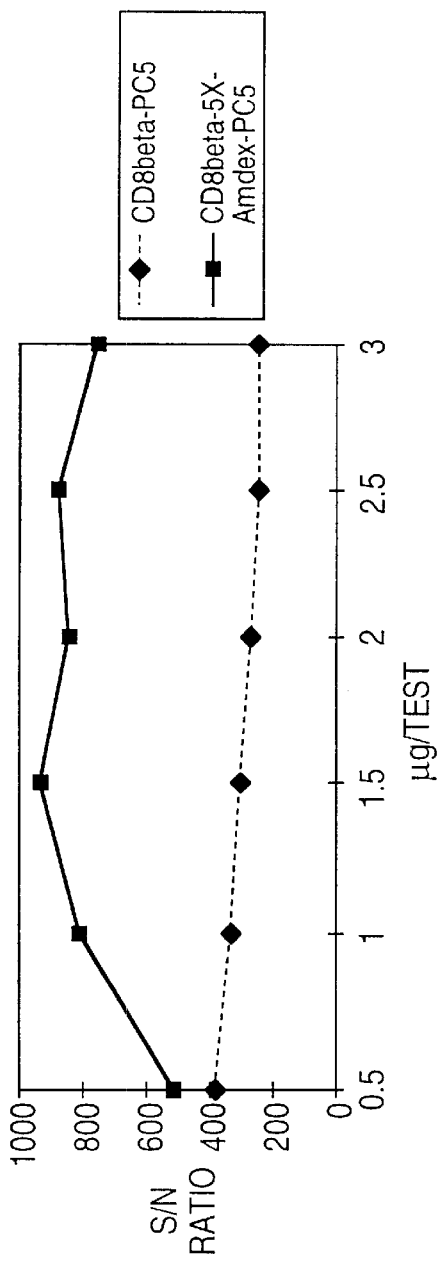
FIG. 9A is a graph plotting signal-to-noise ratio (S/N) for CD8αβ-PC5 ligand (diamond) vs. CD8αβ-5X-Amdex-PC5 ligand (square) for trial 1, fraction 42 of Example 19 below.
Figure 9B:
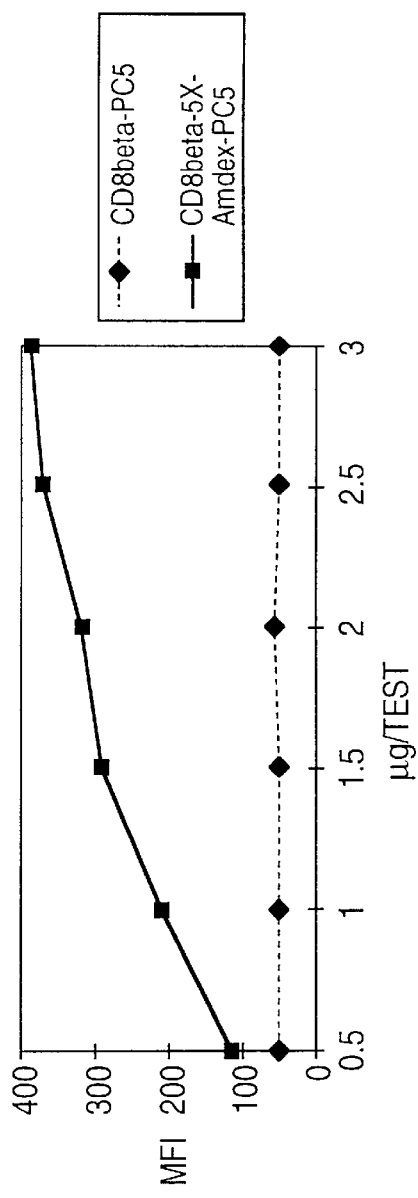
FIG. 9B is a graph plotting positive mean channel intensity for CD8αβ-PC5 ligand (diamond) vs. CD8αβ-5X-Amdex-PC5 ligand (square) for trial 1, fraction 42 of Example 19 below.

MFI ratios corrected for the F/P ratio, 0.860, of the control, direct CD8αβ-PC5 conjugate, were about 16–17% higher than values listed in Table 23. Signal-to-noise and MEI ratios for control versus sample are summarized in the graphs of FIGS. 9A–9B for trial 1, fraction 42.

EXAMPLE 20

Figure 11B:
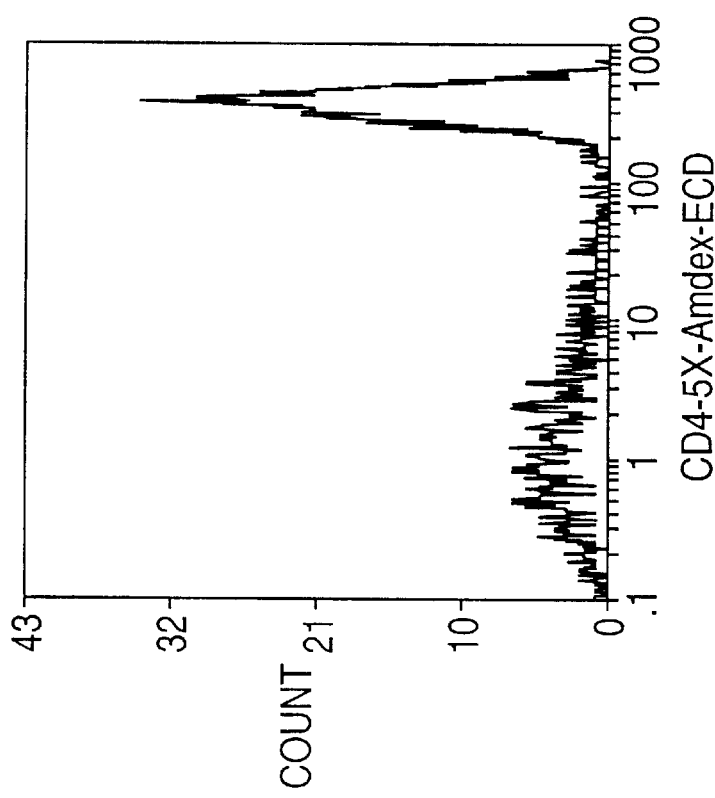
FIG. 11B is a histogram for the 0.03 μg CD4 antibody titer of the CD4-5X-Amdex-ECD ligand.
Figure 11A:
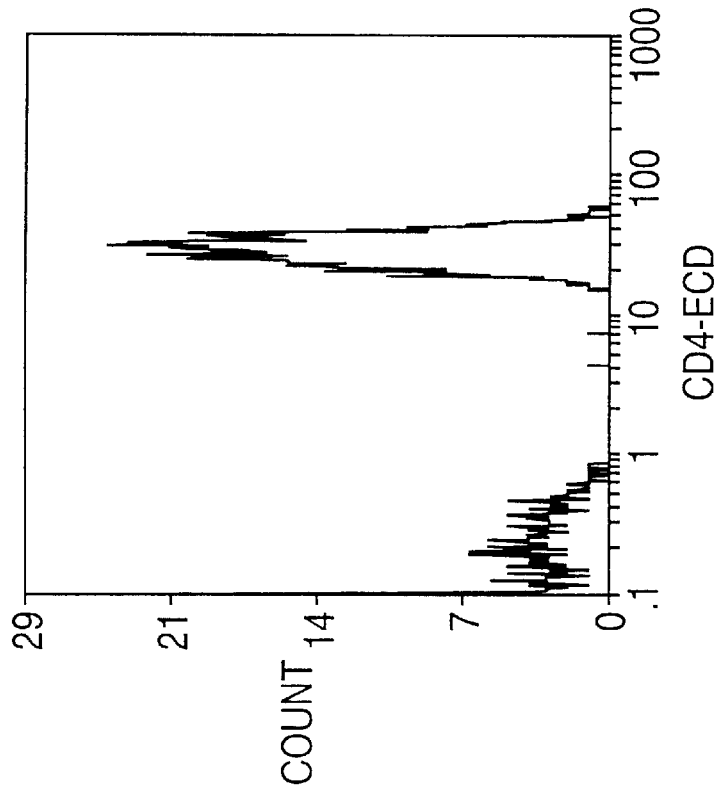
FIG. 11A is a histogram for the 0.03 μg CD4 antibody titer of the CD4-ECD ligand.

Flow Cytometric Analyses of Whole Blood with CD4-ECD and CD4-5X-Amdex-ECD Conjugates CD4-ECD and a single pooled sample of CD4-5X-Amdex-ECD conjugates from trial 2 were titered starting at 0.5 µg (based on ELISA analysis for CD4-5X-Amdex-ECD and $A_{280}$ value for CD4-ECD) per tube in the same way as in the previous example. The results are shown in FIG. 10 for the signal-to-noise ratio and mean channel ECD fluorescence intensities for the CD4+ lymphocytes with the direct and crosslinked antibody-ECD conjugates. The MFI ratios, maximizing at 9.7 were calculated from the mean channel positions. Using the F/P ratio of 0.96 for the CD4-ECD conjugate, the corresponding maximum MFI ratio is 10.1. Representative histograms for the 0.03 μg CD4 antibody titer of each conjugate, CD4-ECD on LHS and CD4-5X-Amdex-ECD on RHS, are displayed in FIGS. 11A–11B.

EXAMPLE 21

Flow Cytometric Analyses of Whole Blood with CD56-PE and CD56-5X-Amdex-PE Conjugates CD56 (NKH-1) antibody conjugates were prepared for use in demonstrating multi-marker, enhanced and non-enhanced PE, flow cytometric analysis. Thus, kg establishment of fluorescence amplification for the CD56-5X-Amdex-PE conjugate was first needed. Titers of the control, CD56-PE at an antibody concentration of 0.125 mg/mL, and the samples, CD56-5X-Amdex-PE from trial 3, starting with 8 μg of antibody per tube, were mixed for 30 min at room temperature with 100 μL whole blood from one blood donor. Concentrations of CD56 antibody in the conjugates were based on $A_{280}$ values. The samples were subjected to Q-PREP lyse and quench, followed by washing with 1×PBS. Mean channel PE fluorescence intensities relative to the control, obtained on the Coulter EPICS XL-MCL flow cytometer with the same instrument settings, are listed in Table 23 and show a maximum enhancement of 14-fold over the control.

TABLE 24

| CD56,μg | Control | 37 | 39 | 40 | 41 | 42 |
|---|---|---|---|---|---|---|
| | | | Fractions | | | |
| Mean Channel PE Fluorescence Intensities | | | | | | |
| 8 | 8 | | | 112 | | |
| 7 | | | 100 | | | |
| 6 | | | | 104 | | |
| 5 | | 82 | | | 88 | |
| 4 | | | | 87 | 75 | |
| 3 | | 65 | 75 | 79 | | 63 |
| 2 | | 50 | 51 | 69 | 65 | 55 |
| 1 | | 25 | | 43 | | 38 |
| 0.5 | | | | | | 29 |
| MFI Ratios, Fraction/Control | | | | | | |
| 8 | 1.0 | | | 14.0 | | |
| 7 | | | 12.4 | | | |
| 6 | | | | 13.0 | | |
| 5 | | 10.3 | | | 11.0 | |
| 4 | | | | 10.8 | 9.3 | |
| 3 | | 8.1 | 9.4 | 9.9 | | 7.8 |
| 2 | | 6.2 | 6.3 | 8.6 | 8.1 | 6.9 |
| 1 | | 3.1 | | 5.3 | | 4.8 |
| 0.5 | | | | | | 3.6 |

EXAMPLE 22

Flow Cytometric Analyses of Whole Blood with CD4-PE and CD4-5X-Amdex-PE Conjugates CD4 antibody conjugates were prepared to obtain an enhanced fluorescence standard with a tight distribution of intensities for lymphocytes. Titers of the control, CD4-PE at a concentration of 0.0625 mg/mL antibody, and the samples, CD4-5X-Amdex-PE from trial 4, starting with 3 μg antibody in the conjugate per tube, were mixed with 100 μL whole blood from a single normal blood donor for 30 minutes at room temperature. Concentrations of CD4 antibody in the conjugates were based on corrected $A_{280}$ values. After the mixing period all samples were submitted to a Q-PREP to lyse red blood cells and quench. The samples were further washed with 1 mL of 1×PBS by centrifugation for 5 minutes at 500 g, discarding the supernatant, and resuspending the cells in 1 mL 1×PBS. Mean channel PE fluorescence intensities relative to the control, obtained with a Coulter EPICS XLMCL flow cytometer at the same instrument settings, are shown in Table 25 and given a maximum MFI ratio of 13.

TABLE 25

| CD4, μg | Con- trol | 36 | 37 | 38 | 39 | 40 | 41 | 42 | 43 |
|---|---|---|---|---|---|---|---|---|---|
| | | | | Fraction | | | | | |
| Mean Channel PE Fluorescence Intensities | | | | | | | | | |
| 3 | 44 | 443 | 499 | 513 | 478 | 471 | 393 | 357 | 298 |
| 2.5 | 42 | 420 | 489 | 507 | 467 | 482 | 392 | 371 | 323 |
| 2 | 42 | 393 | 451 | 463 | 425 | 448 | 396 | 362 | 319 |
| 1.5 | 42 | 352 | 379 | 384 | 412 | 425 | 376 | 355 | 321 |
| 1 | 41 | 281 | 296 | 293 | 343 | 331 | 319 | 327 | 316 |
| 0.5 | 40 | 78 | 220 | | 234 | 269 | 265 | 265 | 273 |
| MFI Ratios, Fraction/Control | | | | | | | | | |
| 3 | 1.0 | 11.0 | 12.4 | 12.7 | 11.9 | 11.7 | 9.7 | 8.8 | 7.4 |
| 2.5 | 1.0 | 10.4 | 12.1 | 12.6 | 11.6 | 12.0 | 9.7 | 9.2 | 8.0 |
| 2 | 1.0 | 9.7 | 11.2 | 11.5 | 10.5 | 11.1 | 9.8 | 9.0 | 7.9 |
| 1.5 | 1.0 | 8.7 | 9.4 | 9.5 | 10.2 | 10.5 | 9.3 | 8.8 | 8.0 |
| 1 | 1.0 | 7.0 | 7.3 | 7.3 | 8.5 | 8.2 | 7.9 | 8.1 | 7.8 |
| 0.5 | 1.0 | 1.9 | 5.5 | | 5.8 | 6.7 | 6.6 | 6.6 | 6.8 |

EXAMPLE 23

Use of Dual Intensity, Same Color Markers in Flow Cytometric Analyses

Figure 12A:
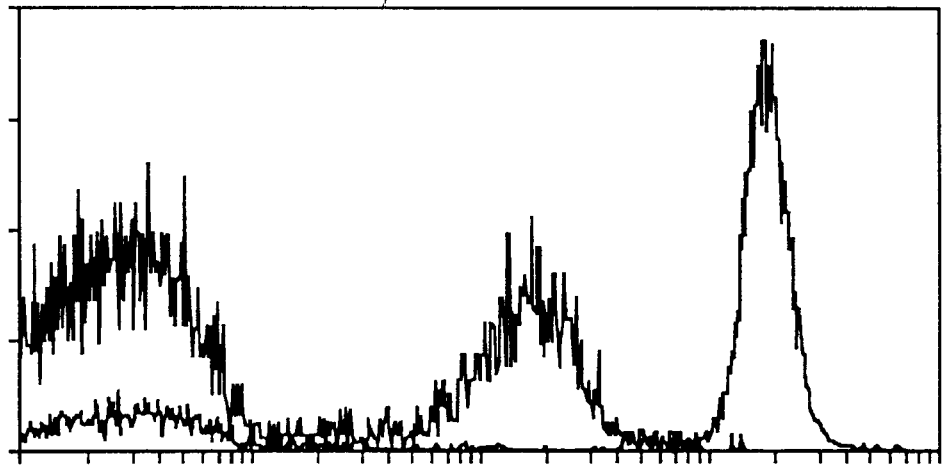
FIG. 12A is an overlay of two single color histograms showing the possible enumeration of mutually exclusive populations (CD56+ and CD4+) of white blood cells in whole blood with one direct fluorescent label-antibody conjugate (CD56-PE) and another enhanced, aminodextran-crosslinked fluorescent label-antibody conjugate of the same fluorescent label (CD4-5X-Amdex-PE) run with 488.0 nm $Ar^+$ laser excitation on a Coulter XL flow cytometer.
Figure 12B:
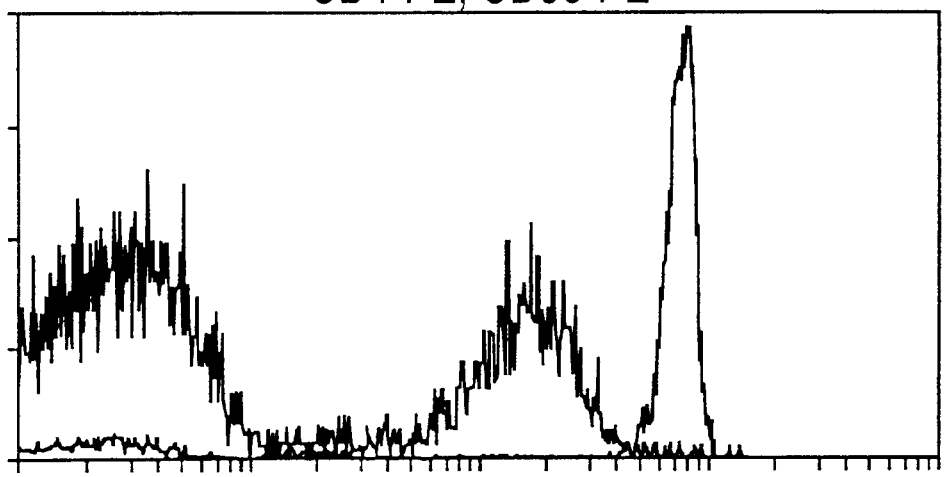
FIG. 12B is a similar set of histograms as for FIG. 12A, but obtained by using the pair of direct conjugates, CD56-PE and CD4-PE, showing some overlap between the CD56+ and CD4+ distributions.
Figure 13A:
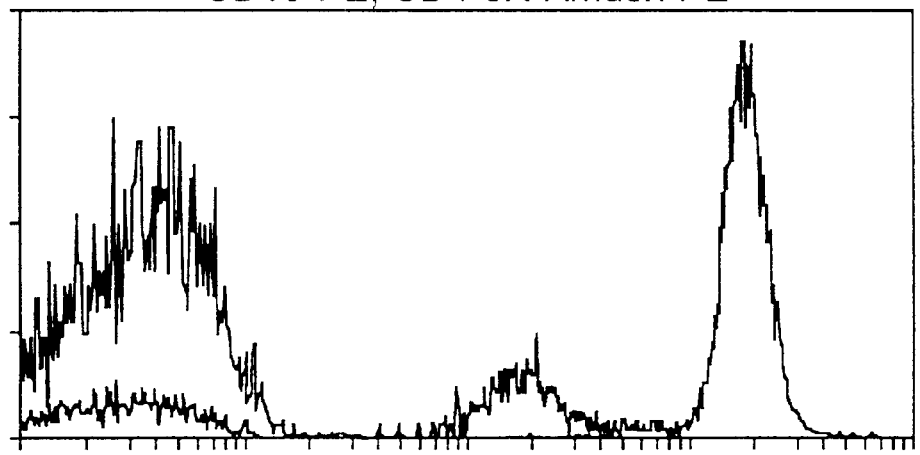
FIG. 13A is a histogram similar to that of FIG. 12A for pairs of markers, CD19-PE and CD4-5X-Amdex-PE.
Figure 13B:
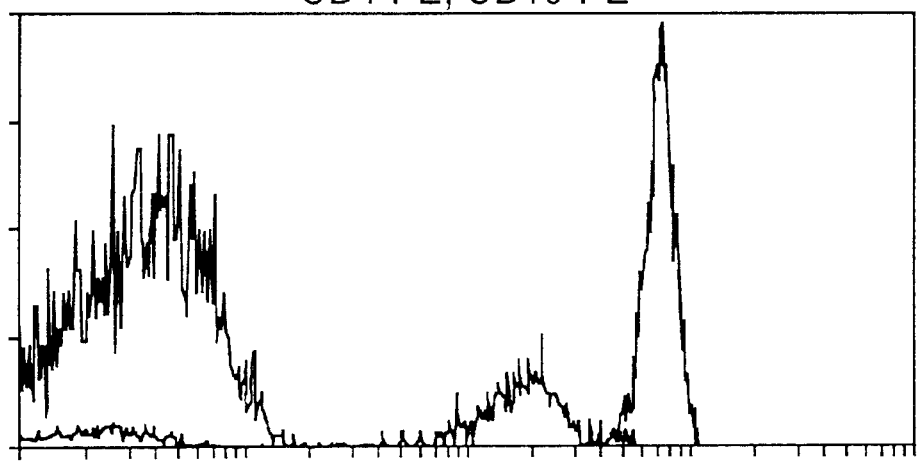
FIG. 13B is a histogram similar to that of FIG. 13A for two directly conjugated pairs of markers, CD19-PE and CD4-PE.
Figure 14A:
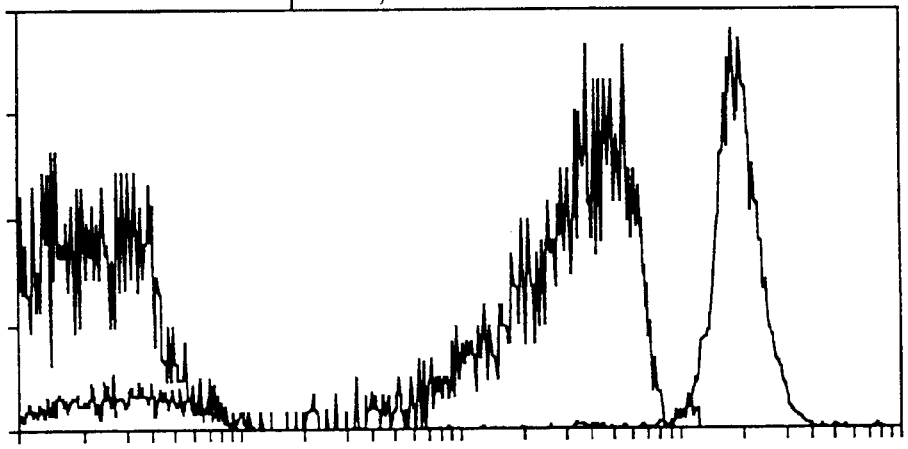
FIG. 14A is a histogram similar to that of FIG. 13A for pairs of markers, CD8αβ-PE and CD4-5X-Amdex-PE.
Figure 14B:
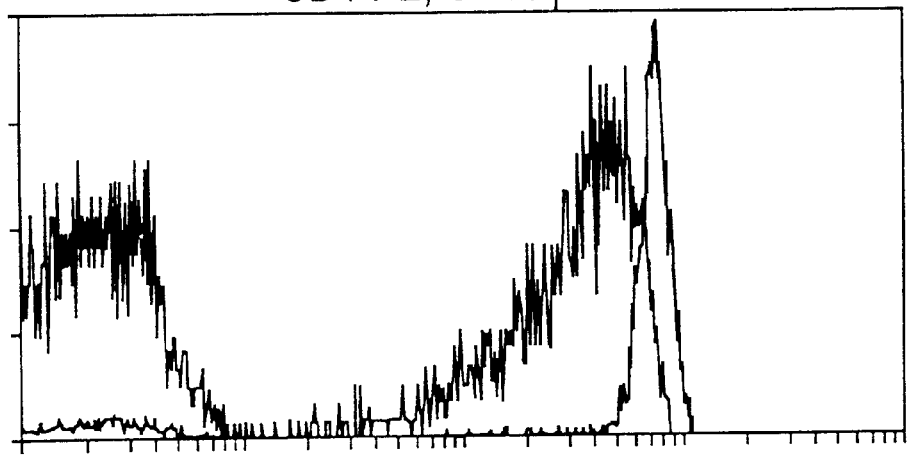
FIG. 14B is a histogram similar to that of FIG. 14A for two directly conjugated pairs of markers, CD4-PE and CD8αβ-PE.
Figure 15A:
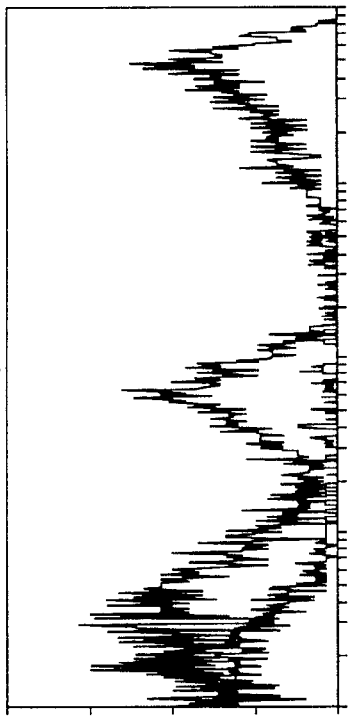
FIG. 15A is a histogram similar to that of FIG. 14A using markers CD56-PC5 and CD8αβ-5X-Amdex-PC5.
Figure 15B:
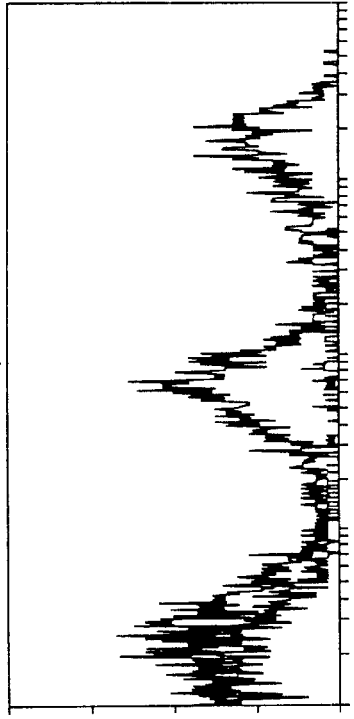
FIG. 15B is a histogram similar to that of FIG. 15A, but obtained with a different titer of the CD8αβ-5X-Amdex-PC5 marker to show optimum separation between the position of the positive and negative count versus intensity distributions.
Figure 15C:
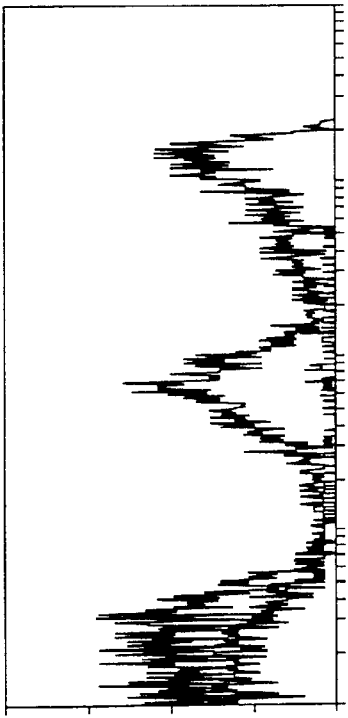
FIG. 15C is a histogram similar to that of FIG. 15A using markers CD8αβ-PC5 and CD56-PC5.
Figure 16A:
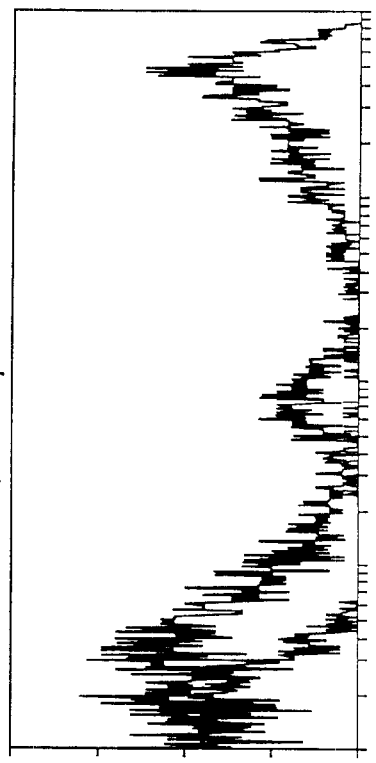
FIG. 16A is a histogram similar to that of FIG. 15A using markers CD19-PC5 and CD8αβ-5X-Amdex-PC5.
Figure 16B:
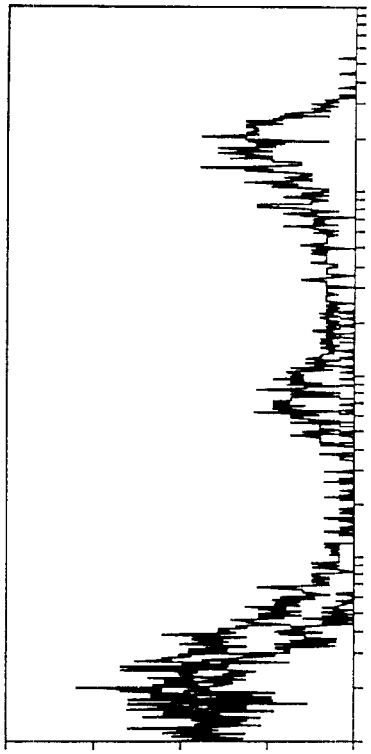
FIG. 16B is a histogram similar to that of FIG. 16A, but obtained with a different titer of the CD8αβ-5X-Amdex-PC5 marker to show optimum separation between the position of the positive and negative count versus intensity distributions.
Figure 16C:
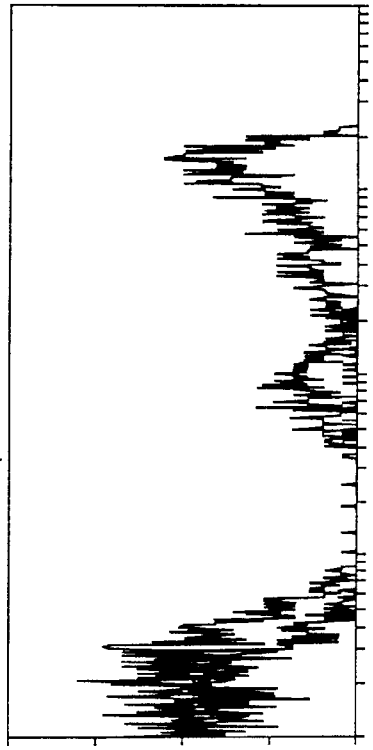
FIG. 16C is a histogram similar to that of FIG. 15C using markers CD8αβ-PC5 and CD19-PC5.
Figure 17A:
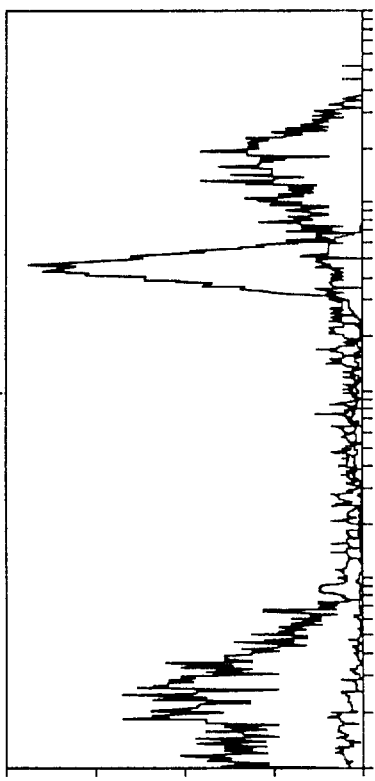
FIG. 17A is a histogram similar to that of FIG. 15A using markers CD4-PC5 and CD8αβ-5X-Amdex-PC5.
Figure 17B:
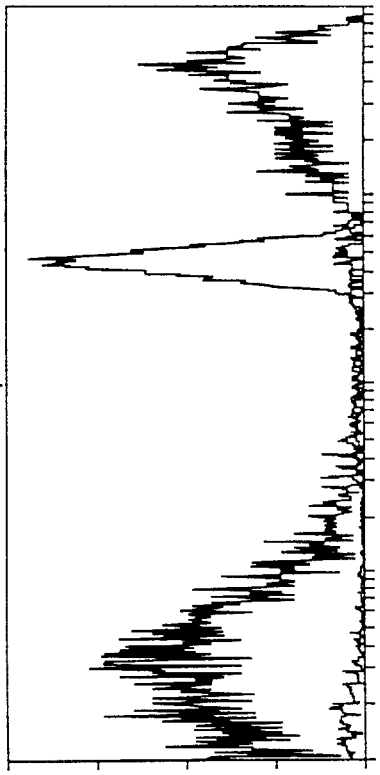
FIG. 17B is a histogram similar to that of FIG. 17A, but obtained with a different titer of the CD8αβ-5X-Amdex-PC5 marker to show optimum separation between the position of the positive and negative count versus intensity distributions.
Figure 17C:
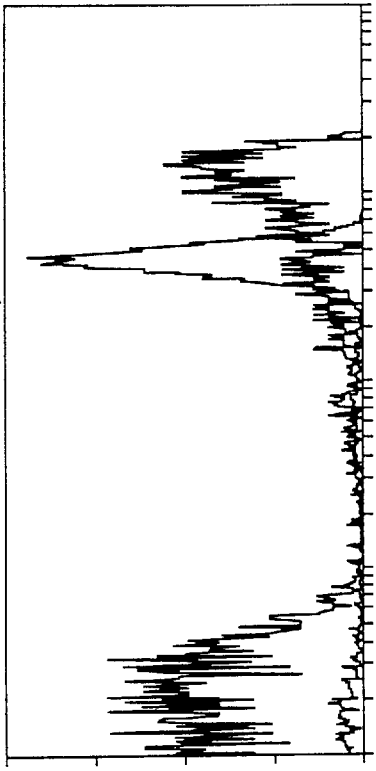
FIG. 17C is a histogram similar to that of FIG. 16C using markers CD4-PC5 and CD8αβ-PC5.

A. Overlayed Single Histograms of Pairs of Same Color Fluorescent Markers—Direct versus Enhanced Label The ability to enumerate mutually exclusive populations of white blood cells in whole blood with one direct fluorescent label-antibody conjugate and another enhanced, aminodextran-crosslinked fluorescent label-antibody conjugate of the same fluorescent label, is demonstrated in the following examples run with 488.0 nm $Ar^+$ laser excitation on a Coulter EPICS XL-MCL flow cytometer. The first pair of markers is CD56-PE and CD4-5X-Amdex-PE, used to obtain the single color histograms that were overlayed and are shown in FIG. 12A. The amplified and narrowly-distributed CD4+ population in the fourth decade of the fluorescence intensity scale is well-separated from the intrinsically weak and broader CD56+ population bordering the second and third decades of the intensity scale. Also, note that the background fluorescence from the CD4+ cells does not interfere with the signal from the CD56+ cells. A similar set of histograms obtained by using the pair of direct conjugates, CD56-PE and CD4-PE, is displayed in FIG. 12B and shows some overlap between the CD56+ and CD4+ distributions.

Similar overlayed histograms are shown in FIGS. 13A through 14B for pairs of markers, CD19-PE and CD4-5X-Amdex-PE, CD8αβ-PE and CD4-5X-Amdex-PE, and in FIGS. 15A through 17C for CD56-PC5 and CD8αβ-5X-Amdex-PC5, CD19-PC5 and CD8αβ-5X-Amdex-PC5, CD4-PC5 and CD8αβ-5X-Amdex-PC5. FIGS. 15B, 16B and 17B show histograms obtained with a different titer of the CD8αβ-5X-Amdex-PC5 marker to show optimum separation between the peaks in the labeled cell count versus fluorescence intensity distributions.

Further combinations of CD4-PE, CD19-PE, or CD8αβ-PE marker with CD56-5X-Amdex-PE marker did not yield favorable separation due to the intrinsically broad intensity distributions for CD56 positive and negative populations of cells, and generally lower numbers of CD56 receptors per cell compared to CD4+ or CD8αβ+ receptors per cell. Thus, when a higher intensity marker is used with an enhanced CD56 marker, the overlap between CD56 and CD4 or CD8αβ intensity distributions is even greater.

Figure 18A:
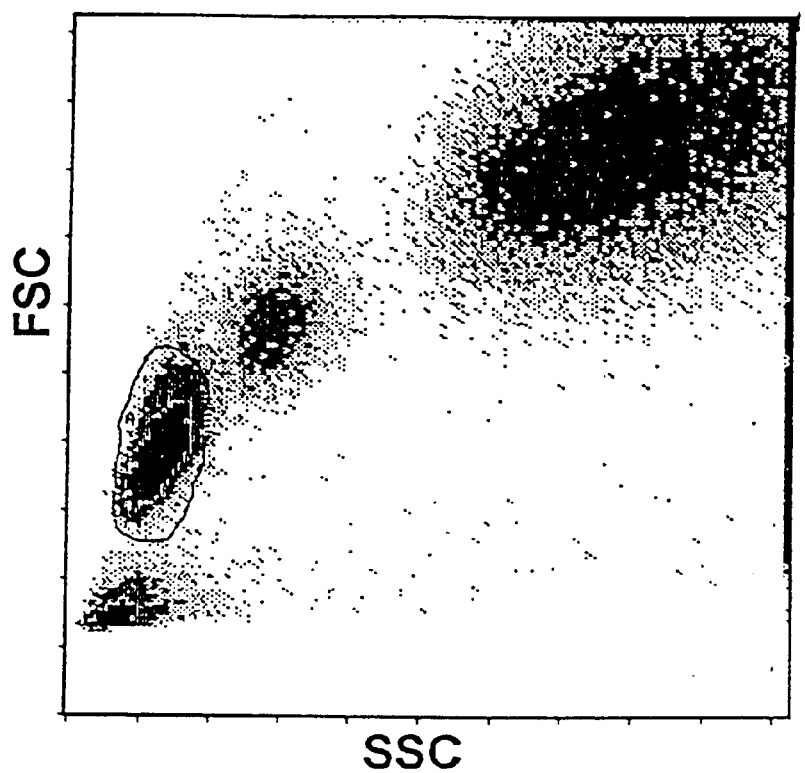
FIG. 18A is the FS versus SS histogram from two direct fluorochrome-antibody conjugates, CD56-PE and CD19-PC5, and two aminodextran crosslinked conjugates, CD4-5X-Amdex-PE and CD8αβ-5X-Amdex-PC5, used simultaneously to analyze for CD56+ (NK cells), CD4+ (T4 cells), CD19+ (B cells), and CD8αβ+ (T8 cells) in the scatter-gated lymphocyte population of white blood cells of a normal blood donor run with 488.0 nm Ar+ laser excitation on the Coulter XL flow cytometer.
Figure 18B:
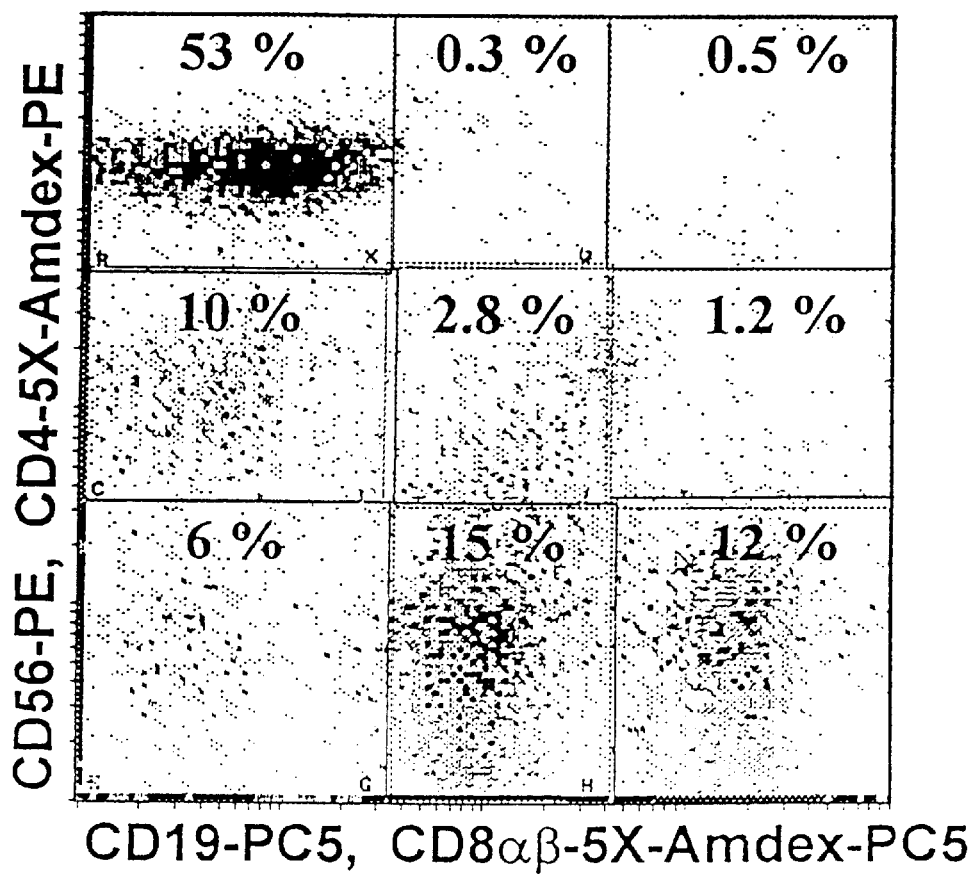
FIG. 18B is a dual color PE(CD56/CD4-5X-Amdex) versus PC5(CD19/CD8αβ-5X-Amdex) fluorescence intensity histogram of the experiment of FIG. 18A.
Figure 19:
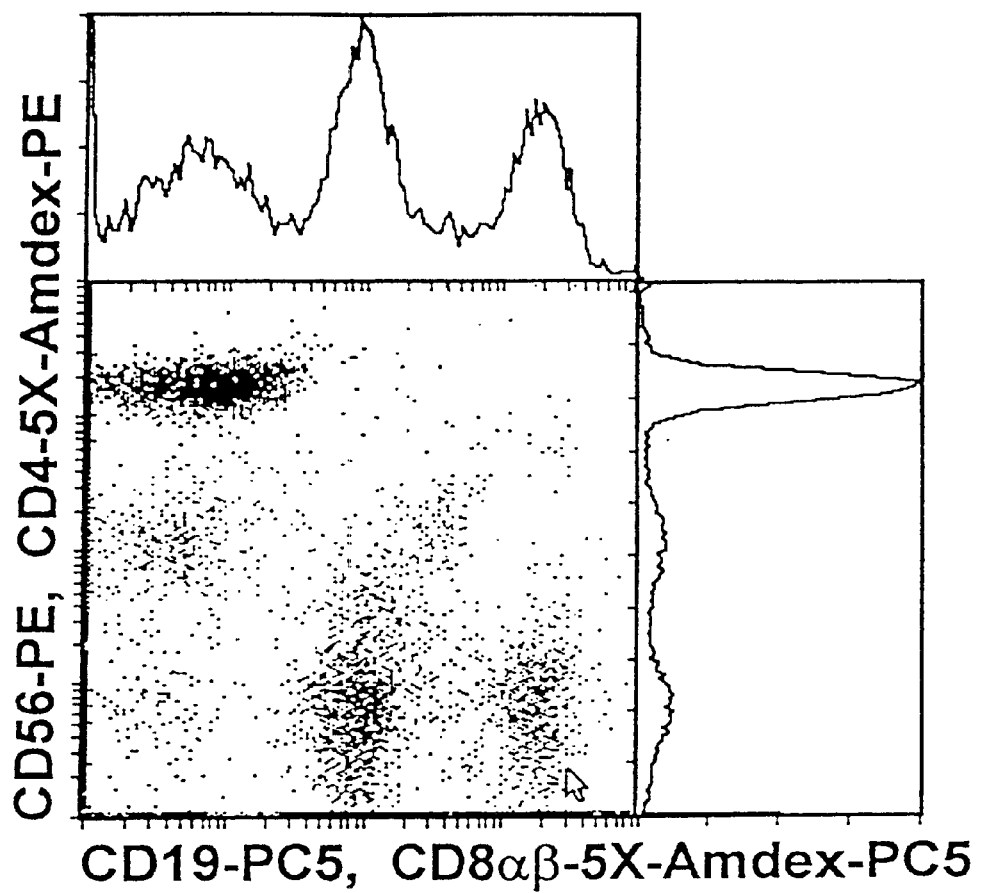
FIG. 19 is projection display of the dual parameter display of PE vs. PC as a single color cell count versus PC5(CD19/CD8αβ-5X-Amdex) fluorescence intensity histogram and the single color count versus PE (CD56/CD4-5X-Amdex) fluorescence intensity histogram. The two single color histograms which form the upper histogram and right histogram of this figure, each contain one direct fluorochrome-antibody marker and an enhanced intensity, aminodextran-crosslinked, marker of the same color. These show good separation of the enhanced marker in the fourth decade of the fluorescence intensity scale from the usual marker with maximum mean channel fluorescence intensity in the second or third decade.
Figure 20A:
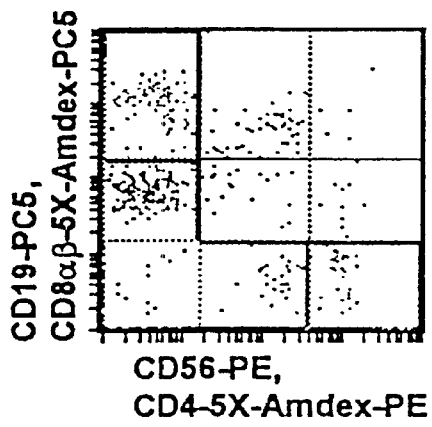
FIGS. 20A–20D represent the set of dual parameter histograms from a six marker, four color, single stain experiment.
Figure 20B:
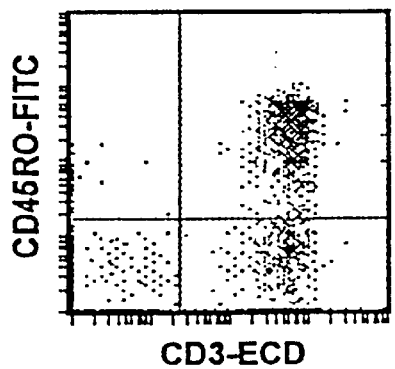
Figure 20C:
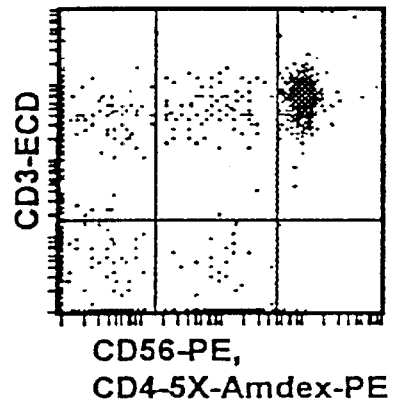
Figure 20D:
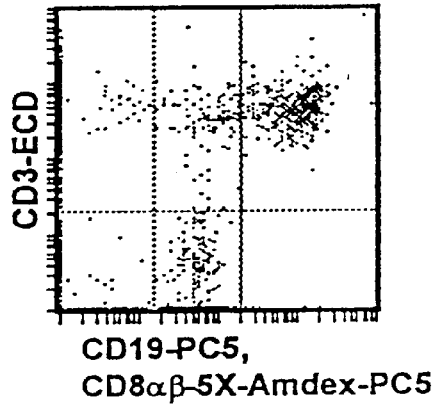
Figure 21A:
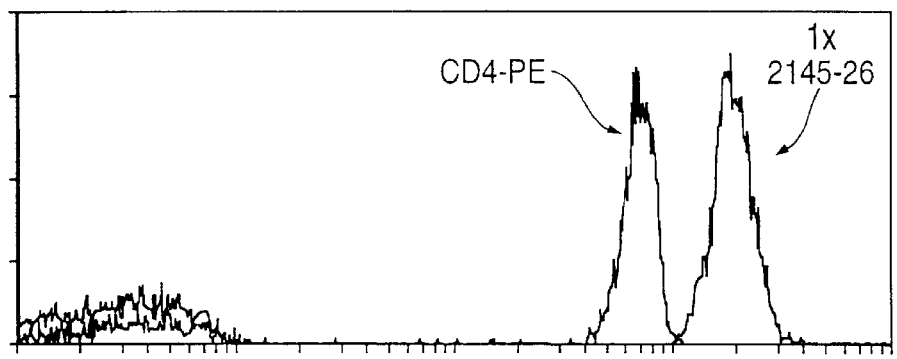
FIG. 21A is a flow cytometry histogram of the number of fluorescence event versus mean channel fluorescence intensity for CD4-PE and CD4-1x Amdex (lot 2145-26)-PE labelled lymphocyte.
Figure 21B:
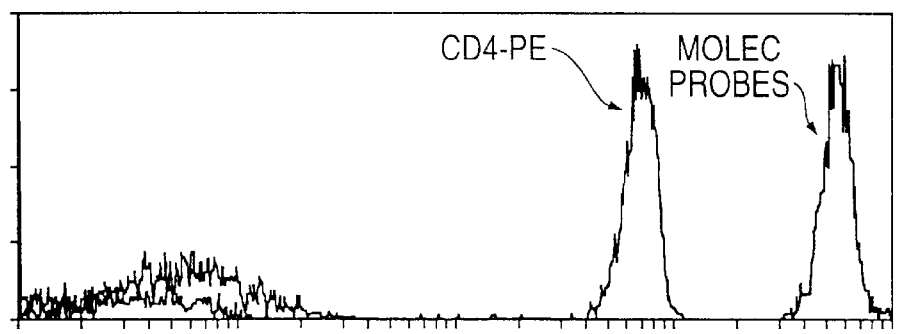
FIG. 21B is a flow cytometry histogram of the number of fluorescence event versus mean channel fluorescence intensity for CD4-Amdex(Molecular Probe (M.P.))-PE labelled lymphocytes.
Figure 21C:
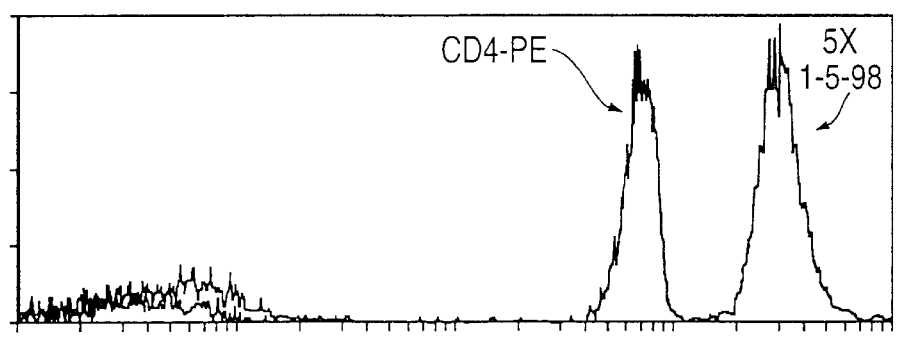
FIG. 21C is a flow cytometry histogram of the number of fluorescence event versus mean channel fluorescence intensity for CD4-PE and CD4-5x-Amdex-PE labelled lymphocytes.
Figure 21D:
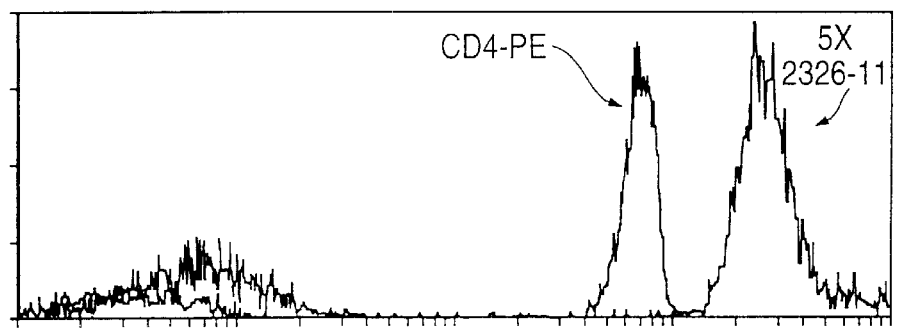
FIG. 21D is a flow cytometry histogram of the number of fluorescence event versus mean channel fluorescence intensity for CD4-PE and CD4-1x-Amdex (lot 2326-11)-PE labelled lymphocyte.

B. Use of Four Markers, Dual Color, with Single Laser Excitation Line in Flow Cytometric Analysis Two direct fluorochrome-antibody conjugates, CD56-PE and CD19-PC5, and two aminodextran crosslinked conjugates, CD4-5X-Amdex-PE and CD8αβ-5X-Amdex-PC5, were used simultaneously to analyze for CD56+ (NK cells), CD4+ (T4 cells), CD19+ (B cells), and CD8αβ+ (T8 cells) in the scatter-gated lymphocyte population of white blood cells of a normal blood donor run with 488.0 nm Ar$^+$ laser excitation on the Coulter EPICS XL-MCL flow cytometer. The FS versus SS and dual color,PE (CD56/CD4-5X-Amdex) versus PC5 (CD19/CD8αβ-5X-Amdex) fluorescence intensity histograms are shown in FIGS. 18A and 18B. Also cell count versus PC5 (CD19CD8αβ-5X-Amdex) fluorescence intensity histograms are shown in the projection display in FIG. 19. The two single color projection histograms (n the upper and right hand side of this figure), each containing one direct fluorochrome-antibody marker and an enhanced intensity, aminodextran-crosslinked, marker of the same color, show good separation of the enhanced marker in the fourth decade of the fluorescence intensity scale from the usual marker with maximum mean channel fluorescence intensity in the second or third decade. As labeled on the histograms of FIG. 18B, the positive CD56, CD4, CD19, and CD8αβ cell populations account for 90% of events displayed on the dual color histogram.

C. Use of Six Markers, Four Color with Single Laser Excitation Line in Flow Cytometric Analysis Two additional color markers, CD3-ECD and CD45RO-FITC were mixed with whole blood already containing the dual color, four markers CD56-PE/CD4-5X-Amdex-PE and CD19-PC5/CD8αβ-5X-Amdex-PC5. The Q-PREPed and washed samples were run with 488.0 nm Ar$^+$ laser excitation on the Coulter EPICS XL-MCL flow cytometer; then, the sets of histograms in FIGS. 20A through 20D, demonstrating resolution of 25 different targeted white blood cell populations were obtained. Furthermore, seven marker, four color analysis could be obtained with a single laser excitation line by adding the pair of markers, CD16-ECD and CD3-5X-Amdex-ECD, instead of CD3-ECD in the six marker experiment.

EXAMPLE 24

Preparation of Additional Aminodextrans

A. Preparation of 1X- to 5X-Substituted Aminodextrans.

This was performed essentially as described above and in recently issued patents, U.S. Pat. No. 5,639,620 and U.S. Pat. No. 5,707,877.

Four lots of 1X-Amdex, that were used in trials for preparation of T4-1X-PE and T8β-1X-PC5 conjugates, showed elemental analyses as listed in Table 26, from which were calculated the figures for the degree of substitution with two propanediamine groups per reacted glucose unit of dextran:

TABLE 26

| Lot No. | % C | % H | % N | % O by diff. | deg. of subst. |
|---|---|---|---|---|---|
| −2213-18 | 40.49 | 6.58 | 0.69 | 52.24 | 1/44.8 |
| −2145-26 | 42.53 | 6.52 | 1.01 | 49.94 | 1/31.9 |
| −2249-50 | 43.58 | 6.50 | 0.82 | 49.10 | 1/40.5 |
| −2326-75 | 43.05 | 6.68 | 1.17 | 49.54 | 1/27.8 |

The molecular weight of lot -2326-75 1X-Amdex was ~1M Da as determined by the Viscotek (Houston, Tex.) triple detection (refractive index, viscosity, light scatter) system. The Viscotek triple detection system consists of a model T-60 differential viscometera/light scattering dual detector and a model LR40 differential laser refractometer with a 670.0 nm diode laser source. The principles of the method and analyses have been described in M. A. Haney et al., *Today's Chemist at Work*, 3(11):39–43 (1994) and I. Hall et al., *Adv, Chitin Sci.*, 1:361–371 (1996). See, Example 34 for more detail.

Dextran, amino, nominally of 2,000,000 MW, Cat. No. D-7145, was purchased from Molecular Probes, Inc., Eugene, Oreg. Analytical data for lot 6551-3: 130 amines/mole. Measurement of the molecular weight of this lot of aminodextran by the Viscotek triple detection system gave ~3M Da. Therefore, there are 3,000,000 g/mol÷162.1 g/mol glucose monomer =18,507 glucose units/dextran molecule or 130/18,507=0.00702, i.e. ~1/142 degree of substitution with single amine group per reacted glucose unit. A single lot of Amdex was used in three conjugations to prepare T4-Amdex-PE, T8β-Amdex-PC5, and T4-Amdex-ECD conjugates.

B. Preparation of Crosslinked 5X-Aminodextran

T-2M dextran, 500 g, 3.08 mol (Sigma, St. Louis, Mo.) was transferred to a one gallon Waring blendor Model CB6 commercial, stainless steel bowl containing 5000 mL of distilled water. The mixture was blended at ½ maximum speed until all the white solid of dextran was dissolved, typically for about 5 minutes. A solution of 267.5 g, 1.25 mol of sodium m-periodate (NaIO$_4$, Sigma) in 2000 mL distilled water was added to the dextran solution over a 5–15 minute period using vigorous overhead stirring in a five gallon cylindrical tank. After the periodate addition was completed, the reaction mixture was stirred at room temperature for about an additional four hours. About 5000–6000 mL distilled water were further added to the reaction mixture over the four hour period to reduce the viscosity of the solution. After the four hours, the 12L reaction volume had an initial specific conductivity of 7.40 mmho-cm$^{-1}$ and an initial pH of 2.65. The reaction mixture was a then desalted using a hollow fiber cartridge, A/G Technology Corp. model UFP-5-E-35, 5,000 molecular weight cut-off or model UFP-30-E-35, 30,000 molecular weight cut-off, with tubing adaptor kit, KA12-3P. Washing was done using about 100 liters of distilled water to obtain 6000 to 9000 mL of washed, oxidized dextran solution having a specific conductance of about 6–20 μmho-cm$^{-1}$ and pH of 6.5–7.0.

Since the dextran aldehyde solution is prone to gelation at ambient temperature, it was first made certain that the dextran aldehyde was completely dissolved before adding 1,3-diaminopropane, DAP (Aldrich). Then, the first portion of DAP, 70 mL of pure liquid, was added over about 5 minutes to the desalted, oxidized dextran solution. The resulting solution immediately began to show formation of a gel, which persisted for another 5–10 minutes before redissolving as a yellow solution. The reaction mixture was then put on an ice bath to maintain a reaction temperature of 8–10° C. and stirred vigorously before a second portion of 70 mL DAP was added over a period of 5 minutes. After an additional 10 minutes of stirring, the third and final 70 mL portion of DAP was added to the reaction mixture. The total DAP addition and reaction time was 45 minutes. Then, 70 g, 5.00 mol, of sodium borohydride in 700 mL of 1 mM aqueous potassium hydroxide solution were added to the reaction mixture at 8–10° C. over about 10–15 minutes with overhead stirring. After the sodium borohydride addition was completed, the reaction mixture was stirred for an additional two hours until the yellow Schiffs' base color had disappeared. The reaction mixture was then desalted using the hollow fiber cartridge. In one run at a total volume of 7500 mL, the initial specific conductance was 30.3 mmho-$cm^{-1}$ and the initial pH was 11.79. About 80L of distilled water were used to produce about 1600 mL of crosslinked 5X-aminodextran solution having a specific conductance of 10–20 $\mu$mho-$cm^{-1}$ and pH of 7.0–8.0. The aminodextran solution was filtered through a 1.6 $\mu$m glass filter and lyophilized for a minimum of 72 hours in a model TDS-00030-A, Dura-Dry microprocessor-controlled freeze-drier (FTS Systems, Inc.) to produce 75–90 g (15–18% yield) of flaky, white to pale yellow crystals.

The periodate oxidation of glucose units in dextran produced by *Leuconosioc mesenteroides* NRRL B-512 was shown in A. Jeanes and C. A. Wilham, *J. Amer. Chem. Soc.*, 72, 2655–2657(1950) and the Structure of Nrri B-512 Dextran. Methylation Studies, J. W. Van Cleve, W. C. Schaefer, and C. E. Rist *J. Amer. Chem. Soc.* 78, 4435–4438(1956), to release one mole of formic acid per mole of reacted glucose unit by 95% of the anhydroglucose residues. Thus, the overall redox equation for a two-step periodate oxidation reaction is $$2IO_4^- + C_6H_{10}O_5 \rightarrow 2IO_3^- + C_5H_6O_4 + HCOOH + H_2O,$$

requiring 2 mol periodate per 1 mol glucose unit or 2 mol aldehyde for complete reaction. However, only 1 mol periodate per 2.5 mol glucose units or 2 mol periodate per 5 mol glucose units were used so that the theoretical degree of substitution is 1/5, i.e., 1 glucose unit out of 5 units in dextran is substituted with 2 aldehyde groups. Thus, the maximum degree of substitution of dextran with DAP is also 1/5, i.e., 1 in 5 glucose units in dextran is substituted with 2 DAP groups, assuming no crosslinking of aldehyde groups by DAP.

A comparison of characteristics of representative 5X-Amdex lots is summarized in Table 27.

TABLE 27

| Lot No. | Dextran scale | DAP reaction | 5X-Amdex yield | % N | degree of subst.* | Yield of Ab, PE conjugates |
|---|---|---|---|---|---|---|
| 2326-11 | 500 g | 3 portions | 75 g | 3.79 | 1/8.3 | good–excellent |
| 2326-69 | 300 | 3 portions | 95 | 3.91 | 1/7.7 | partial |
| 2776-75 | 300 | 1 portion | 62 | 4.50 | 1/7.1 | none |
| 2847-15 | 300 | 1 portion, 4X | 74 | 3.10 | 1/9.5 | none |
| 11/6/97 | 100 | 3 portions, pH 8.5 with aq. HCl | 52 | 4.44; 2.81% Cl | 1/6.1 | none |
| 11/6/97, ion exch. & acet. fract. | | | | 3.82; <0.5% Cl | 1/8.3 | partial |
| 1/5/98 | 500 | 3 portions | 87 | 4.15 | 1/6.9 | good |
| 2/2/98 | 500 | 2 portions, ~1/3 DAP | 45 | 3.48 | 1/8.2 | poor, like 1X-Amdex |

*not corrected for any crosslinking

All lots were membrane-filtered with a 5,000 Da molecular weight cut-off hollow fiber cartridge except the 2/2/98 lot for which a 30,000 Da molecular weight cut-off cartridge was used. Some 5X-Amdex lots require further description. In particular, the reaction mixture of the 11/6/97 lot, after addition of DAP and sodium borohydride, was adjusted to pH 8.5 with aqueous hydrochloric acid. It was then desalted, concentrated, and freeze-dried in the previously described manner. Elemental analyses for 5X-Amdex, 11/6/97 were C=39.72%, H=7.77%, N=4.44%, Cl=2.81%, O (by difference)=45.26%. The empirical formula based on actual analyses was $C_{10.4}H_{24.3}O_{8.9}NCl_{0.25}$. The chloride analysis showed that 1 out of 4 total amine (primary and secondary) groups had a chloride counterion. Assuming only primary amine groups would be protonated near neutral pH to which the reaction mixture was desalted prior to lyophilization, this implies that 50% of the diaminopropane groups in aminodextran are bridging or crosslinking groups between dextran chains. These bridging DAP groups contain only two secondary amino groups. Thus, idealized repeating units for solely the substituted glucose residues of aminodextran would An contain the following sequences:

(a) 1 bridging DAP, 2 non-bridging DAP; 2 bridging DAP; 2 non-bridging DAP, 1 bridging DAP;

(b) 2 bridging DAP; 2 bridging DAP; 4 non-bridging DAP; or some permutation of either of the (a) or (b) sequences.

A portion of the lyophilized aminodextran hydrochloride was dissolved in distilled water and deionized in batchwise fashion with mixed bed ($H^+$, $OH^-$ form), Bio-Rad AG 501-X8 resin, until the specific conductivity of the supernatant was minimized. The resin was removed by filtration of the suspension through rayon cloth and the aminodextran (~50 mg/mL) in the filtrate was fractionated by precipitation with acetone (0–43% cut). The solid precipitate was washed with acetone and dried in a vacuum dessicator under silica gel. Elemental analyses of this deionized and fractionated material gave C=45.55%, H=7.03%, N=3.82%, Cl<0.5%, O (by difference)=43.60%, showing that chloride ion had been removed in the above process.

Elemental analyses for the 2326-11, 5X-Amdex lot which gave the best yield of conjugates were C=44.45%, H=7.20%, N=3.79%, O (by difference)=44.56%. The empirical formula was $C_{13.7}H_{26.9}O_{10.3}N$, which is similar to the formula $C_{13}H_{24}O_9N \cdot H_2O$ based on 5 units of glucose per one unit of 1.5 diaminopropane-substituted sugar ring ($C_{9.5}H_{21}O_2N_3$), or a degree of substitution in dextran of ⅙. Analyses for the 1598 5X-Amdex lot which gave a good yield of conjugates were C=41.38%, H=7.81%, N=4.15%, O=45.64%, I=97 ppm, B=590 ppm. The empirical formula was $C_{11.6}H_{26.1}O_{9.6}N$, which is similar to the formula $C_{11.2}H_{20.3}O_{7.3N} \cdot 2H_2O$ based on 4 units of glucose per one unit of 1.5 diaminopropane-substituted sugar ring. Thus, the degree of diamine substitution in dextran was ⅕, which agreed well with the figure calculated for the theoretical degree of substitution. Measurement of the molecular weights of lot 2326-11 and lot 1/5/98 5X-Amdex by the Viscotek triple detection system gave 400,000 and 70,000 Da, respectively.

Additional reaction conditions of total reaction volume, dextran concentration, and reaction times for preparing lots of crosslinked 5X-Amdex are tabulated in Table 28.

TABLE 28

| Lot No. | Volume | Conc. mg/ml | DAP Rxn. Time | $NaBH_4$ Rxn. Time | 90° LS |
|---|---|---|---|---|---|
| 2326-11 | 7000 mL | 71.4 | 45 min | 2 hrs | $1.2 \times 10^5$ |
| 2326-69 | 6000 | 50.0 | 60 | 2.5 | $8.3 \times 10^4$ |
| 11/6/97 | 1700 | 58.8 | 45 | 2 | $2.5 \times 10^4$ |
| 1/5/98 | 9100 | 54.9 | 45 | 2 | $7.0 \times 10^4$ |
| 2/2/98 | 8000 | 62.5 | 40 | 2 | $6.0 \times 10^4$ |

The optimum conditions for preparing the highest molecular weight cross/linked aminodextran from water-soluble T-2M dextran were obtained at a 500 g dextran scale by concentrating oxidized and desalted dextran aldehyde solution to its lowest volume before gelation occurred at ambient temperature, and then adding DAP in 3 portions to form a thick gel after addition of the first portion, waiting for the gel to dissolve within 15 min, and adding other 2 portions of DAP.

90° light scattering (LS) intensity was measured on the Coulter N4MD Analyzer for all of the above 5X-Amdex lots at 10 mg/mL in a 1 cm path quartz cell with five sides polished and is also listed in Table IV. In addition, 90° LS for starting dextran, T-2M, at 10 mg/mL ranged from $7.4 \times 10^4$ to $1.1 \times 10^5$; and for 1X-Amdex lots at 10 mg/mL, ranged from $2.9–3.7 \times 10^4$. Best results, in preparing conjugates that were most effective in fluorescence amplification, were generally obtained with material which showed the highest light scattering intensity and had been prepared at the highest concentration of oxidized dextran.

EXAMPLE 25

Preparation of Anti-CD8αβ Antibody-PC5 Conjugate

Direct monoclonal antibody (MCA)fluorochrome(PE, PC5, ECD) conjugates are commercially available for most antibodies from Coulter Corporation or Immunotech, as prepared by established procedures of conjugation reactions of iminothiolane activated PE(or PC5; ECD) with sulfo-SMCC activated antibody or sulfo-SMCC activated PE(or PC5; ECD) with DTT(dithioerythreitol) reduced antibody. The molar ratio of MCA:fluorochrome in these conjugates is about 1:1. Conjugation of IgG monoclonal antibody to PC5 was accomplished by sulfosuccinimidyl 4-[N-maleimidomethyl] cyclohexane-1-carboxylate (sulfo-SMCC) activation of PC5 and activation of antibody by reduction of disulfide bonds in the hinge region with dithiothreitol(DTT).

A. Activation of Monoclonal Antibody.

For 50 mg of MCA at a concentration of 14.04 mg/mL, 3.549mL of MCA concentrate were required. A 15.4 mg/mL solution of DTT in 1×PBS was prepared and used at an activation ratio of DTT:MCA=300: 1. Thus, to make a total volume of 10 mL with 5 mg/mL of MCA, 5.451 mL of 1×BBS buffer (20 mM borate, 150 mM sodium chloride, pH 8.8) were placed in a reaction vial, to which were added 3.549 mL of MCA solution with stirring at 25° C. and then slowly added 1.000 mL of DTT solution. The reaction mixture in a vial was incubated at 25° C. for 20 min, after which 2.5 mL of MES (2-[N-morpholino]ethanesulfonic acid) quenching buffer(50 mM MES, 5.0 M sodium perchlorate, 4 mM EDTA (ethylenediaminetetraacetic acid), pH 5.8) were added and the reaction mixture was incubated for an additional 2 min. Then, immediately the activated MCA sample was applied to the top of a 200 mL G-50 Sephadex column, equilibrated with MES column buffer (50 nM MES, 100 mM sodium perchlorate, 4 nM EDTA, pH 6.0). The activated MCA was eluted from the column with MES buffer and fractions of the first peak absorbing at 280 nm were collected. The activated MCA concentration in mg/mL was determined by the $A_{280}$ value. 34 mL of activated MCA solution at 1.394 mg/mL (47.4 mg) were obtained.

B. Activation of PC5 with 2-iminothiolane.

PC5, the PE (R-phycoerythrin(red algae))-5'-cyanine tandem conjugate, was prepared as described in U.S. Pat. No. 5,171,846 issued Dec. 15, 1992. For 55 mg of PC5 at a concentration of 14.69 mg/mL in 1×BBS buffer, 3.744 mL of the PC5 concentrate were required. A 4.5 mg/mL solution of sulfo-SMCC in 1×BBS buffer was prepared and used at an activation ratio of sulfo-SMCC:PC5=40:1. Thus, to make 5 mg/mL of PC5 at a total volume of 11 mL, 5.936 mL of 1×BBS buffer were placed in a reaction vial, to which were added 3.744 mL of PC5 solution with stirring at 25° C. and then, slowly added 0.44 mL of NEM (N-ethyl maleimide, 31.25 mg/mL in 1×BBS buffer) solution. The reaction mixture in the vial was incubated for 30 min. Then, 0.88 mL of sulfo-SMCC solution (4.5 mg/mL) was added to the mixture which was incubated for a further 60 min. At the end of the last incubation period, 1.1 mL of 1M ammonium chloride in 1×BBS buffer were added to the mixture, and further incubated for 2 min. Then immediately the activated PC5 was loaded onto a 200 mL G-50 Sephadex column, equilibrated with MOPS (3-[N-morpholino]propanesulfonic acid) column buffer (50 mM MOPS, 100 mM sodium perchlorate, 4 mM EDTA, pH 7.0). The activated PC5 was eluted from the column with MOPS buffer and the first colored peak off the column was collected. The concentration of 1.962 mg/mL of activated PC5 was determined as $A_{565.5}/8.167$. The activated PC5 was diluted to 1.5 mg/mL with MOPS buffer to give 32.7 mL total volume.

C. Conjugation of MCA with PC5.

For conjugation, equal volumes (32.7 mL) of activated MCA at 1.4 mg/mL and activated PC5 at 1.5 mg/mL were mixed by adding activated MCA into stirring activated PC5. The reaction mixture was incubated at 25° C. for 2 hours. At the end of the mixing period, 2.642 mL of 31.25 mg/mL NEM in 1×BBS buffer were further added to the reaction mixture, which was roller mixed for an additional 5 min.

D. Purification of MCA-PC5 Conjugate.

A Superdex 200 prep grade column (3.4 mL of column per mg of MCA or 318 mL) equilibrated with 1×PBS, 2 mM EDTA, pH 7.2 buffer was prepared. The MCA-PC5 reaction mixture was concentrated to less than 2% of the Superdex 200 column volume, 4.33 mL. The sample was loaded onto the Superdex 200 pg column, and eluted with 1×PBS, 2 mM EDTA, pH 7.2 buffer at 119 mL/hr. The $A_{280}/A_{565.5}$ ratio was calculated for each fraction. All fractions with ratios from 0.43 until two fractions before the free PC5 eluates were pooled. For example, the pooled CD8β-PC5 fractions, 25 mL, were concentrated to a volume of 3.45 mL, less than 1% of the column volume, by using an Amicon YM30 membrane, diafiltering the concentrate with 1×PBS, 0.1% sodium azide, 0.1 mM EDTA buffer, and centrifuging the CD8β-PC5 conjugate at 1800×g for 15 min at 40° C. A 100-fold dilution of this pooled sample gave $A_{565.5}$=0.4809 or (0.4809/8.167)×100=5.888 mg/mL PC5 and 20.31 mg total PC5 in the CD8αβ-PC5 conjugate, and $A_{280}$=0.1513 or [0.4809/5.476 (PC5's $A_{565.5}/A_{280}$)]×100=6.349 mg/mL CD8αβ and 21.90 mg total CD8αβ in the CD8β-PC5 conjugate. The molar ratio of PC5CD8(3 is therefore (20.31 mg PC5/240,000)//(21.90 mg CD8αβ/160,000)=0.618. A corrected F/P ratio based on the formula, MCA:PC5=[$A_{280}/A_{565.5}$ (conjugate)−$A_{280}/A_{565.5}$ (dye)]×8.77, is 0.864.

Similar methods were used to prepare a CD4-ECD conjugate having an F/P ratio of 0.96.

EXAMPLE 26

Preparation of Antibody-Aminodextran-Phycobiliprotein Conjugates

Additional conjugates were prepared essentially as described in 3 above for use in the experiments described in Examples 27–32, with the following exceptions.

For 1X-Amdex lots, the same molar ratio was used as in previous 5×-Amdex trials of 4:1:1=Dye:Ab:Amdex or weight ratio of 25.713:4.287:10=Dye:Ab:Amdex at 10 mg Amdex scale.

For Amdex-Molecular Probes, 50% less dye and Ab relative to Amdex was used so that molar ratio was 2:0.5:1=Dye:Ab:Amdex and weight ratio was 12.856:2.143:10=Dye:Ab:Amdex at 10 mg Amdex scale.

For 5X-Amdex, crosslinked, the same dye:Ab:Amdex molar ratios as previously listed and as used in 1X-Amdex trials were adopted.

EXAMPLE 27

Anti-CD8αβ Antibody-Aminodextran-PC5 Conjugates

Conjugation was carried out with 50% less dye and antibody relative to aminodextran (nominally 2,000,000 Da, 130 amines/mole or ~1/100 degree of substitution with single amine group per reacted glucose unit, Cat. No. D-7145, lot 6551-3 from Molecular Probes, Inc.) so that molar ratio was 2:0.5:1=PC5: CD8αβ antibody and weight ratio was 12.856:2.143:10 at 10 mg Amdex scale:

A. Activation of Aminodextran with Sulfo-SMCC.

0.340 mL of a 29.412 mg/mL solution of Amdex in distilled water, to which 0.018 mL of 20×PBS buffer solution were added to make a 1×PBS solution, were activated with 0.180 mL of 10 mg/mL sulfo-SMCC solution in 1×PBS, to which were added 0.462 mL 1×PBS solution to make a total Amdex concentration of 10 mg/mL. The mixture was roller mixed for about one hour at room temperature. After the mixing was completed, the reaction mixture was immediately applied to the top of a 60 mL G-50 Sephadex column equilibrated with 1×PBS. The sample was eluted using 1×PBS and collected in about 2 mL fractions. Fractions of the first band absorbing at 280 nm contained the high molecular weight activated Amdex as was verified by Tyndall scatter with a focused visible light beam(Model 650, Cambridge Instruments, Inc., Buffalo, N.Y.). These fractions were pooled to give about 5.8 mL total sulfo-SMCC-activated Amdex.

B. Activation of Antibody.

CD8αβ monoclonal antibody was activated by the addition of 0.033 mL of a 2 mg/mL solution of iminothiolane in 1×PBS and 0.219 mL 1×PBS to 0.081 mL of CD8αβ concentrate (61.67 mg/mL). The resulting solution which had an antibody concentration of 15 mg/mL and an iminothiolane molar concentration fifteen-fold larger was mixed at ambient temperature for about one hour. The reaction mixture was then chromatographed on a 60 mL G-50 Sephadex, column equilibrated with 1×PBS and the sample was eluted using 1×PBS. The first band peak fraction yielded about 4.2 mL of 1.113 mg/mL antibody solution which contained a total of 4.67 mg IT-CD8αβ antibody derivative.

C. Activation of PC5.

PC5 was activated by the addition of 0.097 mL of a 2 mg/mL solution of iminothiolane in 1×PBS and 0.098 mL 1×PBS to 0.179 mL of PC5 concentrate (83.625 mg/mL). The resulting solution which had a PC5 concentration of 40 mg/mL and an iminothiolane molar concentration 22.5-fold larger was mixed at room temperature for about one hour. The reaction mixture was then applied to the top of a 60 mL G-50 Sephadex column equilibrated with 1×PBS and the sample was eluted with 1×PBS. The first band peak fraction gave about 3.9 mL of 3.35 mg/mL PC5 at an $A_{565}/A_{280}$ ratio of 6.2394, which contained a total of 13.065 mg IT-PC5.

D. Conjugation of IT-CD8αβ and IT-PC5 to sulfo-SMCC-Amdex.

15 mg total protein: 10 mg Amdex.

1.926 mL of 1.113mg/mL IT-CD8αβ solution (about 2.143 mg antibody) were first mixed with 3.839 mL of 3.35 mg/mL IT-PC5 solution (about 12.856 mg IT-PC5), to which were added 5.8 mL of sulfo-SMCC-Amdex solution (about 10 mg Amdex)and the entire mixture was roller mixed overnight for 16–24 hours.

After the mixing was completed, the total volume of the mixture was determined and 0.120 times this volume of 5 mg/mL L-cysteine in 1×PBS was added to each conjugation mixture. The L-cysteine containing mixtures were then mixed for an additional 15 minutes to effect blocking of any unreacted sulfo-SMCC moieties. Lastly, 20 mg/mL iodoacetamide in 1×PBS in the amount of 0.120 times the total mixture volume and 1M borate buffer solution, pH 9.8, in the amount of 0.020 times the total mixture volume were added to each mixture. The resulting mixtures were mixed for about 30 minutes to block any unreacted sulfhydryl groups.

E. Purification of CD8αβ-Amdex-PC5 Conjugates.

The total volume of conjugation mixture was reduced to about 2.5 mL by centrifuging an Amicon Centri-Prep 30 tube containing the sample for about 20 minutes at 2000 rpm using a refrigerated Beckman J-6B centrifuge. The sample was placed on the top of a Bio-Gel A-15 m agarose column (2.5 cm×48 cm) equilibrated with 1×PBS and chromatographed using 1×PBS as eluant. Eluant fractions of about 3.6 mL volume were collected using a Pharmacia LKB FRAC-100 collector operating in the drop collection mode. The fractions were monitored using a LKB 2138 Uvicord S monitor operating at 280 nm. A chromatogram showing the $A_{280}$ versus fraction number recording is displayed in FIG. 22A and 22B. The first narrow, intense band eluted from the column contained the CD8αβ-aminodextran-PC5 conjugate. A lower intensity shoulder of less than one-third the intensity of the first peak contained ~1:1 PC5: aminodextran conjugate and excess PC5. A medium-to-low intensity well-separated third band was attributed to low molecular weight excess blocking reagents.

The fractions collected for the CD8αβ-Amdex-PC5 conjugate were analyzed spectrophotometrically at 565.5 and 280 nm using a 1 mm path length cell. The concentration of PC5 in mg/mL in the conjugate was derived from the absorbance at 565.5 nm by using the formula, $A_{565.5}/8.167$. Data for fractions 19 to 24 under the first narrow peak are listed in Table 29.

TABLE 29

CD8β-Amdex-PC5 conjugate

| fraction | PC5, mg/mL | volume/fraction | PC5, mg |
|---|---|---|---|
| 19 | .148 | 3.6 mL | 0.533 |
| 20 | .371 | | 1.336 |
| 21 | .301 | | 1.084 |
| 22 | .172 | | 0.619 |
| 23 | .107 | | 0.385 |
| 24 | .079 | | 0.284 |
| | | | 4.241 mg total in conjugate |

Since 12.73 mg I.T. -PC5 was used in conjugation, yield 4.241 mg ÷ 12.73 mg × 100 = 33.32%

EXAMPLE 28

Preparation of Anti-CD4 Antibody-Aminodextran-ECD Conjugates

These conjugates are prepared described in Example 27, except anti-CD4 antibody, also of the IgG1 class, was activated with IT and used in the conjugation instead of CD8αβ antibody, and the tandem PE-Texas red or ECD fluorescent dye was used instead of PC5. In trial 2, IT-ECD (12.856 mg), IT-CD4 (2.143 mg) were mixed with sulfo-SMCC-Amdex (10 mg) at concentrations of 1.10, 0.184, and 0.857 mg/mL, respectively, during conjugation. The IT-ECD ($A_{565.5}/A_{280}$) ratio was 5.424. The conjugation mixture was concentrated to about 1.5 mL and applied to the top of an A-15 m column. Data for fractions collected at about 3.6 mL per fraction under the first narrow peak in trial 2 are listed in Table 30.

TABLE 30

CD4-Amdex-ECD conjugate

| fraction | ECD, mg/mL | volume/fraction | ECD, mg |
|---|---|---|---|
| 20 | .194 | 3.6 mL | 0.698 |
| 21 | .505 | | 1.818 |
| 22 | .382 | | 1.375 |
| 23 | .203 | | 0.731 |
| 24 | .131 | | 0.472 |
| 25 | .099 | | 0.356 |
| 26 | .085 | | 0.306 |
| | | | 5.756 mg total in conjugate |

Since 12.858 mg I.T. -ECD was used in conjugation, yield = 5.756 mg ÷ 12.858 mg × 100 = 44.77%

EXAMPLE 29

Preparation of Anti-CD4 Antibody-Aminodextran-PE Conjugates

The methods were the same as those described in Example 27, except anti-CD4 antibody of the IgG class and PE were activated with IT and used in the conjugation instead of CD8αβ antibody and PC5. In trial 3, the reactants, 3.896 mL of 3.30 mg/mL IT-PE (12.856 mg) were first mixed with 4.75 mL of sulfo-SMCC-Amdex (10 mg) solution, to which were then added 3.058 mL of 0.701 mg/mL IT-CD4 (2.143 mg). The IT-PE($A_{565}/A_{280}$) ratio was 5.800. The conjugation mixture was concentrated to about 1.0 mL and applied to the top of an A-15 m column. Data for fractions collected at 3.6 mL per fraction under the first narrow peak in trial 3 are listed in Table 31.

TABLE 31

CD4-Amdex-PE conjugate

| fraction | PE, mg/mL | volume/fraction | PE, mg |
|---|---|---|---|
| 18 | .035 | 3.6 ml | 0.126 |
| 19 | .282 | | 1.015 |
| 20 | .417 | | 1.501 |
| 21 | .292 | | 1.051 |
| 22 | .163 | | 0.587 |
| 23 | .106 | | 0.382 |
| 24 | .082 | | 0.295 |
| | | | 4.957 mg total in conjugate |

Since 12.856 mg I.T. - PE was used in conjugation, yield = 4.957 mg ÷ 12.856 mg × 100 = 38.56%

EXAMPLE 30

Preparation of Antibody-5X-Amdex, X-linked-PE and -PC5 Conjugates

A low yield of T4-5X-Amdex, XL-PE conjugate as in 1X-Amdex trials was obtained. The CD8αβ-5X-PC5 conjugate with 1/5/98 lot of 5X-Amdex, XL gave an intense first band off the Bio-Gel A-15 m column but the yield was low since the bulk of the blue-purple conjugate aggregated with the gel at the top of the column and could not be eluted. Data for fractions collected at about 3.6 mL per fraction under the first narrow peak in this run are listed in Table 32.

TABLE 32

CD8αβ-5X-Aindex-PC5 conjugate

| fraction | PC5, mg/mL | volume/fraction | PC5, mg |
|---|---|---|---|
| 20 | .164 | 3.6 mL | 0.590 |
| 21 | .365 | | 1.314 |
| 22 | .303 | | 1.091 |
| 23 | .212 | | 0.763 |
| 24 | .161 | | 0.580 |
| 25 | .137 | | 0.493 |
| | | | 4.831 mg total in conjugate |

Since 25.724 mg I.T. - PC5 was used in conjugation, yield = 4.831 mg ÷ 25.724 mg × 100 = 18.78%

EXAMPLE 31

Preparation of Oligonucleotide-Amdex-Fluorescent Dye Conjugates

A. Direct Gene Amplification Reagent

Prepare water soluble carbodiimide of DNA(oligo) through 5' terminal phosphate by reaction with 1-ethyl-3-(3-dimethylaminopropyl)carbodiimide hydrochloride (EDAC); react in imidazole buffer to yield 5'-phosphorimidazolide; and then react with aminodextran to give phosphoramidate bonds, and purify conjugate on G-50 Sephadex. Next, activate remaining amino groups of aminodextran in conjugate with sulfo-SMCC; activate dye (PE, PC5, or ECD) with 2-iminothiolane; conjugate two activated components, and purify conjugate on A-15 m. For a description of the above synthetic methods, see, for example, *Bioconjugate Techniques*, G. T. Hermanson, Academic Press, San Diego, Calif., 1996, Chap. 17, pp. 639–671; and Pierce Catalog and Handbook, Life Science and Analytical Research Products, Pierce Chemical Company, Rockford, Ill., 1994/1995.

B. Indirect Gene Amplification Reagent

Prepare (a) amino 5'-oligo by first forming water soluble carbodiimide through 5' terminal phosphate, reacting with imidazole buffer to give 5'-phosphorimidazolide, and then reacting with ethylenediamine to form a phosphoramidate linkage; purify oligo derivative on G-25 Sephadex; (b) biotinylated DNA or oligo via 5'-terminal phosphate group by reacting a biotinylating agent, such as water-soluble N-hydroxysulfosuccinimide ester of biotin, in 1×PBS, pH 7.2–7.3, with amino 5'-oligo; purify product on G-25 Sephadex; (c) (streptavidin or avidin)-Amdex-PE (PC5 or ECD) conjugate by methods similar to preparation of antibody-Amdex-PE conjugates except antibody is substituted with the proteins streptavidin or avidin; and then combine (b) and (c), and use purified complex DNA(oligo)-avidin-Amdex-PE to analyze sample of DNA or RNA.

EXAMPLE 32

Preparation of MHC/peptide-Avidin-Amdex-Fluorescent Dye Conjugates

The strategy is similar to preparation of an indirect gene amplification reagent described in Example 31B. Prepare (a) biotinylated MHC/peptide complex as described in Tracking of Antigen-specific Helper T Cell Response, M. G. McHeyszer-Williams, J. D. Altman, and M. M. Davis, *Current Opinion in Immunol.* 278–284 (1996); (b) (streptavidin or avidin)-Amdex-PE (PC5 or ECD) conjugate by methods similar to antibody-Amdex-PE conjugates except antibody is substituted with the protein, streptavidin or avidin; and then combine (a) and (b) and use purified conjugate, MHC/peptide-(streptavidin or avidin)-Amdex-PE, to analyze binding to TCR.

EXAMPLE 33

Flow Cytometry Results for Cells Stained with Conjugates

The mixtures of fluorescent antibody conjugates, either direct or crosslinked with aminodextran, with 100 μL whole blood were incubated for 10 min at room temperature, then lysed and quenched on the Coulter Q-PREP, washed once with 1×PBS (by addition of 2 mL of 1×PBS, centrifugation at 500 g for 5 min, discarding supernatant, and resuspension of cells in 1 mL of 1×PBS) and analyzed on a flow cytometer (Coulter Epics XL-MCL). Titers of conjugates were usually 0.5 μg antibody, as determined by the $A_{280}$ value of the sample.

A. CD4-1X-Amdex-PE lots

TABLE 33

| | | Mnl-X | | | S/N Ampl. | Neg. Ampl. | Pos. Amplif. |
|---|---|---|---|---|---|---|---|
| | fraction | Neg Mnl | Pos Mnl | S/N | Ratio | Ratio | Ratio |
| 2213-18 1X | 21 | 0.15 | 59 | 396 | 1.0 | 0.8 | 0.8 |
| | 22 | 0.14 | 90 | 639 | 1.7 | 0.8 | 1.3 |
| | 23 | 0.15 | 101 | 670 | 1.8 | 0.8 | 1.4 |
| | 24 | 0.15 | 123 | 802 | 2.1 | 0.8 | 1.7 |
| | 25 | 0.17 | 106 | 630 | 1.6 | 0.9 | 1.5 |
| | 26 | 0.19 | 289 | 1512 | 3.9 | 1.0 | 4.1 |
| | 27 | 0.21 | 275 | 1286 | 3.4 | 1.2 | 3.9 |
| | 28 | 0.20 | 264 | 1304 | 3.4 | 1.1 | 3.7 |
| | 29 | 0.24 | 258 | 1098 | 2.9 | 1.3 | 3.6 |
| | 30 | 0.23 | 248 | 1073 | 2.8 | 1.2 | 3.5 |
| 2145-26 1X | 21 | 0.20 | 232 | 1143 | 3.0 | 1.1 | 3.3 |
| | 22 | 0.22 | 265 | 1231 | 3.2 | 1.2 | 3.7 |
| | 23 | 0.22 | 272 | 1238 | 3.2 | 1.2 | 3.8 |
| | 24 | 0.23 | 283 | 1216 | 3.2 | 1.3 | 4.0 |
| | 25 | 0.21 | 261 | 1221 | 3.2 | 1.2 | 3.7 |
| | 26 | 0.27 | 250 | 932 | 2.4 | 1.4 | 3.5 |
| | 27 | 0.29 | 238 | 818 | 2.1 | 1.6 | 3.3 |
| | 28 | 0.33 | 223 | 676 | 1.8 | 1.8 | 3.1 |
| | 29 | 0.29 | 211 | 736 | 1.9 | 1.5 | 3.0 |
| | 30 | 0.28 | 195 | 691 | 1.8 | 1.5 | 2.7 |
| 2249-50 1X | 20 | 0.20 | 143 | 732 | 1.9 | 1.0 | 2.0 |
| | 21 | 0.22 | 196 | 897 | 2.3 | 1.2 | 2.8 |
| | 22 | 0.21 | 204 | 969 | 2.5 | 1.1 | 2.9 |
| | 23 | 0.24 | 198 | 840 | 2.2 | 1.3 | 2.8 |
| | 24 | 0.25 | 190 | 777 | 2.0 | 1.3 | 2.7 |
| | 25 | 0.26 | 181 | 704 | 1.8 | 1.4 | 2.5 |
| | 26 | 0.27 | 175 | 646 | 1.7 | 1.5 | 2.5 |
| 2326-75 1X | 22 | 0.18 | 138 | 773 | 2.0 | 1.0 | 1.9 |
| | 23 | 0.21 | 229 | 1113 | 2.9 | 1.1 | 3.2 |
| | 24 | 0.19 | 252 | 1318 | 3.4 | 1.0 | 3.5 |
| | 25 | 0.19 | 238 | 1248 | 3.3 | 1.0 | 3.3 |

TABLE 33-continued

| | | Mnl-X | | | S/N Ampl. | Neg. Ampl. | Pos. Amplif. |
|---|---|---|---|---|---|---|---|
| | fraction | Neg Mnl | Pos Mnl | S/N | Ratio | Ratio | Ratio |
| | 26 | 0.20 | 211 | 1055 | 2.8 | 1.1 | 3.0 |
| | 27 | 0.19 | 190 | 978 | 2.6 | 1.0 | 2.7 |
| | 28 | 0.23 | 203 | 865 | 2.3 | 1.3 | 2.8 |
| | 29 | 0.22 | 176 | 797 | 2.1 | 1.2 | 2.5 |
| | 30 | 0.25 | 169 | 688 | 1.8 | 1.3 | 2.4 |
| CD4-5X-PE | | 0.21 | 177 | 837 | 2.2 | 1.1 | 2.5 |
| CD4-PE | | 0.19 | 71 | 383 | 1.0 | 1.0 | 1.0 |

Positive amplification ratios listed for the 4 lots of 1X-Amdex conjugates with CD4, PE show maxima of 4.1, 4.0, 2.9, and 3.5 in a middle fraction of a low yield first band or shoulder that appeared in Bio-Gel A-15 m chromatography of conjugation mixtures. The highest amplifications were obtained with lot 2213-18 and 2145-26 conjugates in fractions on the shoulder of the second band rather than the weak first band. However, a 1:1 correspondence between the greatest amplification and the first band was observed with lot 2249-50 and 2326-75 conjugates.

B. CD8αβ-1X-Amdex-PC5 lots

Lot 2213-18 and 2145-26 1X-Amdex conjugates with CD8αβ, PC5 gave first band fractions with about the same or only slightly better mean channel fluorescence intensity than the direct CD8αβ-PC5 control. Conjugates with lot 2249-50 and 2326-75 1X-Amdex did show amplification which peaked at 2.2 and 3.5, respectively, and corresponded with fractions in the peak of the first chromatographic band.

TABLE 34

| | | Mnl-X | | | S/N Ampl. | Neg. Ampl. | Pos. Amplif. | % | |
|---|---|---|---|---|---|---|---|---|---|
| | Fraction | Neg Mnl | Pos Mnl | S/N | Ratio | Ratio | Ratio | Neg | Pos |
| 2213-18 1X | 21 | 0.19 | 33 | 176 | 0.6 | 1.0 | 0.6 | 71 | 29 |
| | 22 | 0.25 | 75 | 307 | 1.1 | 1.3 | 1.4 | 70 | 30 |
| | 23 | 0.29 | 88 | 305 | 1.1 | 1.5 | 1.6 | 70 | 29 |
| | 24 | 0.28 | 86 | 307 | 1.1 | 1.5 | 1.6 | 70 | 30 |
| | 25 | 0.28 | 80 | 283 | 1.0 | 1.5 | 1.4 | 70 | 30 |
| | 26 | 0.29 | 86 | 296 | 1.0 | 1.5 | 1.6 | 71 | 29 |
| | 27 | 0.28 | 82 | 288 | 1.0 | 1.5 | 1.5 | 69 | 31 |
| | 28 | 0.30 | 86 | 290 | 1.0 | 1.5 | 1.5 | 71 | 29 |
| | 29 | 0.29 | 84 | 289 | 1.0 | 1.5 | 1.5 | 71 | 29 |
| | 30 | 0.30 | 81 | 272 | 0.9 | 1.6 | 1.5 | 71 | 29 |
| 2145-26 1X | 20 | 0.16 | 22 | 135 | 0.5 | 0.8 | 0.4 | 72 | 28 |
| | 21 | 0.19 | 39 | 200 | 0.7 | 1.0 | 0.7 | 71 | 29 |
| | 22 | 0.22 | 52 | 235 | 0.8 | 1.1 | 0.9 | 71 | 29 |
| | 23 | 0.21 | 57 | 270 | 0.9 | 1.1 | 1.0 | 71 | 29 |
| | 24 | 0.22 | 57 | 262 | 0.9 | 1.1 | 1.0 | 71 | 29 |
| | 25 | 0.25 | 45 | 181 | 0.6 | 1.3 | 0.8 | 72 | 28 |
| | 26 | 0.23 | 64 | 277 | 1.0 | 1.2 | 1.2 | 70 | 30 |
| | 27 | 0.24 | 66 | 271 | 0.9 | 1.3 | 1.2 | 71 | 29 |
| | 28 | 0.25 | 43 | 173 | 0.6 | 1.3 | 0.8 | 71 | 29 |
| | 29 | 0.26 | 68 | 258 | 0.9 | 1.4 | 1.2 | 70 | 30 |
| 2249-50 1X | 22 | 0.31 | 92 | 297 | 1.0 | 1.6 | 1.7 | 70 | 30 |
| | 23 | 0.33 | 118 | 359 | 1.2 | 1.7 | 2.1 | 69 | 31 |
| | 24 | 0.33 | 123 | 368 | 1.3 | 1.7 | 2.2 | 70 | 30 |
| | 25 | 0.34 | 124 | 364 | 1.3 | 1.8 | 2.2 | 69 | 31 |
| | 26 | 0.36 | 113 | 310 | 1.1 | 1.9 | 2.0 | 71 | 29 |
| | 27 | 0.36 | 102 | 282 | 1.0 | 1.9 | 1.8 | 71 | 29 |
| 2326-75 1X | 21 | 0.27 | 175 | 652 | 2.2 | 1.4 | 3.2 | 70 | 30 |
| | 22 | 0.36 | 193 | 539 | 1.9 | 1.9 | 3.5 | 70 | 30 |
| | 23 | 0.41 | 193 | 472 | 1.6 | 2.1 | 3.5 | 71 | 29 |
| | 24 | 0.36 | 170 | 470 | 1.6 | 1.9 | 3.1 | 71 | 29 |
| | 25 | 0.33 | 153 | 462 | 1.6 | 1.7 | 2.8 | 71 | 30 |
| | 26 | 0.35 | 138 | 398 | 1.4 | 1.8 | 2.5 | 70 | 30 |
| | 27 | 0.32 | 134 | 423 | 1.5 | 1.7 | 2.4 | 71 | 29 |
| CD8αβ-5X-PC5 | | 0.44 | 664 | | | | | 73 | 27 |
| CD8αβ-PC5 | | 0.19 | 55 | 290 | 1.0 | 1.0 | 1.0 | 73 | 28 |

C. Molecular Probes Amdex, CD4-Amdex-PE conjugate

TABLE 35

| | | Mnl-X | | | S/N Ampl. | Neg. Ampl. | Pos. Amplif | % | |
|---|---|---|---|---|---|---|---|---|---|
| | | Neg Mnl | Pos Mnl | S/N | Ratio | Ratio | Ratio | Neg | Pos |
| 0.3X-mp-2m | fxn 18 | 0.47 | 501 | 1072 | 3.6 | 1.9 | 6.9 | 46 | 54 |
| | fxn 19 | 0.51 | 624 | 1226 | 4.1 | 2.1 | 8.5 | 45 | 55 |
| | fxn 21 | 0.44 | 508 | 1168 | 3.9 | 1.8 | 7.0 | 45 | 55 |
| | fxn 22 | 0.37 | 426 | 1157 | 3.9 | 1.5 | 5.8 | 55 | 45 |
| | fxn 23 | 0.42 | 351 | 837 | 2.8 | 1.7 | 4.8 | 45 | 55 |
| | fxn 24 | 0.43 | 319 | 738 | 2.5 | 1.8 | 4.4 | 51 | 49 |
| 2145-26 1X | 0.5 ug | 0.24 | 202 | 843 | 2.8 | 1.0 | 2.8 | 55 | 45 |
| CD4-5xPE. | 1 ug | 0.54 | 311 | 576 | 1.9 | 2.2 | 4.3 | 47 | 53 |
| | 0.1 ug | 0.17 | 5 | 32 | 0.1 | 0.7 | 0.1 | 46 | 54 |
| CD4-PE | 1 ug BP | 0.24 | 73 | 300 | 1.0 | 1.0 | 1.0 | 46 | 54 |

D. CD4-Amdex-ECD conjugate

TABLE 36

| | | Mnl-X | | | S/N Ampl. | Neg. Ampl. | Pos. Amplif. | % | |
|---|---|---|---|---|---|---|---|---|---|
| | | Neg Mnl | Pos Mnl | S/N | Ratio | Ratio | Ratio | Neg | Pos |
| 0.3X-mp-2m | fxn 19 | 0.21 | 129 | 624 | 2 | 1.0 | 2.2 | 63 | 37 |
| | fxn 20 | 0.23 | 240 | 1032 | 4 | 1.1 | 4.1 | 63 | 37 |
| | fxn 21 | 0.24 | 243 | 1016 | 4 | 1.1 | 4.2 | 62 | 38 |
| | fxn 22 | 0.24 | 228 | 936 | 3 | 1.1 | 3.9 | 63 | 37 |
| | fxn 23 | 0.24 | 200 | 823 | 3 | 1.1 | 3.4 | 63 | 37 |
| | fxn 24 | 0.26 | 191 | 733 | 3 | 1.2 | 3.3 | 64 | 36 |
| | fxn 25 | 0.26 | 189 | 722 | 3 | 1.2 | 3.2 | 62 | 38 |
| | fxn 26 | 0.22 | 150 | 690 | 3 | 1.0 | 2.6 | 63 | 37 |
| | fxn 27 | 0.22 | 146 | 674 | 2 | 1.0 | 2.5 | 63 | 37 |
| | fxn 28 | 0.21 | 133 | 624 | 2 | 1.0 | 2.3 | 63 | 37 |
| CD4-ECD | 0.5 ug BP | 0.22 | 58 | 272 | 1 | 1.0 | 1.0 | 62 | 38 |

E. CD8αβ-Amdex-PC5 conjugate

TABLE 37

| | | Mnl-X | | | S/N Ampl. | Neg. Ampl. | Pos. Amplif | % | |
|---|---|---|---|---|---|---|---|---|---|
| | CD8αβ-PC5 | Neg Mnl | Pos Mnl | S/N | Ratio | Ratio | Ratio | Neg | Pos |
| 0.3X-mp-2m | fxn 18 | 0.18 | 52 | 280 | 0.9 | 1.2 | 1.1 | 82 | 18 |
| | fxn 19 | 0.20 | 102 | 519 | 1.7 | 1.3 | 2.2 | 82 | 18 |
| | fxn 20 | 0.19 | 97 | 498 | 1.6 | 1.3 | 2.1 | 81 | 19 |
| | fxn 21 | 0.20 | 95 | 480 | 1.6 | 1.3 | 2.0 | 82 | 18 |
| | fxn 22 | 0.21 | 92 | 436 | 1.4 | 1.4 | 2.0 | 82 | 18 |
| | fxn 23 | 0.26 | 82 | 313 | 1.0 | 1.7 | 1.8 | 82 | 19 |
| 1X 2326-75 CD8αβ-5X-PC5 | 1x fxn 21 | 0.23 | 131 | 572 | 1.9 | 1.5 | 2.8 | 81 | 19 |
| | 5x fxn 43 | off scale | | | | | | | |
| CD8αβ-PC5 | 0.5 ug BP | 0.15 | 47 | 307 | 1.0 | 1.0 | 1.0 | 83 | 17 |

Maximum amplification of 8.5, 4.2, and 2.2 occurred in the CD4,PE; CD4,ECD; and CD8αβ,PC5 conjugates with Amdex from Molecular Probes, Inc. at fractions 19-20, 20-21, and 19-20, respectively. These fractions coincided with the lower fraction side or higher molecular weight side of the first intense band observed in chromatography of conjugation mixtures. The CD4-Amdex-PE conjugate gave the highest amplification ever obtained for a CD4, PE conjugate with any lot of aminodextran. Also, this ECD conjugate is the first one to show excellent yield in the first band as well as the highest amplification of any ECD conjugate.

F. CD4-5X-Amdex-PE conjugate

TABLE 38

| | Mnl-X | | S/N | S/N Ampl. Ratio | Neg. Ampl. Ratio | Pos. Amplif. Ratio | % | |
|---|---|---|---|---|---|---|---|---|
| | Neg Mnl | Pos Mnl | S/N | | | | Neg | Pos |
| fxn 21 | 0.42 | 271 | 651 | 1.7 | 2.2 | 3.7 | 66 | 34 |
| fxn 22 | 0.39 | 301 | 769 | 2.0 | 2.0 | 4.1 | 68 | 32 |
| fxn 23 | 0.42 | 334 | 794 | 2.1 | 2.2 | 4.6 | 64 | 35 |
| fxn 24 | 0.47 | 332 | 715 | 1.9 | 2.4 | 4.6 | 65 | 35 |
| fxn 25 | 0.60 | 343 | 569 | 1.5 | 3.1 | 4.7 | 63 | 37 |
| fxn 26 | 0.33 | 290 | 870 | 2.3 | 1.7 | 4.0 | 64 | 36 |
| CD4-5X-PE | 0.35 | 211 | 596 | 1.6 | 1.8 | 2.9 | 65 | 35 |
| 1X-2326-75 | 0.20 | 281 | 1391 | 3.7 | 1.0 | 3.9 | 71 | 29 |
| 1X-2249-50 | 0.23 | 201 | 870 | 2.3 | 1.2 | 2.8 | 65 | 35 |
| CD4-PE | 0.19 | 73 | 376 | 1.0 | 1.0 | 1.0 | 64 | 36 |

The conjugate with the 1/5/98 lot of 5X-Amdex showed a maximum amplification of 4.4–4.0 at fractions 25-24, which corresponded with the first band, a shoulder on the second broad, intense band of excess PE, centered near fraction 45.

Figure 22A:
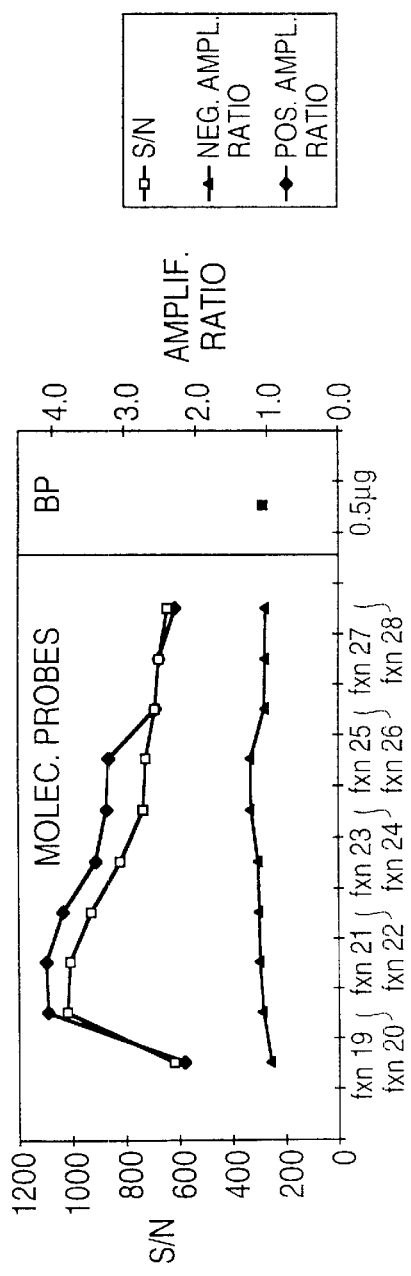
FIG. 22A is a line graph illustrating the positive amplification ratio, signal-to-noise ratio, and the negative amplification for fractions of CD4-Amdex(M.P.)-ECD collected from the A-15m column.
Figure 22B:
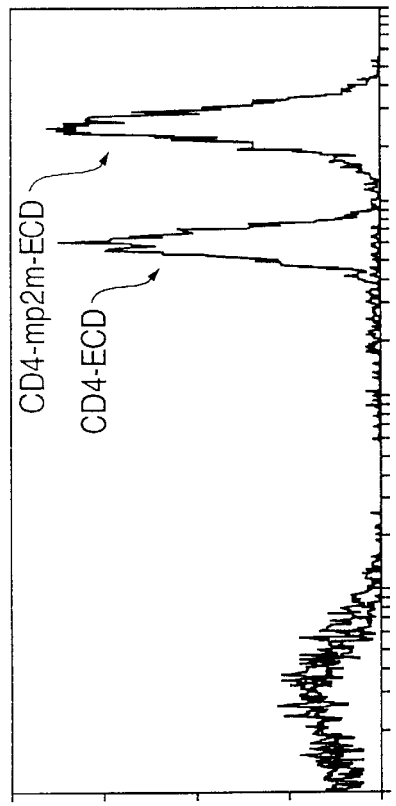
FIG. 22B is a flow cytometry histogram for CD4-ECD versus CD4-Amdex (M.P.)-ECD.
Figure 23:
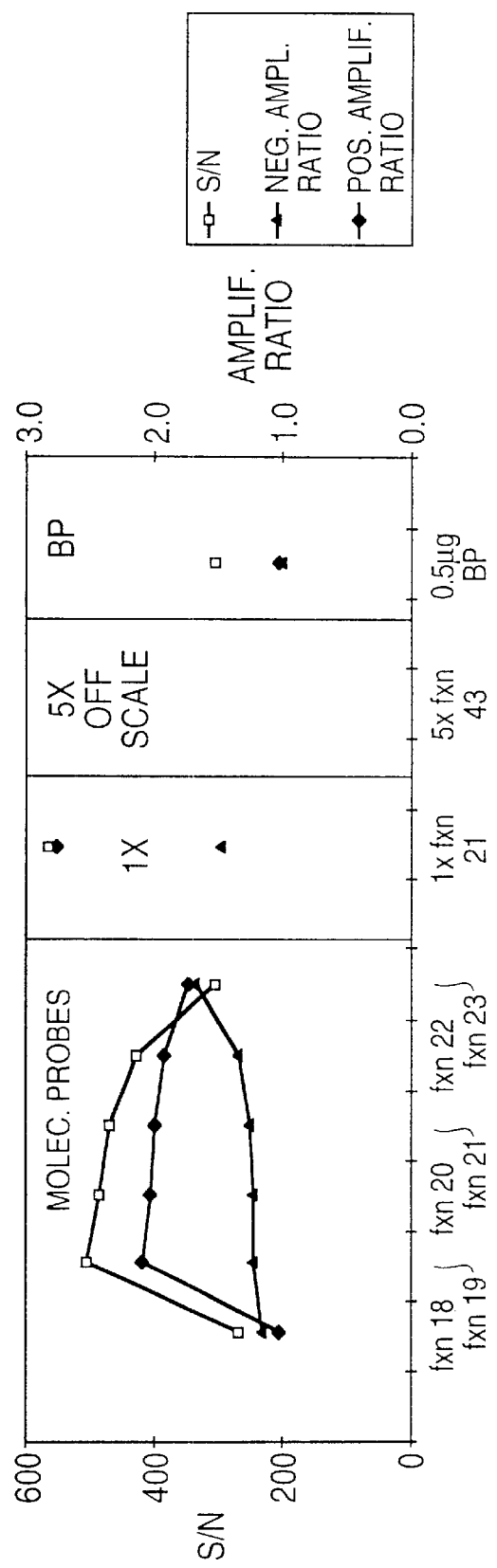
FIG. 23 illustrates the parallel dependence of the three ratios described in FIG. 22A for fractions of the CD8αβ-Amdex (M.P.)-PC5 conjugate.

A degree of substitution of ~1/100 with single amino group per reacted glucose unit was shown to be sufficient to obtain Ab-Amdex-PE(PC5, ECD) conjugates in good yields. For CD4-Amdex-PE conjugates the Molecular Probes aminodextran has provided the highest amplification of fluorescence intensity over that obtained with direct CD4-PE conjugate in labelling CD4+ cells in whole blood. Flow cytometry histograms of the number of fluorescence events versus mean channel fluorescence intensity are shown in FIGS. 21A–21D for various CD4-PE versus CD4-Amdex-PE labelled lymphocytes of the same blood donor. Good separation between the direct conjugate and each Amdex-crosslinked conjugate was obtained. Also, no interference from CD4 negative populations was ever observed. Similar histograms for CD4-ECD versus CD4-Amdex-ECD are shown in FIGS. 22A–22B, together with a graphical depiction of the positive amplification ratio, signal-to-noise ratio, and negative amplification ratio for fractions of CD4-Amdex-ECD collected from the A-15 m column. Parallel graphical dependence of the same three ratios for fractions of the CD8αβ-Amdex-PC5 conjugate are displayed in FIG. 23.

EXAMPLE 34

Triple Dector System Results

The samples were run on the Viscotek triple detection system at a concentration of 0.7 to 1.0 mg/mL in 0.2 M aqueous sodium nitrate solution through a column consisting of a 50' coil of 0.01" i.d. stainless steel tubing without any column packing in batch mode. The responses of the three primary detectors are as follows: light scattering. $M \times (dn/dc)^2 \times c$; viscometer, $IV \times c$; refractometer, $dn/dc \times c$. Each detector contributes a different yet complementary variable. Right angle light scattering gives the molecular weight when combined with viscometry detection. The 90° LS is corrected for angular dissymmetry using the Debye equation, together with the molecular size information provided by the viscometer. Viscometry yields the molecular density, which is related to conformation and branching, and the refractometer measures concentration of sample, providing direct determination of the refractive index increment, dn/dc, of the polymer sample. The hydrodynamic volume of a polymer molecule in solution, related to the cube of its radius of gyration, $R_g$, is directly proportional to the intrinsic viscosity (IV or η) and the weight average molecular weight ($M_w$), divided by Avocadro's number. Molecular data for dextran and aminodextran samples determined from duplicate batch analyses by the triple detector system are summarized in Table 39.

TABLE 39

| Sample | Conc. mg/mL | dn/dc mL/g | $M_w$, Da | IV, dL/g | $R_g$, nm |
|---|---|---|---|---|---|
| 5X-Amdex, 2326-11 | 0.860 | 0.155 | 414,000 (395,000/432,000) | 0.262 (0.269/0.254) | 5.6 (15.5/15.6) |
| 1X-Amdex 2326-75 | 0.940 | 0.155 | 1,044,000 (1,141,000/947,000) | 0.449 (0.449/0.434) | 25.2 (26.2/24.3) |
| Dextran T-2M | 0.800 | 0.147 | 2,102,000 (2,215,000/1,989,000) | 0.609 (0.631/0.586) | 35.5 (36.5/34.5) |
| 5X-Amdex, 1/5/98 | 0.800 | 0.190 | 70,000 (70,200/69,700) | 0.167 (0.164/0.170) | 7.38 (7.33/7.42) |
| Amdex, Mol. Pr. | 0.770 | 0.155 | 2,999,000 (3,002,000/2,995,000) | 0.674 (0.682/0.666) | 41.3 (41.5/41.1) |

The accuracy of $R_g$ values determined by the triple detector system is claimed to be within 0.5 nm.

Regression analysis for all data except for the 5X-Amdex, 1/5/98 sample of crosslinked aminodextran gave a corelation coefficient of 0.993, a Y-intercept of −3.337, and a slope of 0.493. The slope corresponds to the exponent in the Mark-Houwink-Sakurada equation, $[\eta]=KM^a$ and in four of the above samples the value is very similar to the a=0.50 one obtained for the linear fraction of dextran of 20,000 to 100,000 Da in water at 25° C. as compiled in M. Kurata and Y. Tsunashima, "Viscosity-Molecular Weight Relationships and Unperturbed Dimensions of Linear Chain Molecules", Chapter VII, pp. 1–555, in Polymer Handbook, J. Brandrup and E. H. Inimergut, eds., Wiley-lnterscience, New York, N.Y. (1989). This value of the exponent, a–0.50, has been established for linear, flexible polymers under 'theta' temperature or solvent conditions, whereas the branched fraction of dextran of 800,000 Da in water at 25° C. gave a=0.20. We therefore conclude that the only aminodextran sample which does not behave as a flexible, linear chain arranged in a compact, globular structure in aqueous sodium nitrate solution is the crosslinked 5X-Amdex, 1/5/98 sample. The value of K in the equation for the four dextran samples was $46 \times 10^{-3}$ mL/g, compared to a value of $97.8 \times 10^{-3}$ mL/g listed for linear dextran in the previous reference:

Previous studies of dextran of molecular weight greater than about 2,000 Da have all indicated a globular structure: 1) dextran prepared by freeze fixation and detected by electron microscopy in "Electron-Microscopic Study of Dextran and Poly(vinyl alcohol) Solutions, Chem. Abstr. 82:64427v (1975) showed dextran globules; 2) dextran in aqueous solution assumed a compact "shaggy" helical coil in H. Van Oene and L. H. Cragg, "Shear Dependence in Solutions of Fractionated Dextran: A Variable-Shear Capillary Viscometer for use with Aqueous Solutions", *J. Polym. Sci.*, 57:175–185 (1962); 3) direct observation of the polymerization reaction to form dextran in the cell of a light scattering instrument followed by construction of Zimm plots for dextran solutions showed uniform sphere of 75–85 nm radii of gyration for molecular weights of $64$–$105 \times 10^6$ Da in F. A. Bovey, "Enzymatic Polymerization. I. Molecular Weight and Branching During the Formation of Dextran", *J. Polym. Sci.*, 35:167–182 (1959).

The radius of gyration for a randomly coiled, linear, polymer molecule hs been derived from random walk statistics as $R_g^2 = \frac{1}{6} n l^2$, where n is the number of statistical segments in the polymer chain and 1 is the length of each statistical segment. Also, the mean square end-to-end distance in a random coil is given by $R^2 = nl^2$, as shown in "Principles of Colloid and Surface Chemistry", $2^{nd}$ ed., P. C. Hiemenz, Marcel Dekker, Inc., New York, N.Y. pp. 102–107.(1986). Thus, it becomes possible to use the accurate $R_g$ and mass average molecular weight values obtained from light scatter and viscosity, and elemental analyses (empirical formulae and degree of substitution) to calculate the root mean square end-to-end distance, R, the average molecular mass per segment, $M_i$, the number of statistical segments, and a statistical segment length in each polymer. These latter values can then be compared to the length of a single unit of 1,6-linked glucose reported as about 8 Å long by F. A. Bovey, cited above. The calculated data are presented in Table 40.

TABLE 40

| Sample | $M_i$, Da | n | R, nm | I, A |
|---|---|---|---|---|
| 5X-Amdex, 2326-11 | 183.7 | 2,254 | 38.2 | 8.0 |
| 1X-Amdex, 2326-75 | 164.0 | 6,366 | 61.7 | 7.7 |
| Dextran, T-2M | 162.1 | 12,967 | 87.0 | 7.6 |
| 5X-Amdex, 1/5/98 | 154.8 | 452 | 18.1 | 8.5 |
| Amdex, Mol. Pr. | 162.9 | 18,410 | 101.2 | 7.5 |

The $M_i$ value for the crosslinked 5X-Amdex, 1/5/98 could not be calculated in the same way as the other aminodextran samples, i.e., by obtaining the empirical formula with four nitrogen atoms and averaging its molecular mass over the number of units derived from the degree of substitution of each reacted glucose residue with two diaminopropane units. Rather, the mass of the empirical formula with eight nitrogen atoms (four bridging, four non-bridging) per chain was averaged over fifteen units, three times the number of units derived from the degree of substitution (⅕). As a result, its statistical segment length of 8.5 A is similar to the other values ranging from 7.5 to 8.0 A for linear chain polymer molecules, which values are all very close to the reported value of 8A. The methylene group between residues of 1,6-glucosyl units in dextran appears to confer an added flexibility on the dextran chain in contrast to the rigidity of the chain of 1,4-glucosyl units in cellulose nitrate in which glucose residues are joined only by an ether linkage. Light scattering results and a Zimm plot for cellulose nitrate in acetone reported in P. Doty et al., *J. Amer. Chem. Soc.*, 75:754 (1953) and A. M. Holtzer et al., 58:624 (1954), give $M_w$=400,000 Da and a statistical segment length of 35 Å or about seven 1,4-glucosyl units. In this cellulose nitrate, each monomer unit has a molecular mass of 297 DA and a length of 5.15 Å The number of units in a single chain of 400,000 Da would be 1350. Therefore, this chain would be 6950 Å long if it were completely extended. The root mean square end-to-end distance from light scattering was 1500 Å. The longer statistical segment length and high R value confirm that cellulose nitrate has an unusually stiff and extended structure. Randomly coiled polymers such as dextran and aminodextrans have much more tightly coiled and compact structures.

EXAMPLE 35

Estimation of Molecular Weights of Antibody-Aminodextran-Phycobiliprotein Conjugates and Phycobiliprotein-to-Aminodextran Molar Ratios Blue dextran (Sigma, T-2M) was applied to an A-15 m column that was used to purify the antibody-aminodextran-PE conjugates, eluted from the column with 1×PSB, monitored by $A_{280}$, and collected at the same drop count of 120 drops/fraction. The first narrow peak (about fraction 20 for 1X-Amdex, Amdex (M.P.), and 5X-Amdex, 2326-11) in the elution profile of antibody-aminodextran-dye conjugates occurred in the same fraction as the first narrow peak in the elution profile of blue dextran. Therefore, the conjugates are estimated to have a molecular weight of at least 2M Da. More accurate molecular weights were obtained from dynamic light scattering (also referred to as QELS, quasi-elastic light scattering or PCS, photon correlation spectroscopy) measurements on the Coulter sub-micron particle analyzer, Model N4MD, for solutions of PE, PC5 and ECD as well as their CD4 (and CD8αβ) antibody-aminodextran-dye conjugates at concentrations of 5 mg/mL or less in 1×PBS buffer, pH 7.2 with 632.8 nm He/Ne laser excitation. Results of these measurements are given in Table 40 for PE and its CD4 antibody conjugates with aminodextrans. Fluorescence emission events on the order of nanoseconds did not appear to affect translational Brownian motion measured at sample times of 3 to 10 microseconds. Analyses for all three PE, PC5, and ECD conjugates with CD4-Amdex (M.P.) gave the same meaning diameter of 146 nm, even though emission band maxima are located at widely different wavelengths of 583, 660, 615 mm respectively. Molecular weights (M) of the corresponding conjugates listed in Table 40 were calculated by assuming the same relationship, $4\pi(R/2)^2=1.1$ M, established between surface area of a sphere of radius R/2 and molecular weight of dextran and aminodextrans from the triple detector (Light scatter, viscosity, and refractive index) results and, also cited as a direct proportionality between surface area and molecular weight in (T. E. Creighton, Proteins: Structures and Molecular Principles [W. H. Preeman, New York, 1983) p. 242] for large protein molecules.

Table 41 provides the mean diameters of PE and its conjugates and molar ratios of PE-Aminodextran. Molar ratios, PE/Amdex, were obtained in three different ways:

(1) By calculating the number of hard spheres of PE (mean diameter, 34.3 nm) that can be arranged in a closest packed array around a hard sphere of aminodextran (diameter given by R values from Table V); i.e. surface area of sphere of aminodextran, 4 $(R/2)^2$ divided by $d^2$ (PE)×3/2, and then multiplying by the mole fraction of PE;

(2) By subtracting the molecular weight of one aminodextran molecule from the molecular weight of the conjugate, then, dividing by the average of the molecular weights of 1gG antibody (160,000 Da) and PE(270,000 Da), and finally multiplying by the mole fraction of PE;

(3) By the taking the ratio of mean channel fluorescence intensity of the direct CD4-aminodextran-PE conjugate to the mean channel fluorescence intensity of the direct CD4-PE conjugate, both measured by flow cytometry at saturation of the receptor sites on the targeted CD4+ lymphocytes in whole blood. The mote fraction of PE in the sample of conjugate was calculated from spectrophotometric data for the concentrations of PE from $A_{565}$ and CD4 antibody from $A_{280}$ corrected for PE absorbance at 280 nm, and the respective molecular weights. The second molecular s weight value (a) provided for PE was as described in R. McColland and D. Guard-Friar, Phycobiliproteins, CRC Press Inc., Boca Raton, Fla. (1983).

amplification factors exceed packing limits around a single 5X-Amdex molecule for cross-linked 5X-Amdex and, thus, suggest that more than one 5X-Amdex molecule is part of the conjugate. This allows a network of - - - 5X-Amdex - - - Ab, PE - - - 5X-Amdex - - - to form and contain additional PE molecules.

All publications cited in this specification are indicative of the level of skill of those in the art to which this application pertains. Each publication is individually incorporated herein by reference in the location where it is cited. The text of parent application Ser. No. 08/976,031, filed Nov. 21, 1997 and grandparent application Ser. No. 08/857,941, filed May 16, 1997, are also incorporated by reference herein.

While the invention has been described with reference to a particularly preferred embodiment, it will be appreciated that numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for a single-measurement quantification of multiple populations of cells having substantially similar binding partner densities in a flow cytometric analysis comprising the steps of
   labeling a first cell population with a first ligand capable of binding to a first binding partner on the surface of said first cell population, said first ligand being directly conjugated to a first phycobihiprotein or a phycobiliprotein-containing tandem dye;
   labeling a second cell population with a second ligand capable of binding to a second binding partner on the

TABLE 41

| Species | Mean Diameter, nm | Molecular Weight, Da | Mole fraction, PE/ (PE + Ab) | PE/Amdex by packing | PE/Amdex by MW | PE/Amdex by flow cytometry |
|---|---|---|---|---|---|---|
| PE | 34.3 | 336,000 270,000 [a] | | | | |
| CD4-1X-Amdex-PE | 90.2 | 2,324,000 | 0.553 | 6.5 | 3.3 | 2.4 |
| CD4-Amdex(M.P.) | 146 | 6,088,000 | 0.488 | 15.4 | 7.0 | 8.2 |
| CD4-5X-Amdex(-2326-11) | 116 | 3,843,000 | 0.401 | 4.8 | 6.4 | 4.2 |
| CD4-5X-Amdex(1/5/98) | 57.4 | 940,000 | 0.560 | 3.4 | 2.3 | 4.4 |

Estimates of the PE/Amdex ratios by packing and by molecular weight differ most widely from each other for 1X-Amdex and Amdex (M.P.) conjugates. Values from molecular weight calculations are much lower, suggesting that tightly packed dye and antibody structures around these aminodextrans of relatively high molecular weight and low amino substitution are not present. Rather, the limiting factor in having large PE/Amdex ratios and, thus, high fluorescence amplifications is not the size of the aminodextran but the degree of substitution with functional amine groups through which protein can be conjugated.

The agreement between PE/Amdex ratios calculated from packing or molecular weight data is much closer for 5X-Amdex conjugates, especially for the lot-2326-11 aminodextran conjugates. Here, packing considerations dominate the ability to obtain large dye-to-Amdex ratios. Further, surface of said second cell population, which second ligand is crosslinked to an aminodextran which is conjugated to a second phycobiliprotein or phycobilprotein-containing tandem dye;
activating said first and second phycobiliproteins or phycobiliprotein-containing tandem dyes; and
measuring the fluorescence intensities of each said first and second phycobiliprotein or phycobiliprotein-containing tandem dye;
   wherein each said first and second phycobiliprotein or phycobiliprotein-containing tandem dye upon activation produces a different detectable fluorescence intensity for each said first cell population and said second cell population.

2. A method for a single-measurement quantification of multiple populations of cells comprising:

(a) providing between one to multiple pairs of selected cell populations, a first population of each said pair having a first binding partner density which is substantially equivalent to the density of a second binding partner on a second population of each said pair, said first binding partner being found only in said first cell population of each pair, and said second binding partner being found only in said second cell population of each pair, wherein each pair of cell populations has a different first binding partner and a different second binding partner than each other pair of cell populations comprising said multiple pairs;

(b) providing for each first population a first ligand labeled directly with a phycobiliprotein or a phycobiliprotein-containing tandem dye, said first ligand capable of binding to said first binding partner and differing among each said first population; and said phycobiliprotein or tandem dye differing among each said first ligand;

(c) providing for each second population a second ligand labeled with an aminodextran-(phycobihiprotein or phycobiliprotein-containing tandem dye) conjugate, said second ligand capable of binding to said second binding partner and differing among each said second binding partner; wherein within a pair of cell populations said phycobiliprotein or phycobiliprotein-containing tandem dye of said conjugate is the same as the phycobiliprotein or phycobiliprotein-containing tandem dye of the first ligand, and wherein the phycobiliprotein or phycobiliprotein-containing tandem dye of each pair of ligands is a different color;

(d) incubating a biological sample comprising said multiple selected cell populations with each pair of said first and said second labeled ligands for a time sufficient to permit binding partner-labeled ligand complexes to form therebetween;

(e) exciting each phycobiliprotein or phycobiliprotein-containing tandem dye in each said complex with a laser excitation line to cause it to fluoresce; and (f) measuring the intensities of fluorescent emissions of each said first cell population bound to each said labeled first ligand and the fluorescent emissions of each said second population bound to each said labeled second ligand in a single measurement using flow cytometry;

wherein within each pair of cell populations, said first labeled ligand provides a fluorescent signal of the same color but quantitatively distinguishable intensity from that of the second labeled ligand, and wherein the cell populations are distinguished by detectable variations in label intensity and color.

3. The method according to claim 1 or claim 2 wherein said phycobiliprotein present on said first and second ligand is selected from the group consisting of phycocyanin, allophycocyanin (APC), allophycocyanin B, phycoerythrin (PE) and R-phycoerythrin.

4. The method according to claim 1 or claim 2 wherein said phycobiliprotein-containing tandem dye present on said first and second ligand is selected from the group consisting of phycoerythrin-cyanin 5.1 (PC5), PE-Cy7, phycoerythrin-texas red (ECD), APC-Cy5 and APC-Cy7.

5. The method according to claim 1 or claim 2, wherein said phycobiliprotein or phycobihiprotein-containing tandem dye fluoresces under laser excitation line 488 $Ar^+$.

6. The method according to claim 1 or claim 2, wherein said phycobiliprotein or phycobilprotein-containing tandem dye fluoresces under laser excitation line 632.8 nm He/Ne.

7. The method according to claim 1 or claim 2, wherein said phycobiliprotein or phycobiliprotein-containing tandem dye fluoresces under simultaneous laser excitation lines 488.4 and 632.8.

8. The method according to claim 1 or claim 2, wherein said population of cells are white blood cells.

9. The method according to claim 1 or claim 2, wherein said ligand is an antibody or functional fragment and said binding partner is a receptor.

10. The method according to claim 1 or claim 2, wherein said ligand is an oligonucleotide.

11. The method according to claim 10, wherein said binding partner is a nucleic acid sequence.

12. The method according to claim 1 or claim 2, wherein said ligand is an major histocompatibility complex (MHC)-peptide-(streptavidin or avidin) complex.

13. The method according to claim 1 or claim 2, wherein the intensity difference between said first and second labeled ligands is greater than the intensity difference observed due to the range of naturally-occurring binding partner densities for said first and second cell populations in normal donors.

14. The method according to any of claims 1 to 13 wherein said aminodextran-cross-inked ligand-(phycobiliprotein or phycobiliprotein-containing tandem dye) conjugate contains two to twenty phycobiliproteins or tandem dye molecules per aminodextran molecule, wherein said aminodextran has a degree of substitution with a C2 to C6 diaminoalkane of $1/142$ to $1/5$.

15. The method according to claim 14, wherein said aminodextran has a degree of substitution with 1,3-diaminopropane of $1/45$ to $1/5$.

16. The method according to claim 1 or claim 2, wherein said ligand is an antibody selected from the group consisting of BB27, BY55 and anti-IL-12.

17. The method according to claim 1 or claim 2, wherein the aminodextran is 5X-aminodextran.

18. The method according to claim 1 or claim 2, wherein the aminodextran is 1X-aminodextran.

19. The method according to claim 1 or claim 2, further comprising distinguishing an additional cell population by labeling it with a marker having an excitation emission of less than 550 nm.

20. The method according to claim 1 or claim 2, further comprising distinguishing an additional cell population by labeling it with a marker selected from the group consisting of a green fluorescent protein and a blue fluorescent protein.

21. A ligand aminodextran-tandem dye conjugate, which conjugate contains two to twenty phycobiliproteins per aminodextran molecule, wherein said aminodextran has a degree of substitution of $1/142$ to $1/5$ with a C2 to C6 diaminoalkane.

22. The ligand aminodextran-tandem dye conjugate according to claim 21, wherein said aminodextran has a degree of substitution with 1,3-diaminopropane in the range of $1/45$ to $1/7$.

23. The ligand aminodextran-tandem dye conjugate according to claim 21 or 22, wherein said ligand is selected from the group consisting of an antibody or a functional fragment thereof, an oligonucleotide, and a major histocompatibility complex (MHC)-peptide complex.

24. The ligand aminodextran-tandem dye conjugate according to claims 21 or 22, wherein said figand is an antibody selected from the group consisting of BB27, BY55, and anti-IL-12.

25. The ligand aminodextran-tandem dye conjugate according to claim 21 or 22, wherein said tandem dye is selected from the group consisting of PC5, PE-Cy7, ECD, APC-Cy5 and APC-Cy7.

26. The ligand aminodextran-tandem dye conjugate according to any of claims 1, 2 or 21, wherein the aminodextran is 5X-aminodextran.

27. The ligand aminodextran-tandem dye conjugate according to any of claims 1, 2 or 21, wherein the aminodextran is 1X-aminodextran.

* * * * *